US011033460B2

(12) United States Patent
Park

(10) Patent No.: US 11,033,460 B2
(45) Date of Patent: Jun. 15, 2021

(54) PASSAGE DEVICE, VALVE, RECEPTION DEVICE INCLUDING SAME, CONTENT MOVEMENT DEVICE, AND CONTENT DEVICE

(71) Applicant: Kyungdo Park, Seoul (KR)

(72) Inventor: Suhjun Park, Seoul (KR)

(73) Assignee: Kyungdo Park, Seoul (KR)

( * ) Notice: Subject to any disclaimer, the term of this patent is extended or adjusted under 35 U.S.C. 154(b) by 161 days.

(21) Appl. No.: 16/071,375

(22) PCT Filed: Jan. 31, 2017

(86) PCT No.: PCT/KR2017/001023
§ 371 (c)(1),
(2) Date: Jul. 19, 2018

(87) PCT Pub. No.: WO2017/135654
PCT Pub. Date: Aug. 10, 2017

(65) Prior Publication Data
US 2020/0022875 A1 Jan. 23, 2020

(30) Foreign Application Priority Data

Feb. 1, 2016 (KR) .................. 10-2016-0012597
Mar. 24, 2016 (KR) .................. 10-2016-0035597
(Continued)

(51) Int. Cl.
*B65D 83/04* (2006.01)
*A61J 7/00* (2006.01)
(Continued)

(52) U.S. Cl.
CPC ............. *A61J 7/0076* (2013.01); *A61J 1/03* (2013.01); *A61J 7/0418* (2015.05); *A61J 7/0436* (2015.05);
(Continued)

(58) Field of Classification Search
None
See application file for complete search history.

(56) References Cited

U.S. PATENT DOCUMENTS 1,752,527 A 4/1930 Howard
2,023,537 A 12/1935 Myers
(Continued)

FOREIGN PATENT DOCUMENTS

AU 2003267101 4/2005
BE 477193 A 12/1947
(Continued)

OTHER PUBLICATIONS

Extended European Search Report dated Oct. 19, 2018 relating to European Application No. 17747699.1, 8 pages.
(Continued)

*Primary Examiner* — Gene O Crawford
*Assistant Examiner* — Ayodeji T Ojofeitimi
(74) *Attorney, Agent, or Firm* — Ladas & Parry, LLP

(57) ABSTRACT

The present invention relates to a passage device, a valve, a reception device including the same, a content movement device, and a content device. The present invention comprises a passage operation part included in a housing to move and guide contents, wherein the passage operation part comprises a content passage means for moving the contents. Unlike the prior art, the present invention can ensure a content passage space and adjust the passage space and a reception space to prevent reception of contents exceeding a required amount. Further, the present invention can stably induce the passage of a required amount of contents within a predetermined range, and prevent remaining of an excessive amount of contents in conjunction with the limiting of the content reception space, thereby adjusting the amount (number) of received contents.

24 Claims, 57 Drawing Sheets

(30) Foreign Application Priority Data

| | | |
|---|---|---|
| Jul. 20, 2016 | (KR) | 10-2016-0092326 |
| Oct. 2, 2016 | (KR) | 10-2016-0127193 |
| Nov. 29, 2016 | (KR) | 10-2016-0160800 |
| Dec. 7, 2016 | (KR) | 10-2016-0166241 |
| Jan. 26, 2017 | (KR) | 10-2017-0012707 |

(51) Int. Cl.
 *A61J 7/04* (2006.01)
 *A61J 1/03* (2006.01)
 *B65B 57/18* (2006.01)

(52) U.S. Cl.
 CPC .......... *A61J 7/0445* (2015.05); *A61J 7/0481* (2013.01); *B65B 57/18* (2013.01); *B65D 83/0427* (2013.01); *A61J 2200/30* (2013.01); *B65D 2583/0409* (2013.01); *B65D 2583/0427* (2013.01)

(56) References Cited

U.S. PATENT DOCUMENTS

| | | | |
|---|---|---|---|
| 2,086,296 | A | 7/1937 | Gilbert |
| 2,102,877 | A | 12/1937 | Barnett |
| 2,957,503 | A | 10/1960 | Stifter |
| 3,480,182 | A | 11/1969 | Rigor |
| 3,620,413 | A | 11/1971 | Borsum |
| 3,628,679 | A | 12/1971 | Armour |
| 3,637,109 | A | 1/1972 | Stifter |
| 3,777,924 | A | 12/1973 | Kayser et al. |
| 3,833,147 | A | 9/1974 | Borsum et al. |
| 3,985,274 | A * | 10/1976 | Lubalin ............... G01F 11/261 222/362 |
| 4,530,447 | A | 7/1985 | Greenspan |
| 4,653,668 | A | 3/1987 | Gibilisco et al. |
| 4,732,387 | A | 3/1988 | Elinski |
| 4,782,984 | A | 11/1988 | Su |
| 5,110,008 | A | 5/1992 | Moulding, Jr. et al. |
| 5,219,093 | A | 6/1993 | Moulding, Jr. et al. |
| D371,297 | S | 7/1996 | Robbins, III |
| 5,927,558 | A | 7/1999 | Bruce |
| 6,112,942 | A | 9/2000 | Deacon |
| 6,488,174 | B1 | 12/2002 | Cho |
| 8,322,567 | B2 | 12/2012 | Giraud |
| 8,657,155 | B2 | 2/2014 | Dwork et al. |
| 9,505,530 | B2 | 11/2016 | Downey et al. |
| 9,636,279 | B2 | 5/2017 | Song et al. |
| 2002/0166869 | A1 | 11/2002 | Autonell |
| 2004/0094566 | A1 | 5/2004 | Renaud |
| 2007/0181614 | A1 | 8/2007 | Rvachov et al. |
| 2008/0290110 | A1 | 11/2008 | Gelardi et al. |
| 2012/0228324 | A1 | 9/2012 | Gatski |
| 2013/0110283 | A1* | 5/2013 | Baarman ............... A61J 7/0076 700/236 |
| 2014/0353327 | A1 | 12/2014 | Bae et al. |
| 2016/0068328 | A1* | 3/2016 | 'T Lam ............... A61J 1/03 53/475 |
| 2016/0107820 | A1* | 4/2016 | Macvittie ............... A61J 7/049 221/13 |
| 2016/0159555 | A1 | 6/2016 | Park |
| 2016/0200485 | A1 | 7/2016 | Quinones et al. |
| 2017/0333283 | A1 | 11/2017 | Park |

FOREIGN PATENT DOCUMENTS

| | | |
|---|---|---|
| CN | 2094523 U | 1/1992 |
| CN | 101003315 A | 7/2007 |
| CN | 103086088 | 5/2013 |
| CN | 204264698 U | 4/2015 |
| CN | 105073601 | 11/2015 |
| CN | 204840318 | 12/2015 |
| CN | 107635887 A | 1/2018 |
| DE | 8030162 U1 | 2/1981 |
| EP | 2 639 181 A2 | 9/2013 |
| EP | 3 263 484 A1 | 1/2018 |
| GB | 2345898 A | 7/2000 |
| JP | 47-009941 | 5/1972 |
| JP | 48-6298 | 1/1973 |
| JP | S57008526 S | 1/1982 |
| JP | 1983113673 U | 8/1983 |
| JP | S58202499 A | 11/1983 |
| JP | 1985106966 U | 7/1985 |
| JP | 5-49648 | 3/1993 |
| JP | 11-100113 | 4/1999 |
| JP | 2002-362652 | 12/2002 |
| JP | 2005280715 A1 | 10/2005 |
| JP | 2006506287 A | 2/2006 |
| JP | 3130875 | 4/2007 |
| JP | 3942019 B2 | 7/2007 |
| JP | 2007319205 A | 12/2007 |
| JP | 2007319502 A | 12/2007 |
| JP | 2008239204 A | 10/2008 |
| JP | 2009102067 A | 5/2009 |
| JP | 2011011763 A | 1/2011 |
| JP | 4846454 B2 | 12/2011 |
| JP | 2013-154915 | 8/2013 |
| JP | 2013545681 A | 12/2013 |
| JP | 2016-531056 | 10/2016 |
| JP | 2016-504141 | 2/2018 |
| KR | 200315702 | 5/2003 |
| KR | 200318864 | 6/2003 |
| KR | 20-0360697 | 8/2004 |
| KR | 200422318 | 7/2006 |
| KR | 100978528 B1 | 8/2010 |
| KR | 10-0993722 B1 | 11/2010 |
| KR | 1020110002347 A | 1/2011 |
| KR | 20120096798 A | 8/2012 |
| KR | 101210435 | 12/2012 |
| KR | 101312560 B1 | 9/2013 |
| KR | 1020140119170 A | 10/2014 |
| KR | 20140138187 A | 12/2014 |
| KR | 20140141277 A | 12/2014 |
| KR | 20150106289 A | 9/2015 |
| WO | 2014114943 A1 | 7/2014 |
| WO | 2015030450 A1 | 3/2015 |
| WO | 2015/150240 | 10/2015 |
| WO | 2016137186 A1 | 9/2016 |

OTHER PUBLICATIONS

International Search Report of related application PCT/KR2017/001023 filed Jan. 31, 2017, dated May 4, 2017, 4 pages.
International Preliminary Report on Patentability for PCT/KR2017/001023 dated Aug. 7, 2018 and its English translation from WIPO.
Written Opinion of the International Searching Authority for PCT/KR2017/001023 dated May 4, 2017 and its English translation from WIPO.
Decision to Grant dated Jun. 30, 2020 for Chinese Patent Application No. 201780007684.X and its English translation by Global Dossier.
Office Action dated Mar. 31, 2020 for Chinese Patent Application No. 201780007684.X and its English translation by Global Dossier.
Office Action dated May 20, 2019 for Chinese Patent Application No. 201780007684.X and its English translation by Global Dossier.
Decision to Grant dated Jun. 2, 2020 for Japanese Patent Application No. 2018-540154 and its English translation by Global Dossier.
Office Action dated Jul. 30, 2019 for Japanese Patent Application No. 2018-540154 and its English translation by Global Dossier.
Notice to Grant dated Mar. 29, 2018 for Korean Patent Application No. 10-2017-0012707 and its English translation by Global Dossier.
Office Action dated May 19, 2017 for Korean Patent Application No. 10-2017-0012707 and its English translation by Global Dossier.
Office Action dated Sep. 27, 2017 for Korean Patent Application No. 10-2017-0012707 and its English translation by Global Dossier.
Extended European Sarch Report dated Oct. 17, 2018 for European Patent Application No. 16755836.0.
Office Action dated Jun. 26, 2019 for Indian Application No. 201747029821.

(56) References Cited

OTHER PUBLICATIONS

Office Action dated Jul. 12, 2019 for Chinese Application No. 201680024081.6 and its English translation from Global Dossier.
Examination Report dated Oct. 2, 2019 for Canadian Patent Application No. 2,977,946.
Office Action dated Apr. 3, 2020 for Brazilian Patent Application No. BR112017018196-7 and its English machine translation by Google Translate.
Decision to Grant dated Jun. 2, 2020 for Japanese Patent Application No. 2017-563903 and its English translation by Global Dossier.
Office Action dated Oct. 8, 2019 for Japanese Patent Application No. 2017-563903 and its English translation by Global Dossier.
Office Action dated Nov. 20, 2018 for Japanese Patent Application No. 2017-563903 and its English translation by Global Dossier.
Office Action dated Jul. 7, 2016 for Korean Patent Application No. 10-2016-0019877 and its English translation by Global Dossier.
Office Action dated May 16, 2017 for Korean Patent Application No. 10-2016-0019877 and its English translation by Global Dossier.
Examination Report dated Sep. 5, 2018 for Australian Patent Application No. 2016224240.
Examination Report dated May 1, 2018 for Canadian Patent Application No. 2,977,946.
Office Action dated Mar. 12, 2020 for Chinese Patent Application No. 201680024081.6 and its English translation by Global Dossier.
Notice to Grant dated Aug. 6, 2020 for Chinese Patent Application No. 201680024081.6 and its English translation by Global Dossier.
Office Action dated Nov. 5, 2018 for Chinese Patent Application No. 201680024081.6 and its English translation by Google Translate.
Notice of Allowance dated Dec. 4, 2020 for U.S. Appl. No. 15/673,145.
Ex Parte Quayle Action dated Jul. 9, 2020 for U.S. Appl. No. 15/673,145.
Final Office Action dated Apr. 2, 2020 for U.S. Appl. No. 15/673,145.
Office Action dated Sep. 19, 2019 for U.S. Appl. No. 15/673,145.
Final Office Action dated Apr. 5, 2019 for U.S. Appl. No. 15/673,145.
Office Action dated Dec. 5, 2018 for U.S. Appl. No. 15/673,145.
International Preliminary Report on Patentability (Chapter II) for PCT/KR2016/001727 dated Sep. 8, 2016 and its English translation from WIPO.
Written Opinion of the International Searching Authority for PCT/KR2016/001727 dated Jun. 15, 2016 and its English translation from Google Translate.
International Search Report for PCT/KR2016/001727 dated Jun. 15, 2016 and its English translation from WIPO.

* cited by examiner

US 11,033,460 B2

PASSAGE DEVICE, VALVE, RECEPTION DEVICE INCLUDING SAME, CONTENT MOVEMENT DEVICE, AND CONTENT DEVICE

CROSS-REFERENCE TO RELATED APPLICATIONS

This application is a national stage application of PCT/KR2017/001023 filed on Jan. 31, 2017, which claims priority to Korean Patent Application No. 10-2016-0012597 filed on Feb. 1, 2016, Korean Patent Application No. 10-2016-0035597 filed on Mar. 24, 2016, Korean Patent Application No. 10-2016-0092326 filed on Jul. 20, 2016, Korean Patent Application No. 10-2016-0127193 filed on Oct. 2, 2016, Korean Patent Application No. 10-2016-0160800 filed on Nov. 29, 2016, Korean Patent Application No. 10-2016-0166241 filed on Dec. 7, 2016, and Korean Patent Application No. 10-2017-0012707 filed on Jan. 26, 2017, the entire contents of which are incorporated herein by reference for all purposes.

TECHNICAL FIELD

The present invention relates to a passage device, a valve, an accommodation device including the same, a contents movement device, and a contents device, and more particularly, to a passage device, a valve, an accommodation device including the same, a contents movement device, and a contents device in which a variable passage space for contents is provided so as to stably allow a passage of contents within a certain range to adjust the passage space and a reception space in relation to providing the passage space for contents in order to restrict an excessive quantity of contents in addition to a demanded quantity thereof from passing or being received.

BACKGROUND

Generally, digestive medicines, vitamins, medication such as confectioneries and the like, dietary supplements, and foodstuffs are manufactured as solid, powder, or liquid contents, and tools, devices, and the like are manufactured in the form of solid contents (hereinafter, referred to as "contents").

Contents of medication and foodstuffs are taken as a fixed quantity or a required quantity thereof so as to not only provide maximum effects thereof but also prevent overdose or addiction.

Such contents are sold while being accommodated in a certain storage container. A general contents storage container has a structure including a container body which accommodates a plurality of pieces of contents therein and a cap openably combined with an inlet of the container body.

Accordingly, in order to take a dose of or ingest contents of a storage container, the cap of the container body is opened, and contents accommodated in the container body are withdrawn on a palm or the cap to take a dose.

The above technical configuration is a related art for aiding in understanding of the present invention but does not signify a conventional technology well known in the art.

As a container for discharging a fixed quantity, Korean Patent Publication No. 10-2012-0096798 discloses A Cap for Discharging Constant Rate of Pills.

SUMMARY

According to aspects of the present invention, a passage device comprises a passage operation portion which has an opening portion and is configured to guide movement of contents. The passage operation portion comprises a contents passage means configured to move the contents. The contents passage means comprises a passage movement portion configured to be opened by movement to allow the contents to pass therethrough and the passage movement portion is provided in the opening portion to be movable like a seesaw.

DETAILED DESCRIPTION

Figure 1:
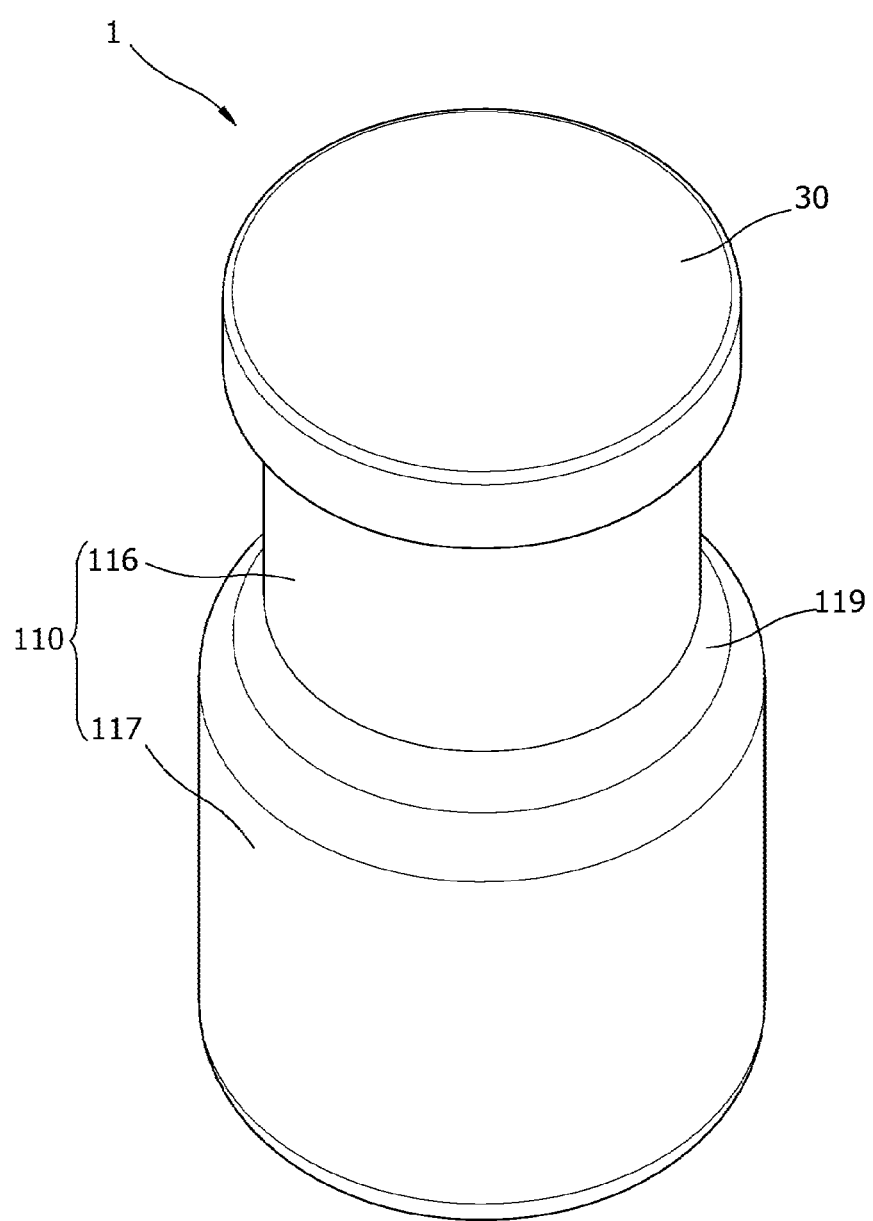
FIG. 1 is a perspective view of a contents movement device including a passage device according to a first embodiment of the present invention.

In such a container for discharging a fixed quantity, whenever a user takes out contents by tilting an accommodation device such as a container device for taking contents, since contents pour out all at once, it is difficult to take out contents one by one or in a required quantity.

When less residual contents are in the accommodation device, it is necessary to pay careful attention and tilt the accommodation device to take out contents located at a bottom of the accommodation device such that it is difficult to reach contents with a hand when contents to be taken out are located in the accommodation device at the bottom thereof.

Accordingly, recently an accommodation device which allows contents therein to be taken out one by one has been disclosed. However, a pump type accommodation device, which has currently been invented and is in use and includes a core configured to support contents in the accommodation device and an accommodation device body configured to move up and down to discharge a part of contents through a through hole at a top of the accommodation device by using the core, has problems in which since it is necessary to maximally move the entire accommodation device body including a lid part up and down, a manipulation distance for operation is large and it is necessary to pick up and set down all of the contents.

In addition, a variety of foodstuffs, medication, goods, or the like are provided in such accommodation devices and an opening or closing device provided at a general accommodation device has no particular function except an opening or closing function. Also, since the opening or closing device is opened to be used in order to take out a certain amount of contents, unavoidably, all of the contents of the accommodation device are easily exposed such that contents are contaminated or come into contact with air to be easily oxidized.

In addition, in order to take only a fixed quantity of contents, a finger may put into the accommodation device or the accommodation device may be tilted to pour out a part of contents on a palm and residual contents are stored in the accommodation device such that contents are easily exposed to external contaminants.

Additionally, in the case of the conventional accommodation device, it is difficult to precisely sense a quantity of contents discharged therefrom and to perform accurate administration.

Also, an apparatus configured to pass only a fixed quantity of contents by opening or closing a passage means included in a conventional container which stores contents, and particularly, by pivoting of an opening or closing member included in the passage means has been disclosed. However, according to a conventional art, when the standing container tilts toward the ground, the opening or closing member pivots due to only a weight thereof such that it is difficult to adjust the pivoting of the opening or closing member according to a tilting angle of the container. Accordingly, a user has to repetitively attempt to tilt or stand the container several times in order to discharge a fixed quantity of contents from the container.

Accordingly, it is necessary to make improvements thereto.

The present invention is directed to providing a passage device, a valve, an accommodation device including the same, a contents movement device, and a contents device, which stably induce a passage of a fixed quantity of contents by providing a passage space for the contents by varying the passage space.

The present invention is directed to providing a passage device, a valve, an accommodation device including the same, a contents movement device, and a contents device, which provide a passage space for contents and close the passage space so as to not allow the contents to pass in order to prevent a passage of additional contents when a fixed quantity of the contents has passed.

The present invention is directed to providing a passage device, a valve, an accommodation device including the same, a contents movement device, and a contents device, which prevent contents from pouring out at once when a user tilts the accommodation device or the contents movement device to take out the contents.

The present invention is directed to providing a passage device, a valve, an accommodation device including the same, a contents movement device, and a contents device, which include a contents passage means configured to open a contents passing side of the accommodation device or the contents movement device while a fixed quantity or a demanded quantity of solid, power, or liquid contents is discharged from the accommodation device or the contents movement device so as to stably allow a passage of the fixed quantity of contents.

The present invention is directed to providing a passage device, a valve, an accommodation device including the same, a contents movement device, and a contents device, which restrict a movement angle of a contents passage means configured to open a contents passing side of the accommodation device or the contents movement device so as to improve opening or closing responsiveness.

The present invention is directed to providing a passage device, a valve, an accommodation device including the same, a contents movement device, and a contents device, in which a movement angle of a passage movement portion connected to an opening member is restricted so as to restrict an opening angle when a stopper opens the opening member.

The present invention is directed to providing a passage device, a valve, an accommodation device including the same, a contents movement device, and a contents device, in which a passage path portion is formed to extend between an entrance side and a discharge side of contents to move and guide the contents toward a passage movement portion and a movement quantity of the contents moving toward the passage movement portion is restricted.

The present invention is directed to providing a valve provided in a contents movement device which is opened ambilaterally so as to induce a passage of contents toward one side of the contents movement device by pivoting for opening.

The present invention is directed to providing a passage device, a valve, an accommodation device including the same, a contents movement device, and a contents device, in which a standby storage portion provided separately from a contents passage means resisting an inflow of unnecessarily excessive contents which pass through the contents passage means into a standby storage space so as to adjust residual contents in the standby storage portion to be a demanded quantity required by a user.

The present invention is directed to providing a passage device, a valve, an accommodation device including the same, a contents movement device, and a contents device, which are capable of providing a passage space for contents while varying the passage space, stably inducing reception of a demanded quantity of contents by blocking an inflow of unnecessarily excessive contents in a stage of receiving contents which has passed, and adjusting a quantity of contents which pass to be received.

The present invention is directed to providing a passage device, a valve, an accommodation device including the same, a contents movement device, and a contents device, in which a contents standby storage portion is provided in an opening or closing device of the accommodation device to separately store and then use solid, powder, or liquid contents.

The present invention is directed to providing a passage device, a valve, an accommodation device including the same, a contents movement device, and a contents device, which allow a user to directly put a demanded quantity of contents into his or her hand or another reception device through only one operation of passing the contents.

The present invention is directed to providing a passage device, a valve, an accommodation device including the same, a contents movement device, and a contents device, which effectively provide only a demanded quantity of contents by tilting or shaking the accommodation device when there is no space to allow a user to put his or her two fingers thereinto to pick up a pill due to a narrow opening portion as in a general accommodation device which stores medication such as oblong pills.

The present invention is directed to providing a passage device, a valve, an accommodation device including the same, a contents movement device, and a contents device, which are applicable to a variety of solid, powder, or liquid contents such as medication, dietary supplements, foodstuffs, tools, devices and the like.

The present invention is directed to providing an administration management device configured to precisely detect the number of discharged pieces of medication and manage fixed-quantity administration for a user on the basis thereof.

The present invention is directed to providing an administration management device configured to accurately administer a user with medication according to an administration schedule by monitoring an administration state of a user.

One aspect of the present invention provides a passage device including a passage operation portion which has an opening portion and is configured to guide movement of contents. Here, the passage operation portion includes a contents passage means configured to move the contents. The contents passage means includes a passage movement portion configured to be opened by movement to allow the contents to pass therethrough, and the passage movement portion is provided in the opening portion to be movable like a seesaw.

When the passage operation portion tilts within a set angle due to the seesaw movement, the passage operation portion may remain in an initial state and may not open the opening portion.

The opening portion may be opened due to a force of the contents pushing on the passage movement portion or due to a weight of the passage movement portion and the force of the contents pushing on the passage movement portion so as to guide a set quantity of contents to pass.

The set angle may be a tilting angle not more than 180 degrees from an initial state in which a contents movement device, which includes the opening portion, stands.

The passage movement portion may perform the seesaw movement due to a weight-leaning phenomenon on a left side or a right side on the basis of a movement member which is a rotational center.

In a standby state in which the contents movement device including the opening portion tilts, a weight leans toward a blocking member on the basis of the movement member which is the rotational center, and the blocking member is held by a stopper such that the passage movement portion may maintain a state in which the blocking member does not block and opens the opening portion.

When the contents movement device including the opening portion tilts within the set angle, the passage movement portion may remain in a state in which an opening member blocks the opening portion due to weight-leaning in a direction opposite to a tilting direction.

When the contents movement device including the opening portion tilts, a weight of the contents which move toward the opening portion is added such that the passage movement portion may pivot on the basis of the movement member, which is the rotational center, and open the opening portion.

A device body with which the passage operation portion is combined may be included.

The passage movement portion may include the opening member which moves in a passage direction of the contents and forms a passage space for the contents.

The passage movement portion may include the blocking member, in conjunction with the opening portion, which blocks at least a part of the opening portion to allow the contents to partially pass or not pass.

The passage movement portion may maintain the initial state due to the stopper when the contents do not come into contact while the passage operation portion tilts within a set angle.

While the blocking member opens the opening portion, when a set quantity of the contents, which is a single or a plurality of pieces of the contents, enters a gap between the blocking member and the opening member, a weight may be added to the passage movement portion such that the passage movement portion may rotate.

The passage movement portion may move with the contents due to friction with the contents which come into contact with a bottom member between the opening member and the blocking member or a force of the contents pushing the opening member.

The passage operation portion may sense the discharged contents by using a sensor module.

The sensor module may include a sensor portion which senses the contents which pass through the opening portion or approach the opening portion and a sensing control portion which controls the sensor portion to sense the contents, generates medication-taking state information according to a result of sensing, and transmits the medication-taking state information to a medication-taking guide terminal.

The sensing control portion may emit light toward the opening portion by using the sensor portion and may sense the contents on the basis of the light reflected by the contents which are discharged through the opening portion.

The sensing control portion may sense the contents discharged through the opening portion by using a time difference between a time of emitting the light and a time of receiving the light through the sensor portion.

When the time difference is within a preset set value, the sensing control portion may determine that the contents have passed through the opening portion.

One aspect of the present invention provides a passage device including a passage operation portion which has an opening portion and is configured to guide movement of contents. Here, the passage operation portion includes a contents passage means configured to move the contents. The contents passage means includes a passage movement portion configured to be opened by a pivoting movement to allow the contents to pass therethrough. The passage movement portion reciprocally pivots using the principle of levers at the opening portion on the basis of a movement member so as to open or close the opening portion.

When the passage operation portion pivots within a set angle, the passage movement portion may maintain a state in which the opening portion is closed due to a weight thereof and may sequentially open or close the opening portion due to a pushing force of the contents or the weight of the passage movement portion and the force of the contents pushing on the passage movement portion so as to guide a set quantity of the contents to pass therethrough.

The passage movement portion may include a balancing portion which suppresses the passage movement portion from tilting more than the passage operation tilts due to the weight of the passage movement portion.

The passage movement portion may include the opening member which moves in a passage direction of the contents and forms a passage space for the contents.

The passage movement portion may include the blocking member which blocks, in conjunction with the opening portion, at least a part of the opening portion to allow the contents to partially pass or not to pass The passage operation portion may have a shape which prevents pivoting caused by the weight of the passage movement portion due to weight balance until the set quantity of contents comes into contact with the opening member.

The passage movement portion may further include a movement control member for setting a balance of the center of gravity of lever movement.

One aspect of the present invention provides a passage device including a housing which stores contents, a passage operation portion provided inside the housing and configured to guide movement of contents and a supply guide portion formed in the housing in order to set a movement direction and a movement state of the contents to guide a single piece or a fixed quantity of the contents which move toward an outlet of the passage operation portion to be discharged.

The passage operation portion may include a contents passage means which allows contents to move. Here, the contents passage means may include a passage movement portion which is opened by movement in order to pass the contents. The passage movement portion may include an opening member which moves in a passage direction of the contents and forms a passage space for the contents and a blocking member which blocks, in conjunction with the opening member, at least a part of the opening portion to allow the contents to partially pass or not to pass. The blocking member may prevent contents which exceed the fixed quantity thereof from passing through the opening portion by blocking, in conjunction with the opening member, at least the part of the opening portion.

The passage operation portion may include a fixing member which forms the opening portion in order to pass the contents therethrough and a movement guide portion which guides the contents to move toward the contents passage means. The housing may include a reduced-diameter portion configured to hold the fixing member and to guide the contents to move toward the movement guide portion and an enlarged-diameter portion configured to have an internal space larger than that of the reduced-diameter portion to store an initially-set quantity of the contents.

The passage operation portion may include a fixing member which forms the opening portion in order to pass the contents therethrough and a movement guide portion which guides the contents to move toward the contents passage means. Also, the housing may hold the fixing member and guide the contents to move toward the movement guide portion by using the supply guide portion.

The passage operation portion may include a fixing member which forms the opening portion in order to pass the contents therethrough and a movement guide portion which guides the contents to move toward the contents passage means. Also, the housing may hold the fixing member and may include an enlarged-diameter portion formed to guide the contents to move toward the movement guide portion.

The supply guide portion may be formed at the housing to be inwardly convex with a curvature along a circumference of the housing.

The housing may include a reduced-diameter portion formed to guide the contents to move toward the movement guide portion of the enlarged-diameter portion. Also, the supply guide portion may be formed at the enlarged-diameter portion or the reduced-diameter portion to guide movement of the contents.

One aspect of the present invention provides a passage device including a housing which stores contents, a passage operation portion provided inside the housing and configured to guide movement of contents and a supply guide portion formed in the housing in order to set a movement direction and a movement state of the contents to guide a single piece or a fixed quantity of the contents which move toward an outlet of the passage operation portion to be discharged.

The passage operation portion may include a contents passage means which allows contents to move. Here, the contents passage means may include a passage movement portion which is opened by movement in order to pass the contents. The passage movement portion may include an opening member which moves in a passage direction of the contents and forms a passage space for the contents and a blocking member which blocks, in conjunction with the opening member, at least a part of the opening portion to allow the contents to partially pass or not to pass. The blocking member may prevent contents which exceed the fixed quantity thereof from passing through the opening portion by blocking, in conjunction with the opening member, at least the part of the opening portion.

The passage operation portion may include a fixing member which forms the opening portion in order to pass the contents therethrough and a movement guide portion which guides the contents to move toward the contents passage means.

The housing may hold the fixing member and may include a reduced-diameter portion configured to guide the contents to move toward the movement guide portion.

The passage operation portion may include the fixing member which forms the opening portion in order to pass the contents therethrough and a movement guide portion which guides the contents to move toward the contents passage means.

The housing may include the reduced-diameter portion configured to guide the contents to move toward the movement guide portion of the enlarged-diameter portion.

The supply guide portion may be formed at the enlarged-diameter portion or the reduced-diameter portion to guide movement of the contents.

The passage operation portion may include a fixing member which forms the opening portion in order to pass the contents therethrough and a movement guide portion which guides the contents to move toward the contents passage means.

The housing may include the enlarged-diameter portion which holds the fixing member, extends from the reduced-diameter portion through the movement guide portion, and is configured to guide the contents to move toward the movement guide portion and may include the reduced-diameter portion which extends from the enlarged-diameter portion to form the supply guide portion so as to guide the contents to move toward the movement guide portion of the enlarged-diameter portion.

The supply guide portion may be formed at the housing to be inwardly convex with a curvature along a circumference of the housing.

The supply guide portion may be supported to be flush with an end of the movement guide portion to guide movement of the contents.

The contents may be guided to pass through by a modification of the contents passage means.

The passage operation portion may include an opening portion which connects to a passage-anterior portion located before the contents pass through the passage operation portion such that the contents in the passage-anterior portion move. Here, the contents passage means may move the contents through the opening portion.

The passage device may be an opening or closing device which is applied to a contents movement device or an accommodation device and is openable from the contents movement device or the accommodation device. The opening or closing device may include an opening or closing device body and the passage operation portion. The passage operation device may allow the passage-anterior portion and the opening or closing device to be at least partially connected to each other so as to move the contents in the passage-anterior portion of a contents movement device body or accommodation device body to the opening or closing device.

In the passage operation portion, the contents in the passage-anterior portion may move to the opening or closing device due to a modification of the contents passage means.

The passage movement portion may include a movement member, and the movement member may movably connect to the opening member.

The passage operation portion may include a passage path portion which extends from a passage discharge side, which is a side in contact with the contents passage means, and a passage entry side, which is a side that the contents enter. The passage path portion may guide the contents to move toward the contents passage means.

The passage movement portion may include a balancing portion which suppresses the passage movement portion from tilting due to a weight of the opening member in a direction in which the passage operation portion tilts before the contents come into contact with the passage movement portion by applying a weight-leaning force in a direction opposite the direction in which the passage operation portion tilts when the passage operation portion tilts in a direction in which the contents slide toward the passage device.

Depending on whether the passage space formed by movement of the opening member through the opening portion is opened, the contents may be guided to pass through. Also, the opening member may be directly or indirectly connected to the fixing member.

The contents passage means may include a movement member, and the movement member may pivotably connect the opening member.

The passage operation portion may include the fixing member including the opening member to pass the contents pass through.

The contents passage means may include the opening member connected to the fixing member, and the opening member may move and may receive and guide the contents depending on whether the opening portion is opened.

The contents passage means may include the movement member which movably connects to the opening member.

The contents in the passage-anterior portion may move to the opening or closing device or through the opening or closing device due to a modification of the contents passage means.

The contents passage means may include a passage movement portion which moves to be opened to allow the contents to pass through.

The passage movement portion may include the opening member which moves in a passage direction of the contents and forms a passage space of the contents.

The passage operation portion may include the opening portion and may be formed such that the opening portion rises to a certain height.

A passage space for the contents may be formed by at least one of an unfixed free end of the opening member being pushed by the weight of the contents, shaking of the housing including the passage operation portion, and the weight of the opening member.

One side of the opening member may be fixed to the fixing member and the other end thereof may not be fixed and opened by movement so as to prevent a separation of the contents and to form the passage space in the opening portion.

The fixing member may be provided on an inner circumferential surface of an internal through hole space of the passage device to which the opening member is connected or may be a member of the housing included in the passage device.

One or a plurality of such opening members may be included.

When the contents push the opening member, the contents move thereinto as the opening member tilts backward and the blocking member is in conjunction with the opening member to bloc at least a part of the opening portion such that the contents more than the demanded quantity may be prevented from passing through the opening portion.

The passage movement portion may have a shape or a component member of the passage movement portion is combined so as to form a weight or the center of gravity of the balancing portion such that the demanded quantity of contents may be prevented from rotating due to the weight of the passage movement portion before coming into contact with the opening member when the passage operation portion tilts.

The contents passage means may include a movement fixing portion which is provided at the opening portion of the fixing member and pivotably connects the movement member to the fixing member.

The contents passage means may be a passage means which is provided at the passage operation portion to guide a demanded quantity of contents to pass through.

The contents passage means may include a stopper for restricting a rotational angle of the opening member or the blocking member.

When the passage operation portion tilts and the opening member attempts to rotate due to a weight thereof, the rotation of the opening member may be suppressed by an action of a weight-balancing force of the passage movement portion such that the blocking member may not block a passage of the contents until the demanded quantity of the contents pass through the opening portion.

When the passage operation portion tilts and the opening member attempts to rotate due to a weight thereof, the rotation of the opening member may be suppressed by weights and positions of the centers of gravity of the opening member and the movement member such that a passage of the contents may not be blocked until the demanded quantity of the contents pass through the opening portion.

The passage operation portion may include a movement guide portion which guides the contents to move into the contents passage means.

The opening member may open the opening portion by movement of the unfixed free end such that a passage space may be formed to allow the contents to pass therethrough.

The passage movement portion may include an opening member which moves in a passage direction of contents and allows the contents to pass through the passage operation portion.

The passage operation portion may prevent a received demanded quantity of contents which move from the passage-anterior portion from moving back to the passage-anterior portion.

A movement angle of the passage movement portion may be restricted by a single or a plurality of stoppers provided at one or more of the contents passage means, the housing, and a cover.

The passage-anterior portion may include a standby accommodation portion in which contents are stored and wait for withdrawal. The passage-anterior portion and the standby accommodation portion may be partially connected to each other through the opening portion formed at the passage operation portion. The contents in the passage-anterior portion may move to the standby accommodation portion.

The movement member may be provided to be integrated with the opening member or to be separable from the opening member.

The movement member may be connected to the movement fixing portion and may connect to the opening member, which attempts to move in a weight direction or a pushing direction of the contents, by using a hinge.

One side of the opening member may be fixed to the fixing member and the other side thereof may not be fixed so as to open or close the opening portion by movement thereof.

The passage movement portion may further include a movement control member to control movement of the passage movement portion caused by an action of a force of balancing the center of gravity of the passage movement portion.

A cover which is connected to a housing including the passage operation portion and receives contents through the passage device may be included. The cover may be separably combined with the housing.

A movement guide portion which guides contents to move into the passage operation portion may be included.

In the movement control member, when the passage operation portion tilts, the balancing portion may be suppressed from rotating or being reduced in a direction in which the passage operation portion tilts due to a force which acts in a direction in which the balancing portion changes to a balanced state and a force of maintaining a position of the center of gravity in a gravitational direction to make a balance in weight of the balancing portion may be generated by weights of the opening member and the movement control member or weights of the opening member, the movement control member, and at least one separate member which moves with the opening member such that the opening member may not tilt more than the passage operation portion tilts.

The standby accommodation portion may include a resistant side plate member which comes into contact with and resists contents which have passed, on a side surface in a passage direction thereof.

In the passage path portion, when a widthwise length of one side of a piece of contents differs from a widthwise length of the other side thereof, since a minimum inner diameter of a width of a path which is an minimum inner diameter among widths of an internal space of the passage path portion is smaller than or equal to two times a maximum outer diameter of a widthwise direction of the contents which is a maximum outer diameter in a widthwise direction of the piece of contents, two or more pieces of contents may not enter or pass through the passage path portion and only one piece of contents may enter or pass through the passage path portion at once.

When a widthwise length of one side of a piece of contents differs from a widthwise length of the other side thereof, the passage path portion may guide the contents to pass through the passage path portion in a longitudinal direction of the contents.

The contents passage means may include an opening member which moves in a passage direction of contents and forms a passage space for the contents and may include a blocking member which closes, in conjunction with the opening member, at least a part of the opening portion which is opened. When the piece of contents passes frontward through the passage path portion, another piece of contents enters the passage path portion rearward while closely behind the frontward-passing piece of contents, the blocking member which moves in conjunction with the opening member which moves in contact with the frontward-passing piece of contents partially blocks the opening portion such that the rearward-entering piece of contents more than a demanded quantity thereof may come into contact with the blocking member and may move into the opening portion.

A movement guide portion which induces the contents to the passage path portion may be provided below the passage path portion, and at least a part of the movement guide portion may be formed to be inclined such that the contents may be guided to a place where the passage path portion is located.

When the passage operation portion tilts, the contents may be guided to move to the place where the passage path portion is located along an inclined surface of the movement guide portion in a gravitational direction.

The balancing portion may include the opening member which moves in the passage direction of the contents and forms the passage space for the contents and may further include a movement increase control member breaks a balance in a movement direction of the balancing portion and adds a movement force of the balancing portion when the contents come into contact with the opening member and a weight of the contents is transferred to the opening member such that the movement of the balancing portion is performed.

A modification of the contents passage means, which occurs in a rotational modification generated by rotation of at least some of component members of the contents passage means, may not occur until contact with the contents or may be delayed to a time closely before the contact. The modification of the contents passage means may not occur before the contact with the contents caused by a weight thereof and may occur when the passage movement portion and the contents in contact caused by the weight rotate after the contact with the contents caused by the weight.

The opening member may be bent, and an opening member bent portion formed by bending the opening member may be linearly bent or may be a curved surface. The opening member may be bent at an angle equal to or greater than a right angle to ensure a space between the opening member and the blocking member. A demanded quantity of contents which enter the space between the opening member and the blocking member may push the opening member such that the opening member may rotate with the blocking member. The blocking member which rotates may not interfere in the demanded quantity of contents which have pushed the opening member. When contents more than the demanded quantity of contents enter the passage operation portion, the blocking member may block excessive contents.

The blocking member may be bent, and a blocking member bent portion formed by bending the blocking member may be linearly bent or may be a curved surface.

The balancing portion which controls movement of the passage movement portion caused by a weight of the passage movement portion may be included. The balancing portion may include at least one of the movement control member, the opening member, the blocking member, and the movement member. The movement of the passage movement portion caused by the weight may be controlled by a weight and a position of at least one of the movement control member, the opening member, the blocking member, and the movement member.

The movement control member may control at least one of a movement distance and a movement angle of the movement caused by the weight of the opening member.

When the passage operation portion tilts, the movement control member may control the blocking member not to block a passage of the demanded quantity of contents by weight-caused rotation of the opening member or a member which moves with the opening member before the demanded quantity of contents push the opening member. The movement control member may have a weight and a position for controlling weight-caused movement of the passage movement portion including the opening portion or the balancing portion in response to the weight of the opening member or the weight of at least one member which moves with the opening member.

When the passage operation portion tilts, due to the weights of the opening member and the movement control member or the weights of the opening member, the movement control member, and a separate member which moves with the opening member, a force which acts in a direction opposite a direction in which the passage operation portion tilts, that is, a direction for becoming a weight-balancing state on the center of gravity of the balancing portion may be generated such that the opening member may not tilt more than the passage operation portion tilts and may maintain a position in the passage operation portion or a tilt.

When the passage operation portion tilts, a force in which the opening member and the movement control member maintain positions in a gravitational direction due a weight balance may act.

A resistant member provided in the passage operation portion may be included. The resistance member may restrict a passage of contents which pass through the passage operation portion.

A housing with at least one open side may be included. The passage operation portion may be provided in the housing. The contents passage means may be opened by movement in a direction in which contents move so as to induce the contents to pass through the one side of the housing.

In the passage operation portion, the contents may move due to a modification of the contents passage means caused by tilting or shaking of the passage operation portion.

The movement guide portion which guides movement of contents when the passage operation portion tilts may be included. The contents may be guided to pass through along a surface of the movement guide portion due to a weight or inertia of the contents while the movement guide portion tilts.

The movement guide portion may be a housing or may be connected to the housing.

The movement guide portion may extend a guide member to collect contents which move.

The contents passage means may include a passage movement portion which passes the contents by movement. The passage movement portion may move due to at least one of a weight of the passage movement portion, inertia of the passage movement portion, and a force of the contents pushing on the passage movement portion when the passage operation portion tilts or moves.

The passage movement portion may include an opening member which moves in a direction like that of the contents which pass through and allows the passage of the contents.

The passage movement portion may include the blocking member which moves, separately from the opening member, toward the opening member and blocks at least a part of the opening member so as to allow the contents not to pass through or to partially pass through.

The passage movement portion may include a position of the center of gravity of a movement portion of the passage movement portion and a position of a rotational center of the movement portion which is a center of rotational movement of the passage movement portion and the positions differing from each other.

Since the position of the center of gravity of the movement portion of the passage movement portion is located in a direction opposite an external passage direction of the passage device, which is in the rear of the position of the rotational center of the movement portion of the passage movement portion, when the passage operation portion tilts or is shaken, rotational movement of the passage movement portion may be suppressed or delayed due to a difference between the position of the center of gravity of the movement portion and the position of the rotational center of the movement portion.

The passage operation portion may include the opening portion to pass the contents. When the passage operation portion tilts or moves, the passage movement portion may not rotate or may be suppressed from rotating for being opened to allow the contents to pass through the opening portion by only a weight of the passage movement portion.

The passage movement portion may not open the opening portion to a degree which allows the contents to pass therethrough by the weight of the passage movement portion before the contents resist the passage movement portion and open the opening portion.

The passage movement portion may include an accommodation member which moves, in conjunction with the opening member, toward the opening member and moves and accommodates a demanded quantity of contents with the opening member.

The passage movement portion may include a passage compartment portion provided between the opening member and the accommodation member and may accommodate a compartment portion accommodation quantity of contents in the passage compartment portion to guide the accommodated contents to move.

The passage movement portion may include a bottom portion for accommodating contents. The bottom portion may support a bottom of the contents in a gravitational direction in the passage movement portion when the passage device tilts.

When the contents come into contact with a bottom height change portion which is a part rising or protruding from a bottom surface, due to resistance, a position of the contents which pass through the passage movement portion may get higher in a height direction of the bottom height change portion.

Due to the change in position of the contents which pass through, an opening portion space which is opened to allow the contents to pass therethrough decreases. Due to the opening portion space which has decreased, contents more than the accommodation quantity may not pass through the passage movement portion.

The opening member may move to be opened due to the weight thereof or a pushing force of the contents and may guide the contents to pass through.

The passage movement portion may include a stopper for restricting a rotational angle of the opening member.

The passage movement portion may move to be opened due to the weight of the passage movement portion or the pushing force of the contents and may guide the contents to pass through a passage space formed by opening of the passage movement portion.

The modification of the contents passage means operates frontward which is an opening direction of the passage device. The contents passage means may guide the contents to pass through an opened part of the passage space formed by the modification of the contents passage means in an opened state in which an opening or closing device or the cover which opens or closes the housing is not present at the passage operation portion of the housing including the contents passage means.

The contents passage means may induce the contents to pass through by only the modification of the contents passage means caused by resistance of the contents without contact with or resistance by the opening or closing device at the passage operation portion of the housing or a member fixed to the opening or closing device.

The passage movement portion may induce the contents to pass through by the resistance of the contents when the housing including the passage movement portion is opened in a direction in which the contents pass through the contents passage means.

The passage movement portion may move corresponding to movement of the contents caused by workings of gravity and open the passage operation portion to allow the contents to pass therethrough. The contents may pass through the contents passage means due to only workings of gravity caused by an operation of tilting, being turned over, or being shaken of the passage operation portion including the passage movement portion.

The contents may pass through due to rotational movement of the passage movement portion.

After the contents pass through the passage movement portion due to the rotational movement of the passage movement portion, a passage of contents more than a necessary quantity of contents may be prevented.

The rotational movement of the passage movement portion which pass the contents may be performed by gravitational movement of the contents caused by the passage operation portion tilting, being turned over, or being shaken or transmission of a movement force of the contents to the passage movement portion.

The rotational movement of the passage movement portion may include a movement force caused by pushing, by the weight of the contents, on the contents passage means.

The contents may be induced to pass through by the modification of the contents passage means, and the modification of the contents passage means may be a modification caused by movement of the passage movement portion.

The contents may come into contact with a surface provided inside the housing or the passage means and may pass through the contents passage means while sliding.

The modification of the contents passage means caused by rotation due to the center of gravity of the passage movement portion which occurs in rotational movement generated by rotation of at least a part of the passage movement portion may not occur until contact with the contents or may be delayed to an approximate time previous to the contact.

The modification of the contents passage means caused by the rotation due to the weight movement portion may not occur before contact with the contents caused by the weight thereof and may coincide with the contact with the contents caused by the weight thereof.

When the passage operation portion tilts or is shaken, the passage movement portion may rotate on a hinge shaft of the passage operation portion in a gravitational direction due to a weight of at least one part of the passage movement portion. The passage movement portion which has rotated in the gravitational direction may form a passage space of the contents.

When the passage movement portion rotates on a shaft of the housing, the passage movement portion may rotate while being in contact with an inner surface of the housing.

The passage path portion may have a shape which resists such that when contents more than a demanded quantity enter the passage path portion, the contents more than the demanded quantity may not completely pass through the passage path portion.

The passage path portion may include a resistant member or a resistant shape which resists not to allow the contents more than the demanded quantity or all the contents including the demanded quantity thereof to pass through the passage path portion when the contents more than the demanded quantity enter the passage path portion such that the contents more than the demanded quantity may not enter the contents passage means.

A passage of the contents more than the demanded quantity may be interfered by the resistant member or the resistant shape provided at the passage path portion which comes into contact with or resists the contents which enter the passage path portion.

The opening member may be pivotably provided.

The contents passage means may open or close the opening portion by using the modification of the contents passage means.

The contents may easily pass through the opening member due to a position of the contents which move upward.

The bottom portion may include the bottom height change portion which changes a height of the bottom portion. The bottom portion may partially or entirely protrude. When the contents come into contact with a surface of the bottom height change portion and move, due to resistance caused by the weight of the contents against the bottom portion, the bottom height change portion moves in a movement direction of the contents along the bottom portion such that the center of gravity of the passage movement portion moves in the passage direction of the contents and the passage movement portion may move in the passage direction of the contents.

The bottom portion may move in the passage direction of the contents due to the resistance of the contents against the bottom portion caused by the contact therebetween to allow the passage of the contents. The passage movement portion may include the opening member or may move only the movement of the bottom portion without an additional opening member at the passage movement portion.

The bottom portion or the bottom height change portion included in the bottom portion may include at least one of a frictional surface, a frictional material, and a bent shape.

The contents passed by the contents passage means may be at least one of solid, powder, and liquid contents.

The passage movement portion may further include a movement increase control member. The movement increase control member may be formed in a protrusion shape at the bottom portion. Due to the resistance of the contents caused by the weight, the movement increase control member moves in the movement direction of the contents. The center of gravity of the balancing portion may lean in the passage direction of the contents such that a force of the passage movement portion moving in the passage direction of the contents may increase. The movement increase control member increase movement of the passage movement portion in the passage direction of the contents and may allow the contents to pass through the passage operation portion.

The movement guide portion includes a height induction member at an inlet side of contents. The height induction member may include a single or a plurality of stages formed by dividing a height difference generated while the contents move to the contents passage means or may include an inclined surface. The height difference may not block movement of the contents and may induce the movement of the contents so as to induce the contents to stably move to the contents passage means.

One aspect of the present invention provides a passage device provided in an accommodation device which stores contents and configured to induce a passage of the contents. The passage device includes a passage operation portion for allowing the contents to pass through. The passage operation portion includes a contents passage means which allows the contents to move. The contents passage means includes a passage movement portion which forms a passage space for the contents by movement. The passage movement portion includes an opening member which moves in the same direction in which the contents pass through and allows the passage of the contents. When the passage operation portion tilts in a direction in which the contents slide toward the passage device, a weight-leaning force acts in a direction opposite the direction the passage operation portion tilts such that the passage movement portion may suppress the opening member from tilting due to a weight of the opening member at an angle more than the passage operation portion tilts in the direction in which the passage operation portion tilts.

One aspect of the present invention provides a passage device provided in an accommodation device which stores contents and configured to induce a passage of the contents. The passage device includes a passage operation portion for allowing the contents to pass through. The passage operation portion includes a contents passage means which allows the contents to move. The contents passage means includes a passage movement portion which is opened by movement to allow the contents to pass through. The passage movement portion includes an opening member which moves in the same direction in which the contents pass through and allows the passage of the contents. The passage movement portion is a balancing portion which suppresses the passage movement portion from tilting with the passage operation portion at a tilt more than a tilt of the passage operation portion when the passage operation portion tilts. Before the contents slide and come into contact with the opening member as the passage operation portion tilts such that the weight of the contents is added in a direction in which the passage operation portion tilts and a weight leans in the direction in which the passage operation portion tilts, the balancing portion may suppress the movement of the opening member caused by the weight thereof in a direction of being opened to discharge the contents and maintain an open standby state before coming into contact with the contents.

One aspect of the present invention provides a passage device provided in an accommodation device which stores contents and configured to induce a passage of the contents. The passage device includes a passage operation portion for allowing the contents to pass through. The passage movement portion includes an opening member which moves in the same direction in which the contents pass through and allows the passage of the contents. The passage movement portion is a balancing portion which suppresses the passage movement portion from tilting with the passage operation portion at a tilt more than a tilt of he passage operation portion when the passage operation portion tilts. The balancing portion is configured to generate a force of rotating a weight balance state thereof in a direction opposite the direction in which the passage operation portion tilts to pass the contents such that a force in which the opening member does not tilt in the direction in which the passage operation portion tilts and attempts to rotate in the direction opposite the direction in which the passage operation portion tilts may act due to the weight balance of the balancing portion.

One aspect of the present invention provides a passage device including a housing which has at least one open side and a passage operation portion provided inside the housing to guide movement of contents. The passage operation portion includes a contents passage means which allows the contents to move and a fixing member which forms an opening portion for allowing the contents to pass through. The contents passage means includes a passage movement portion which is opened by movement to allow the contents to pass through. The passage movement portion is a balancing portion which suppresses the passage movement portion from tilting with the passage operation portion at a tilt more than a tilt of the passage operation portion when the passage operation portion tilts. A force of the balancing portion to rotate in a direction opposite a direction in which the passage operation portion tilts is resisted by the fixing member or the housing such that rotation in the direction opposite the direction in which the passage operation portion tilts is prevented. Accordingly, the balancing portion does not tilt in the direction, in which the passage operation portion tilts, due to a force thereof to maintain or rotate in a balance state direction and the rotation in the direction opposite the direction in which the passage operation portion tilts caused by the force of the balancing portion to maintain or rotate in the balance state direction may be suppressed by being resisted by the fixing member or the housing.

One aspect of the present invention provides a passage device provided in an accommodation device which stores contents and configured to induce the contents to pass through. The passage device includes a passage operation portion for allowing the contents to pass through. The passage operation portion includes a contents passage means which allows the contents to move. The contents passage means includes a passage movement portion which forms a passage space for the contents by movement. The passage movement portion may include an opening member which moves in the same direction in which the contents pass through and allows the passage of the contents. The passage movement portion is a balancing portion which suppresses the passage movement portion from tilting with the passage operation portion at a tilt more than a tilt of the passage operation portion when the passage operation portion tilts. When the contents come into contact with the opening member as the passage operation portion tilts, all or at least a part of or a weight of the contents is added to the balancing portion such that a weight of the balancing portion leans in a direction in which the passage operation portion tilts. In this case, when the weight leaning in the direction in which the passage operation portion tilts caused by the weight of the contents added to the opening member of the balancing portion is more than a balance-maintaining force of reaching a position of a balanced state of only the balancing portion which attempts to rotate in a direction opposite the direction in which the passage operation portion tilts, the balancing portion may rotate in the direction in which the passage operation portion tilts.

One aspect of the present invention provides a passage device including a housing which has at least one open side and a passage operation portion provided inside the housing and configured to guide movement of contents. The passage operation portion includes a contents passage means which allows the contents to move and a fixing member which forms an opening portion for allowing the contents to pass through. The contents passage means may include a passage movement portion which is opened by movement to allow the contents to pass through. The passage movement portion is a balancing portion which suppresses the passage movement portion from tilting with the passage operation portion at a tilt more than a tilt of the passage operation portion when the passage operation portion tilts. Rotation of the balancing portion is resisted by the fixing member or the housing through contact therewith such that the balancing portion may be prevented from unnecessarily rotating in a direction in which the passage operation portion tilts.

One aspect of the present invention provides a passage device in which a sliding-beginning end of a contents induction portion which introduces contents to a passage path portion is located to be close to or in contact with an inner diameter of a reduced-diameter portion which is a neck part of a housing that is a container body and the sliding-beginning end of the contents induction portion is located to be connected to a supply guide member which has a bent portion such that movement of the contents may be smoothly connected and the contents may be guided to slide from an enlarged-diameter portion to the passage path portion One aspect of the present invention provides a passage device in which in the case of an injection-blown container, an end part of a contents induction portion provided in the passage device has a shape of being inclined, bent, or having a step to partially or entirely connect an inner diameter of a container neck and an inner diameter of a container body such that when a housing tilts and contents slide, the contents may smoothly move to a passage path portion.

One aspect of the present invention provides a passage device including a shape change portion which connects a step between a contents inlet part of a contents induction portion and an enlarged-diameter portion when a step is present between the contents inlet portion of the contents induction portion and the enlarged-diameter portion. The shape change portion is a supply guide portion which guides supply and movement of contents at a step in a housing by connecting a step between a reduced-diameter portion and the enlarged-diameter portion.

One aspect of the present invention provides a passage device in which in the case of not only an injection-blown container in which an inlet is narrower than a container body but also an injection container in which an inlet is not narrower than a container body, since an operation position of a rotating shaft of an opening member of a passage movement portion is located to be spaced apart from an inner diameter of a container housing in an inward direction, a difference in a position of solid contents, which slidably move, may occur and a contents entry part of a contents induction portion which faces a container bottom may be inclined, bent, or include a step to connect a step therebetween.

One aspect of the present invention provides a passage device in which in the case of both an injection-blown container and an injection container, an operation position of an opening member is located inside an inner diameter of the container and a step between the operation position and a position of contents which approach from a container body. Here, a step connection portion which is inclined, bent, or has a stage to connect the step is included. The step connection portion which connects the step between the opening member located to be spaced apart from the inner diameter of the reduced-diameter portion and the inner diameter of the reduced-diameter portion.

One aspect of the present invention provides a passage device in which a step connection portion connects an inside of a container reduced-diameter portion and an inside of a container body such that contents may smoothly slide.

One aspect of the present invention provides a passage device including a supply guide member which is an inclined part which connects a reduced-diameter portion narrower than a container body to an enlarged-diameter portion in which contents are stored and wait for movement. The supply guide member may connect a step generated while a housing tilts and the contents in the enlarged-diameter portion move to a contents induction portion.

One aspect of the present invention provides a passage device in which when a step beginning point which is a step beginning end of a contents induction portion toward a container bottom is larger than an inner diameter of a reduced-diameter portion, in order to insert the passage device into a housing, a passage device bottom which includes a beginning point of a step connection portion toward the container bottom which is the step beginning end of the contents induction portion is inserted perpendicularly, a position of the passage device is moved horizontally, and then the passage device is inserted perpendicularly such that assembling may include three operations of perpendicular movement, horizontal movement which is an intermediate operation, and perpendicular movement.

One aspect of the passage device provides a passage device in which a contents induction portion of the passage device locates a step connection point beginning point close to an inner diameter of a housing and a guide member in a reduced-diameter portion such that the passage device is directly insertable in one direction while being assembled with the housing.

One aspect of the present invention provides a passage device which is applied to a blown container produced such that a container neck which is a reduced-diameter portion is smaller than a container body which is an enlarged-diameter portion. A housing is an injection-blown container and may include a convex container and a reduced-diameter portion in which main components of the passage device are located.

When an outer meter of the entire passage device bottom including the contents induction portion toward the enlarged-diameter portion is formed to be smaller than an inner diameter of the container reduced-diameter portion, the passage device may be inserted into the housing which is the container body in one direction at once without horizontal movement which is an intermediate operation in assembling with the container body.

When the passage device is assembled with the container body, a top end of the reduced-diameter portion may be formed to be wide or a step may be formed inside the reduced-diameter portion to support a bottom from above.

In order to prevent the passage device which is a contents passage dispenser from being separated outward due to a weight of the contents when the container tilts, a protruding portion may be formed on an outer diameter of a top of the passage device, and corresponding thereto, a groove may be formed at a top end of the reduced-diameter portion of the housing such that the protruding portion engage with the groove during insertion.

The contents induction portion of the passage device may locate the step connection point beginning point close to the inner diameter of the housing and the guide member in the reduced-diameter portion such that the passage device is directly insertable in one direction while being assembled with the housing.

Since the step connection portion beginning point of the passage device is closely connected to an inner wall of the enlarged-diameter portion which is the container body, not an inner wall of the reduced-diameter portion, it is unnecessary for the container neck to surround the whole length of the contents induction portion.

The supply guide portion which has a concavely bent shape in the enlarged-diameter portion of the container body and is located to be connected to a step connection portion beginning point end of the contents induction portion may be provided. The contents may smoothly move through the supply guide portion such that the contents may be guided to slide from the container body to the passage path portion of the passage device.

The contents induction portion of the passage device may locate the beginning point of the step connection portion toward the container bottom which is close to the inner diameter of the housing, inside the enlarged-diameter portion. When the step connection portion is provided to be close to the beginning point of the step connection portion toward the container bottom, movement of the contents continues so as to smoothly enter the contents induction portion from the enlarged-diameter portion through the step connection portion.

In the case of contents which are not an oblong tablet-shaped solid rather a flat tablet-shaped solid, when a path on which the contents slide toward the passage device is curved, the solid may be made to stand and enter the contents induction portion such that a passage of a fixed quantity thereof may not be easily performed. Accordingly, since it is necessary to provide an even sliding bottom in a section in which the flat solid slides, inner walls of the contents induction portion and the container body corresponding to the sliding bottom on which the contents slide to enter the contents induction portion are connected with no curve or with a minimum curve.

In the case of an injection-blown container, the contents induction portion needs a space without a curve for disposing the passage movement portion in order to insert the passage device into the container. The shape change portion may extend in a circumferential direction of the container body to ensure an available space into which the passage device is inserted.

One aspect of the present invention provides a value which is a passage device inducing contents to pass through and includes a passage operation portion which passes the contents. The passage operation portion includes a contents passage means which allows the contents to move.

The contents passage means includes the passage movement portion which passes the contents by movement.

The contents may be induced to move by a modification of the contents passage means caused by tilting or shaking of the passage operation portion.

The movement guide portion which guides movement of contents when the passage operation portion tilts may be included. The contents may be guided to pass through along a surface of the movement guide portion due to a weight or inertia of the contents while the movement guide portion tilts.

When the passage operation portion tilts or moves, the passage movement portion may move due to at least one of a weight of the passage movement portion, inertia of the passage movement portion, and a force of the contents pushing on the passage movement portion.

The passage movement portion may include the opening member which moves in the same direction in which the contents pass through and allows the passage of the contents.

The passage movement portion may include a blocking member which moves separately from the opening member in conjunction with the opening member and blocks at least a part of the opening member so as to allow the contents not to pass through or to partially pass through.

The passage movement portion may include a passage compartment portion provided between the opening member and the blocking member.

The passage movement portion may include a position of the center of gravity of a movement portion of the passage movement portion and a position of a rotational center of the movement portion which is a center of rotational movement of the passage movement portion and the positions differing from each other.

The passage operation portion may include the opening portion to pass the contents. When the passage operation portion tilts or moves, the passage movement portion may not rotate or may be suppressed from rotating for being opened to allow the contents to pass through the opening portion by only a weight of the passage movement portion.

The passage movement portion may not open the opening portion to a degree which allows the contents to pass therethrough by the weight of the passage movement portion before the contents resist the passage movement portion and open the opening portion.

The opening member may move to be opened due to the weight thereof or a pushing force of the contents and may guide the contents to pass through.

One aspect of the present invention provides a contents movement device including a passage device provided in the contents movement device which stores contents and configured to induce the contents to pass therethrough and a housing with at least one side being opened. Here, the passage device includes a passage operation portion for passing the contents, and the passage operation portion includes a contents passage means which allows the contents to move.

The contents passage means may include the passage movement portion which forms a passage space for the contents by movement.

In the passage operation portion, the contents may move due to the modification of the contents passage means caused by tilting or shaking of the passage operation portion.

The movement guide portion which guides movement of contents when the passage operation portion tilts may be included. The contents may be guided to pass through along a surface of the movement guide portion due to a weight or inertia of the contents while the movement guide portion tilts.

When the passage operation portion tilts or moves, the passage movement portion may move due to at least one of a weight of the passage movement portion, inertia of the passage movement portion, and a force of the contents pushing on the passage movement portion.

The passage movement portion may include the opening member which moves in the same direction in which the contents pass through and allows the passage of the contents.

The passage movement portion may include a blocking member which moves separately from the opening member in conjunction with the opening member and blocks at least a part of the opening member so as to allow the contents not to pass through or to partially pass through.

The passage movement portion may include a position of the center of gravity of a movement portion of the passage movement portion and a position of a rotational center of the movement portion which is a center of rotational movement of the passage movement portion and the positions differing from each other.

The passage operation portion may include the opening portion to pass the contents. When the passage operation portion tilts or moves, the passage movement portion may not rotate or may be suppressed from rotating for being opened to allow the contents to pass through the opening portion by only a weight of the passage movement portion.

The passage movement portion may not open the opening portion to a degree which allows the contents to pass therethrough by the weight of the passage movement portion before the contents resist the passage movement portion and open the opening portion.

The opening member may move to be opened due to the weight thereof or a pushing force of the contents and may guide the contents to pass through.

One aspect of the present invention provides an accommodation device including a passage device provided in the accommodation device which stores contents and configured to induce the contents to pass therethrough and a housing which has at least one open side. Here, the passage device includes a passage operation portion for passing the contents, and the passage operation portion includes a contents passage means which allows the contents to move.

One aspect of the present invention provides a contents device including a passage device which includes contents and induces the contents to pass therethrough and a housing which has at least one open side. Here, the passage device includes a passage operation portion for passing the contents, and the passage operation portion includes a contents passage means which allows the contents to move.

A sensing portion which senses a passage of contents when the contents pass through the contents passage means may be included.

The sensing portion may sense or measure at least one of a number, data, weekday, and time when the contents pass through.

Contents measurement of the sensing portion may be performed by an electronic sensor or a mechanical operation.

A display portion which displays data obtained by sensing and measuring of the sensing portion or whether the contents pass through the passage operation portion due to an operation of the contents passage means, to be recognized by using at least one of user sensing methods such as senses of sight, hearing, and touch may be included.

A communication portion which transmits the data obtained by sensing or measuring of the sensing portion may be included.

The sensing portion may include includes at least one type of sensing equipment such as a touch sensor, an acceleration sensor, an angular speed sensor, a gravitational sensor, a terrestrial magnetism sensor, a gyroscope sensor, a proximity sensor, an operation-recognition sensor, an electronic compass, a magnetometer sensor, and a gesture sensor.

A control portion which restricts a contents movement operation of the contents passage means when the sensing portion senses that a fixed quantity of the contents pass through the contents passage means for a certain period or time or senses that contents more than the fixed quantity pass through the contents passage means may be included.

The display portion may display at least one of numbers, letters, symbols, Braille, light emission, lighting, and colors.

Whether the contents pass or a passage quantity sensed by the sensing portion may be determined, and the determined whether the contents pass or the passage quantity or the determined whether the contents pass or the passage quantity with at least one of a date, a weekday, a time of passage may be displayed by the display portion.

Whether the contents pass or a passage quantity sensed by the sensing portion may be determined, and the determined whether the contents pass or the passage quantity or the determined whether the contents pass or the passage quantity with at least one of a date, a weekday, a time of passage may be closely or remotely transmitted through the communication portion.

A locking portion may be included so as to not pass further contents when the sensing portion senses the contents which pass through the contents passage means and it is determined that the fixed quantity of contents have passed.

The locking portion may be provided in the passage device to prevent movement of the contents passage means or to block a movement path of the contents in the passage operation portion.

The display portion may display at least one of numbers, letters, symbols, and signals by using a liquid crystal display (LCD) or a light emitting diode (LED).

A locked state may be maintained before a designated time or an end of a situation when control is necessary such as a case of medication which should be restricted in a dose, or foodstuffs which should be restricted in intake of an ordinary person.

The blocking of movement in the contents passage means may be performed by resisting contact with a moving part of the contents passage means, and the movement path in the passage operation portion may be blocked by blocking or resisting the contents at the passage path portion provided at a passage entry side and a passage discharge side of the contents.

At least one of numbers, letters, and symbols may be displayed on a surface of the contents or inside the contents such that it is possible to observe a display about the contents which have passed through the contents passage means or the contents which have not passed through the contents passage means.

At least one of numbers, letters, and symbols may be displayed on a surface of the contents or inside the contents such that it is possible to observe a display about the contents which have passed through the contents passage means or the contents which have not passed through the contents passage means.

The contents device may be at least one of a game device, a board game device, a toy device, and a learning device.

One aspect of the present invention provides a medication-taking management device including a passage operation portion which discharges contents in a housing of an accommodation device through a passage space and a sensor module which senses the contents discharged by the passage operation portion.

The sensor module may include a sensor portion which senses contents which pass through the passage space and a sensing control portion which controls the sensor portion to sense the contents which pass through the passage space, generates medication-taking state information according to a result of sensing, and transmits the medication-taking state information to a medication-taking guide terminal.

The sensing control portion may emit light toward the passage space by using the sensor portion and may sense the contents on the basis of the light reflected by the contents discharged through the passage space.

The sensing control portion may sense the contents through the passage space by using a time difference between a time of emitting the light and a time of receiving the light through the sensor portion.

The sensing control portion may determine that the contents pass through the passage space when the time difference is within a preset set value.

One aspect of the present invention provides a medication-taking management device including an output portion and a medication-taking guide terminal control portion which receives medication-taking state information from a sensor module, receives medication-taking schedule information from a medication-taking management server, generates medication-taking management information for a user by using the medication-taking schedule information and the medication-taking state information, and outputs the medication-taking management information to the output portion.

The medication-taking state information may include at least one of contents information, whether the contents are sensed, and time information of sensing the contents.

The medication-taking schedule information may include at least one of contents information, a medication-taking time, a medication-taking interval, and a dosage for each type of contents.

The medication-taking guide terminal control portion may output at least one of the contents information and the dosage for each type of contents through the output portion according to at least one of the medication-taking time and the medication-taking interval.

The medication-taking guide terminal control portion may compare the medication-taking schedule information with the medication-taking state information and may warn of abuse or misuse of medication according to a result of comparing.

The medication-taking guide terminal control portion may generate medication-taking history information by accumulating the medication-taking state information.

One aspect of the present invention provides a medication-taking management device including a medication-taking schedule information generation portion which generates medication-taking schedule information and a control server which transmits the medication-taking schedule information stored in the medication-taking schedule information storage portion to a user terminal.

The medication-taking schedule information may include at least one of contents information, a medication-taking time, a medication-taking interval, and a dosage for each type of contents.

The medication-taking schedule information generation portion may generate the medication-taking schedule information by using prescription information of a user.

As described above, according to embodiments of the present invention, unlike conventional technologies, a passage device, a valve, an accommodation device including the same, a contents movement device, and a contents device may discharge a fixed quantity or a demanded quantity of solid, powder, or liquid contents and includes an opening member for blocking contents passage sides of the accommodation device, the contents movement device, and the contents device so as to stably induce a passage of the demanded quantity of the contents.

According to the embodiments of the present invention, a movement angle of the opening member which opens the contents passage sides of the accommodation device, the contents movement device, and the contents device is restricted such that opening or closing responsibility may be increased.

According to the embodiments of the present invention, a standby accommodation portion of contents is provided by varying a passage space such that it is possible to stably induce the passage of the fixed quantity of the contents.

According to the embodiments of the present invention, since the passage space for the contents is provided and closed, interconnecting the passage of the fixed quantity of the contents, not to allow the contents to pass through the passage space, it is possible to prevent a passage of an excessive quantity of the contents.

According to the embodiments of the present invention, movement caused by an own weight is controlled by a balancing action using a weight of the passage movement portion and a gravitational center position such that a needed quantity of contents may pass by allowing the passage space not to be closed until the needed quantity of contents pass.

MODE FOR INVENTION

Hereinafter, embodiments of a passage device, a valve, and an accommodation device including the same, a contents movement device, and a contents device will be described with reference to the attached drawings. In this process, a thickness of lines, a size of a component, or the like shown in the drawings may be exaggerated for clarity and convenience of description. Also, the following terms are defined in consideration of functions thereof in the present invention and may vary according to the intention of a worker or an operator or practice. Accordingly, definitions of the terms will be determined on the basis of the content throughout the specification.

Figure 2:
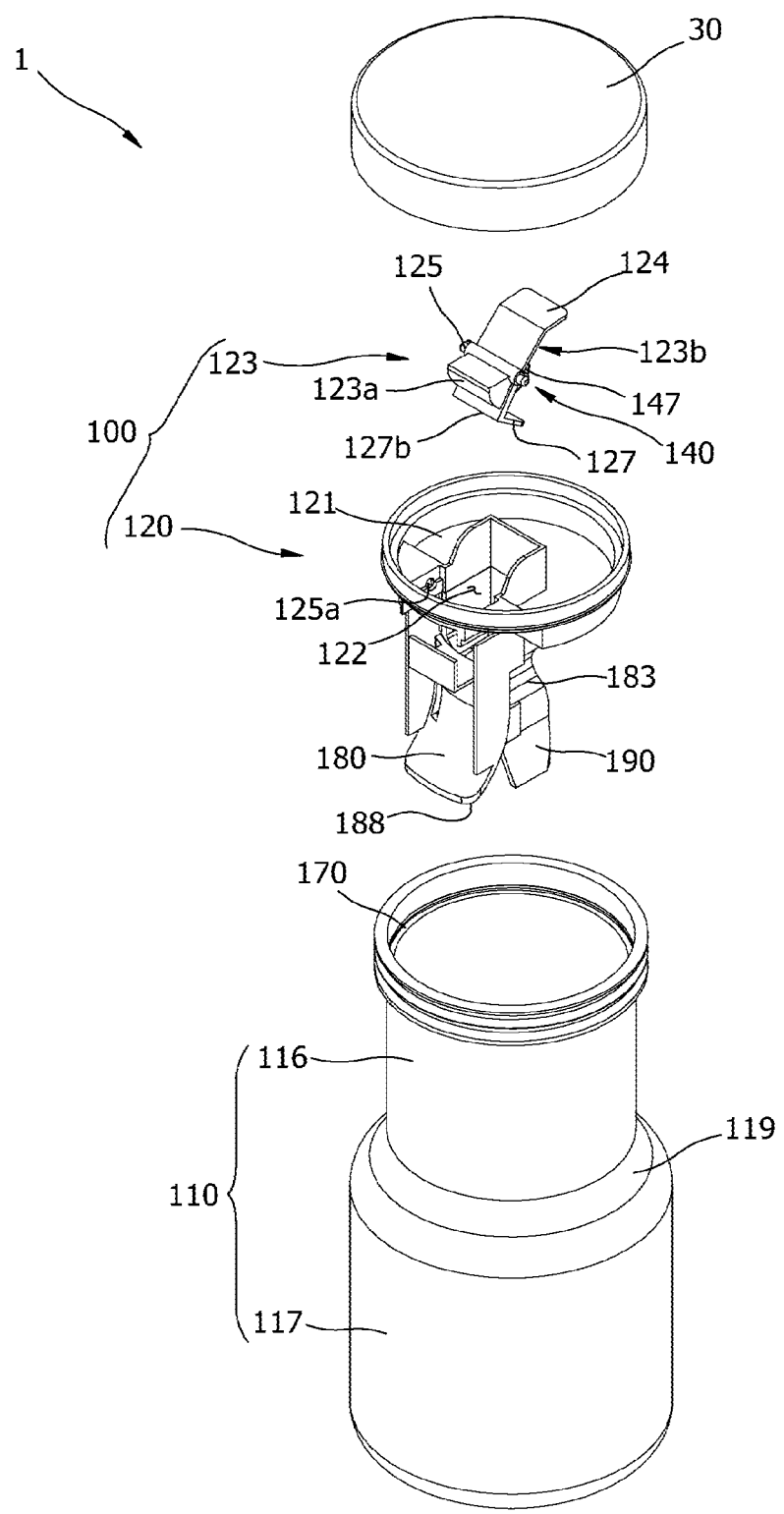
FIG. 2 is an exploded perspective view of the contents movement device including the passage device according to the first embodiment of the present invention.

FIG. 1 is a perspective view of a contents movement device including a passage device according to a first embodiment of the present invention, and FIG. 2 is an exploded perspective view of the contents movement device including the passage device according to the first embodiment of the present invention.

Figure 3:
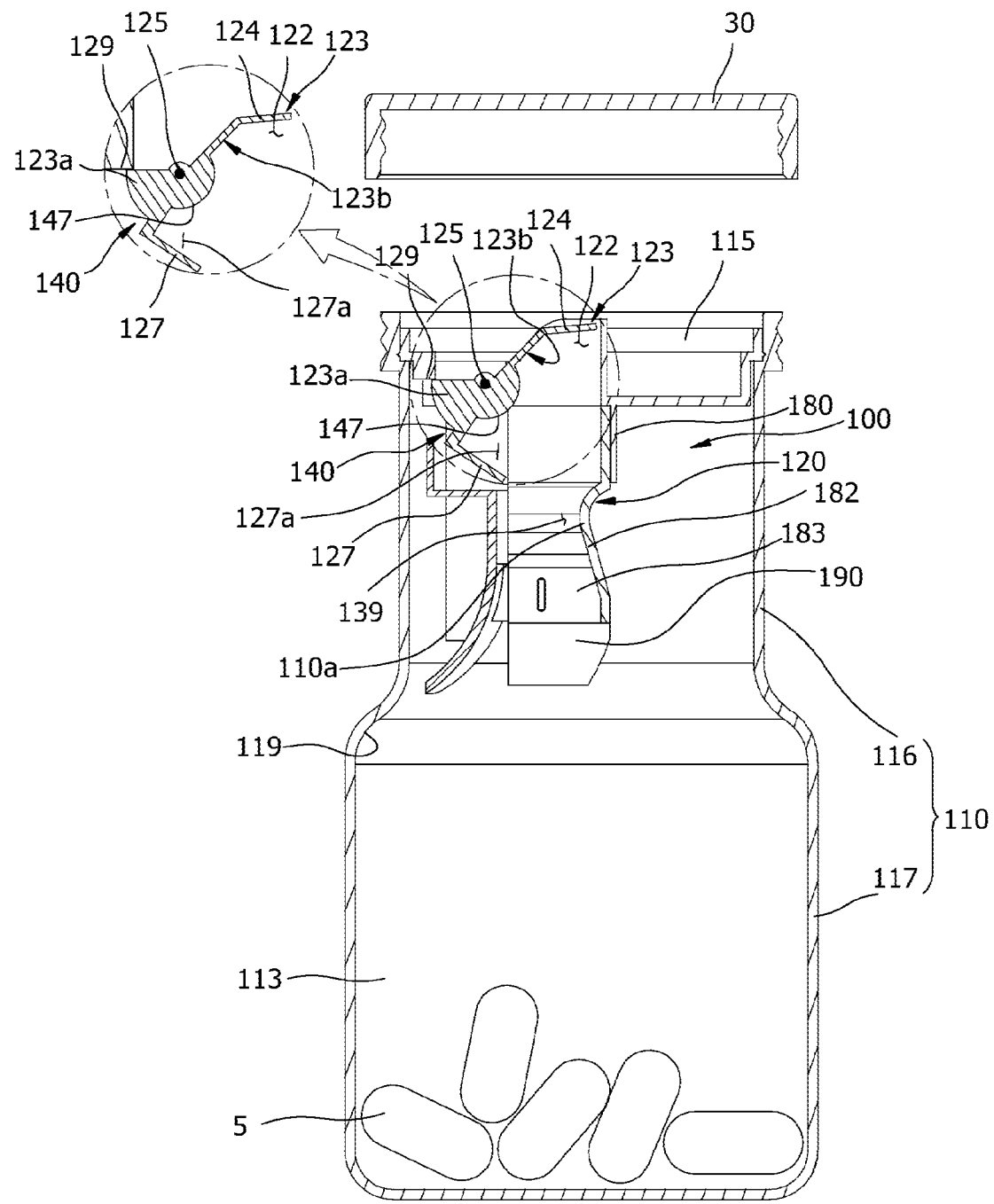
FIG. 3 is a side cross-sectional view of the contents movement device including the passage device according to the first embodiment of the present invention.
Figure 4:
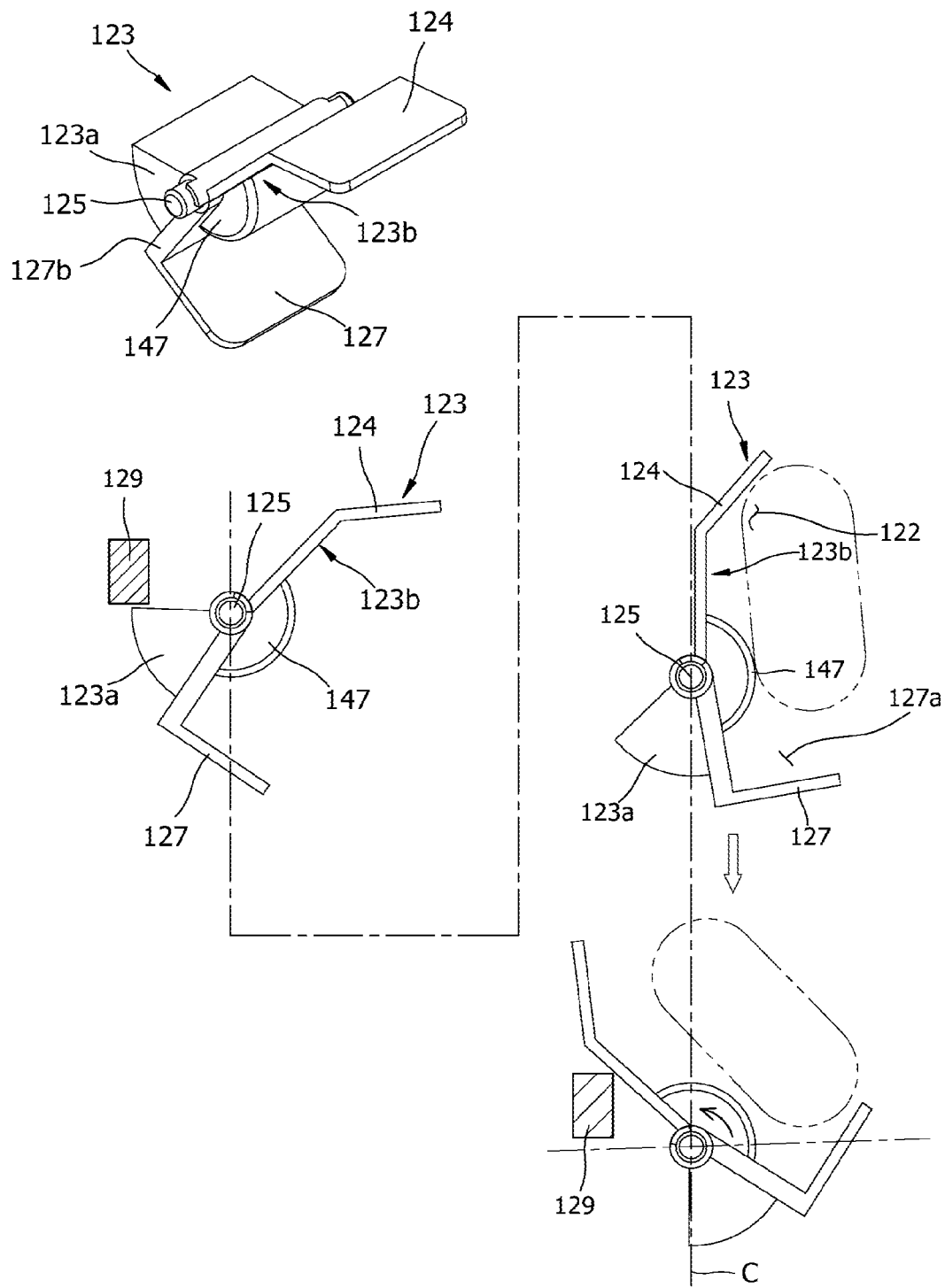
FIG. 4 is a main part view illustrating a tilting state of the passage device according to the first embodiment of the present invention.
Figure 5:
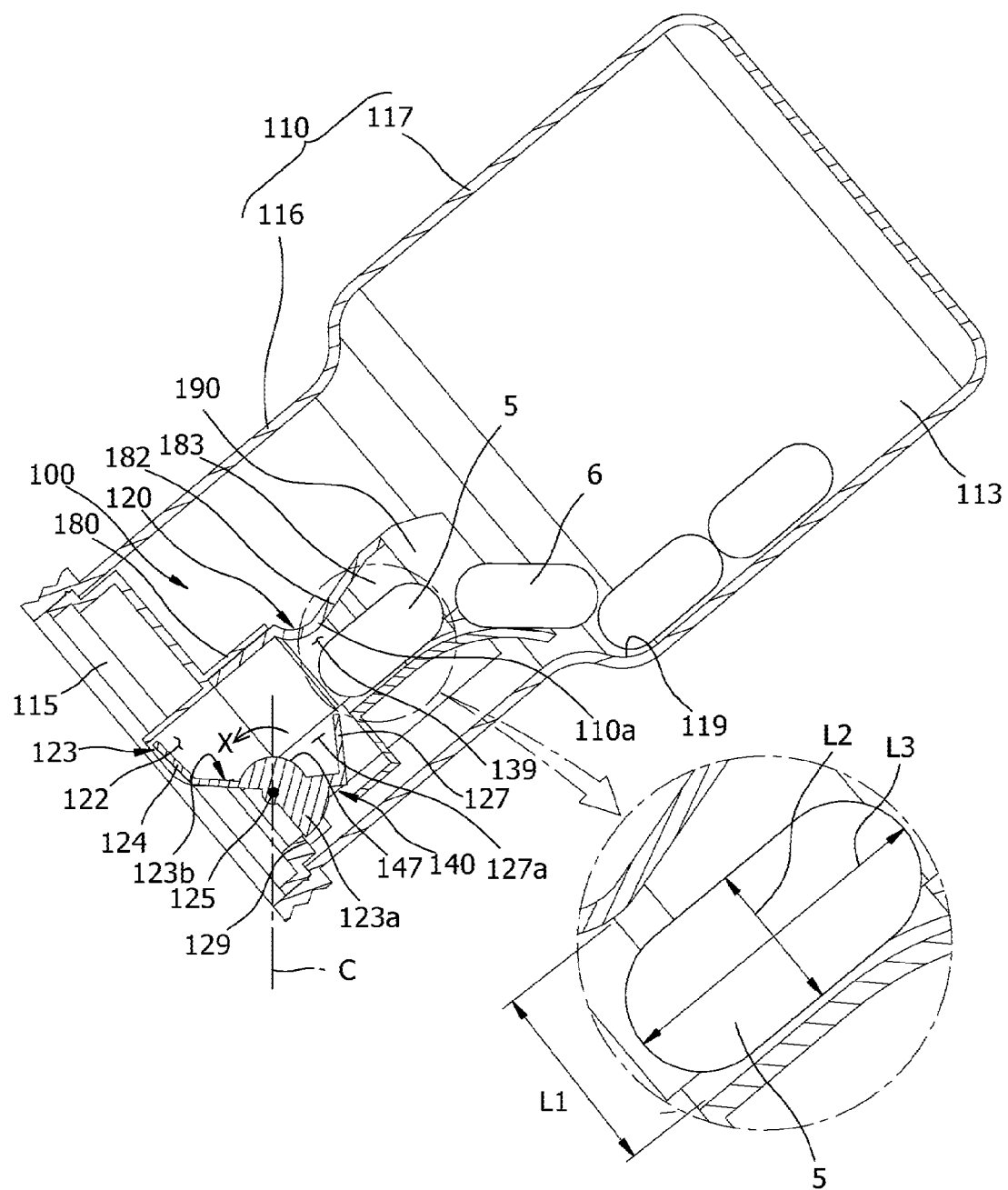
FIG. 5 is a cross-sectional view illustrating a state in which a contents passage means remains in an initial state when a housing of the contents movement device including the passage device tilts according to the first embodiment of the present invention.
Figure 6:
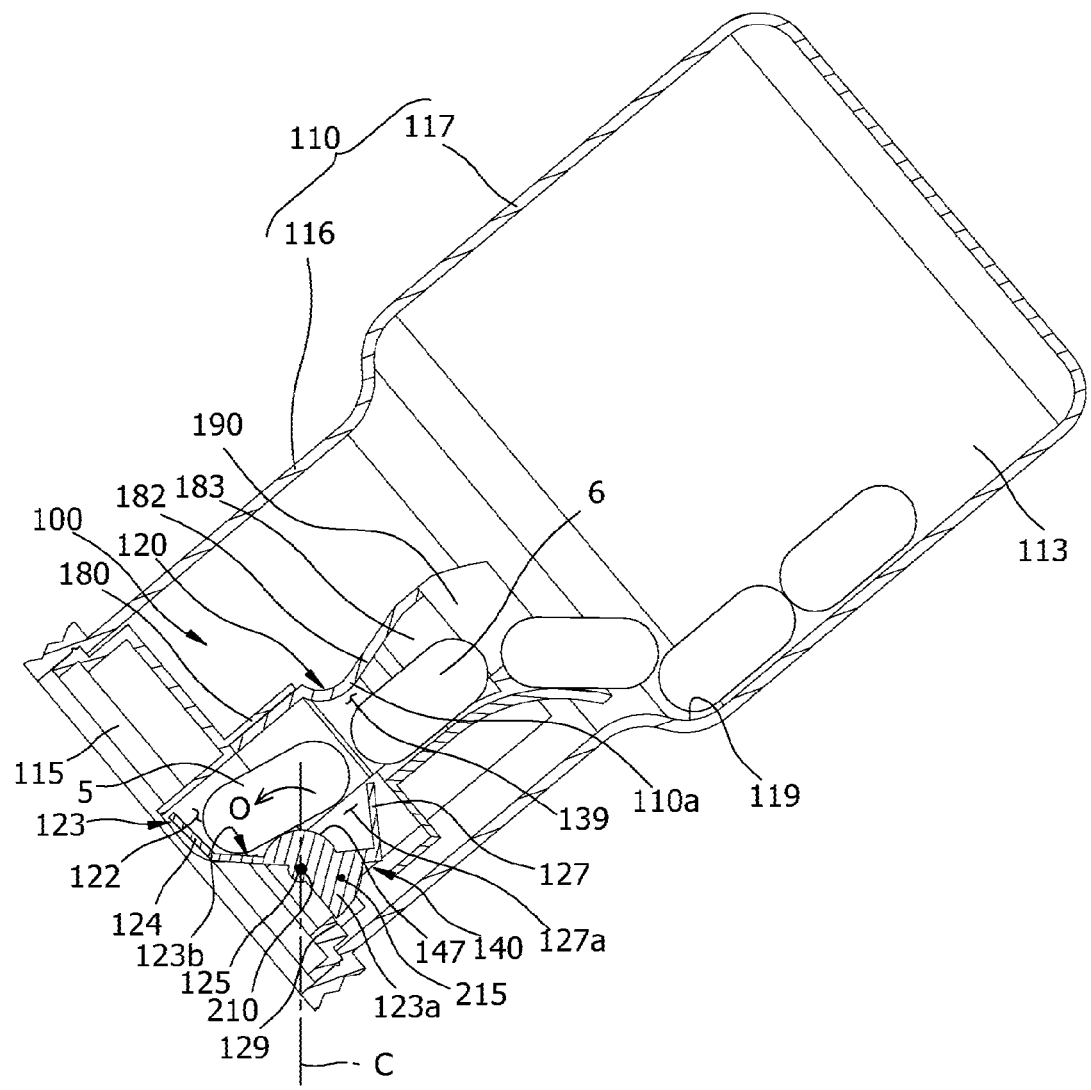
FIG. 6 is a cross-sectional view illustrating a state in which movement of the contents passage means is started by a pulling force of contents according to the first embodiment of the present invention.

FIG. 3 is a side cross-sectional view of the contents movement device including the passage device according to the first embodiment of the present invention, FIG. 4 is a significant part view illustrating a tilting state of the passage device according to the first embodiment of the present invention, FIG. 5 is a cross-sectional view illustrating a state in which a contents passage means remains in an initial state when a housing of the contents movement device including the passage device tilts according to the first embodiment of the present invention, and FIG. 6 is a cross-sectional view illustrating a state in which movement of the contents passage means is started by a pulling force of contents according to the first embodiment.

Figure 7:
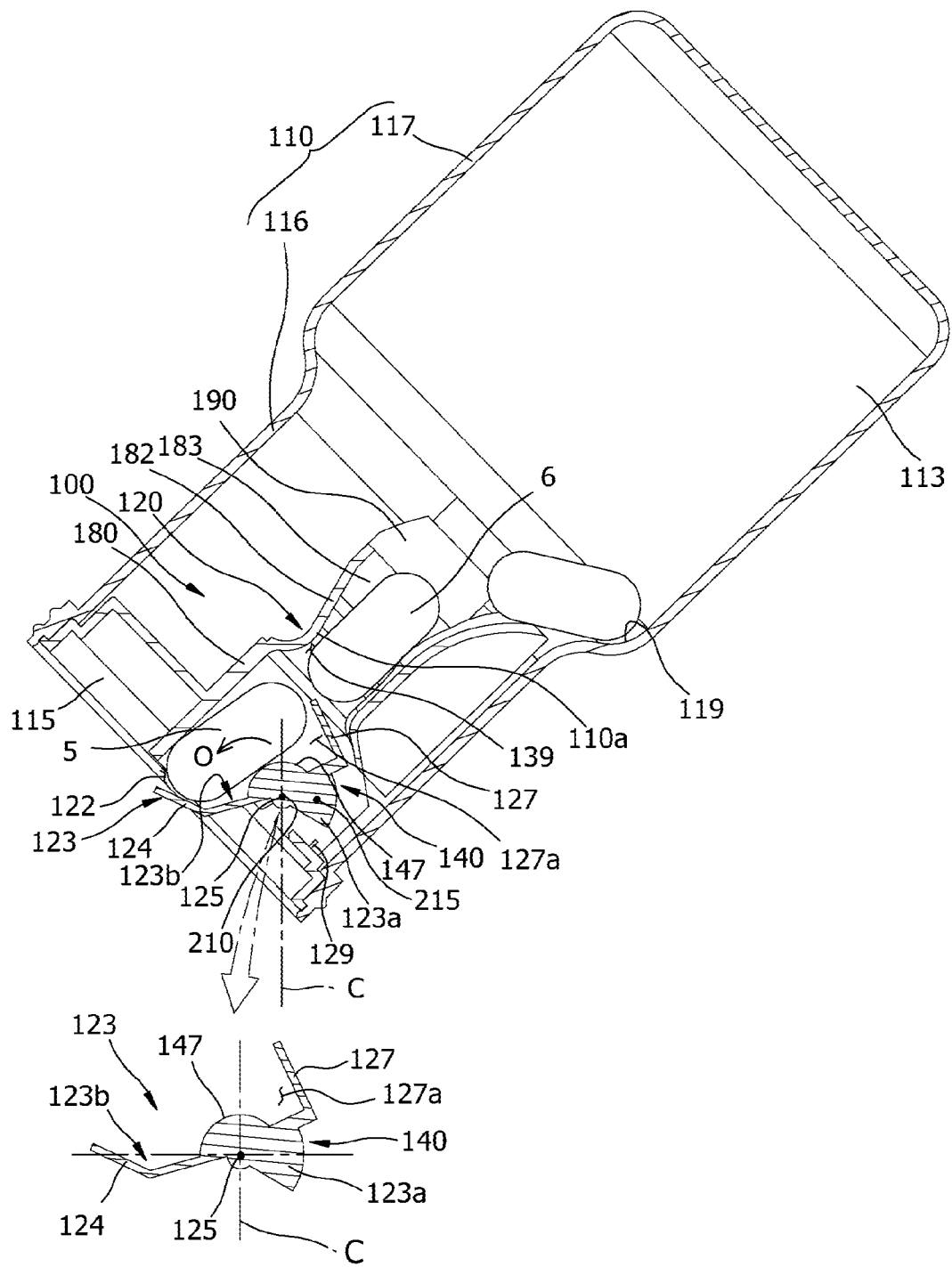
FIG. 7 is a cross-sectional view illustrating a state in which the contents passage means moves due to the pulling force of contents according to the first embodiment of the present invention.
Figure 8:
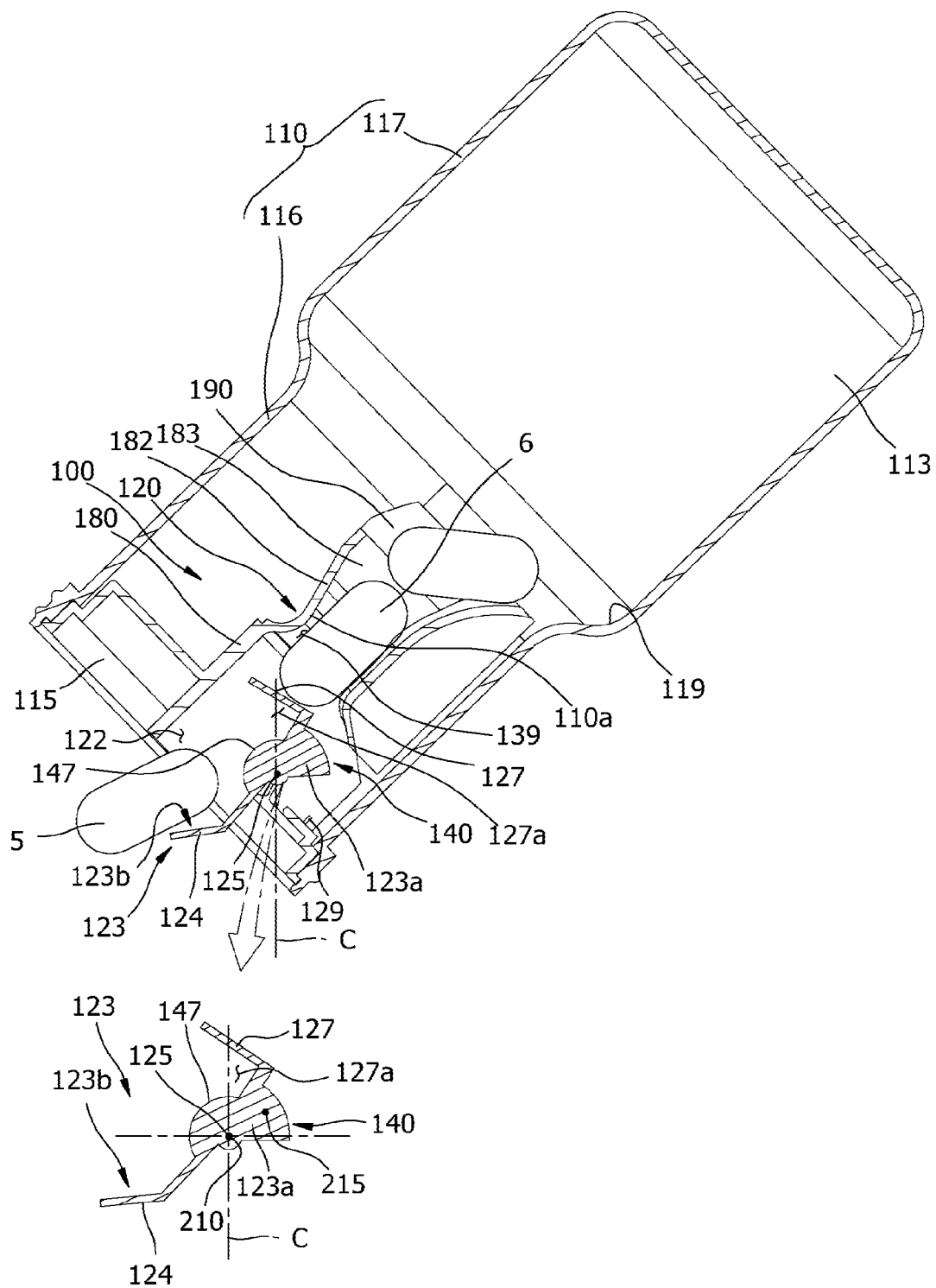
FIG. 8 is a cross-sectional view illustrating a state in which the contents passage means moves due to the pulling force of contents according to the first embodiment of the present invention.

FIG. 7 is a cross-sectional view illustrating a state in which the contents passage means moves due to the pulling force of contents according to the first embodiment of the present invention, and FIG. 8 is a cross-sectional view illustrating a state in which the contents passage means moves due to the pulling force of contents according to the first embodiment.

Figure 9:
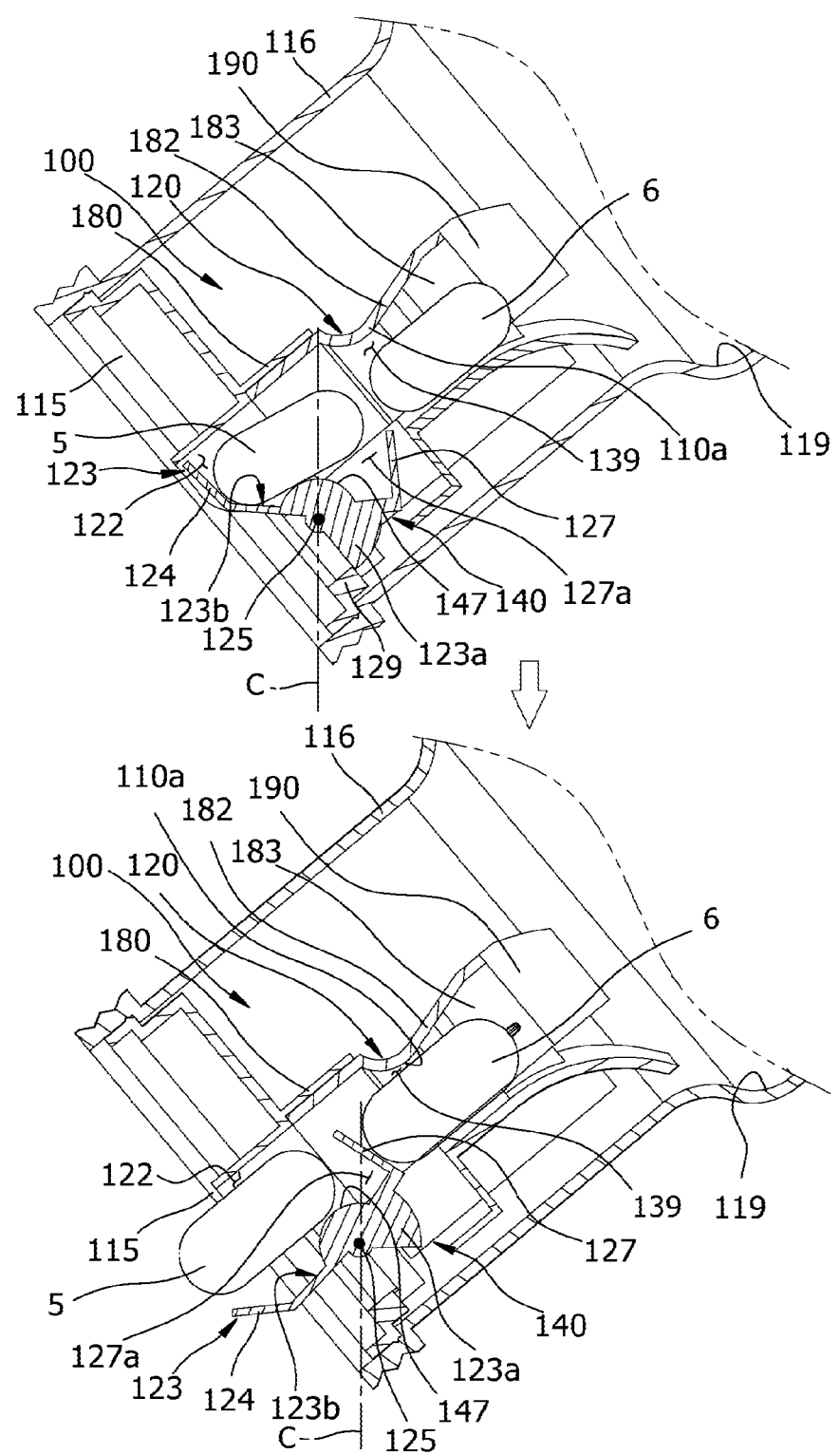
FIG. 9 is a cross-sectional view illustrating a state in which the contents movement device including the passage device is used according to the first embodiment of the present invention.
Figure 10:
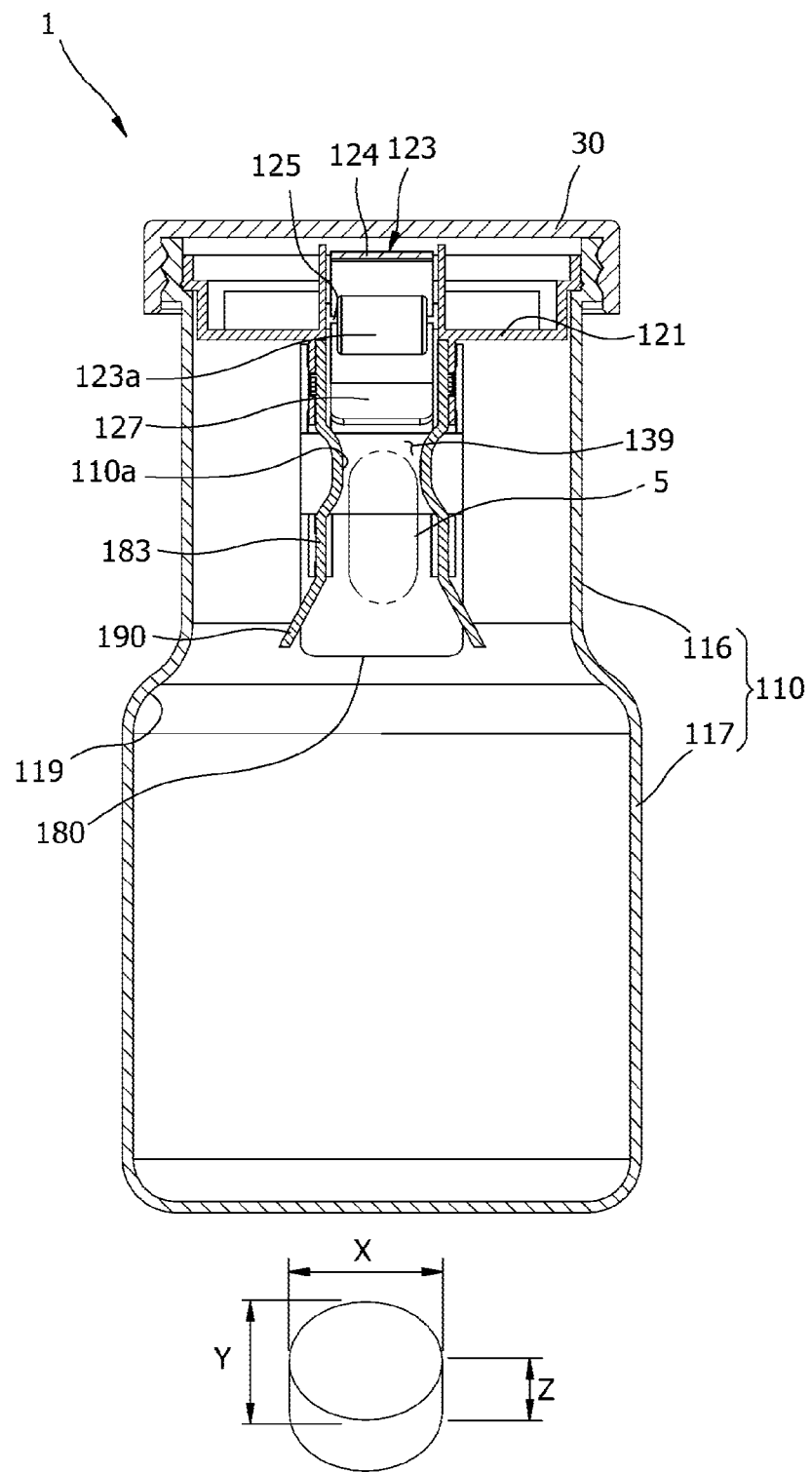
FIG. 10 is a front cross-sectional view of the contents movement device including the passage device according to the first embodiment of the present invention.
Figure 11:
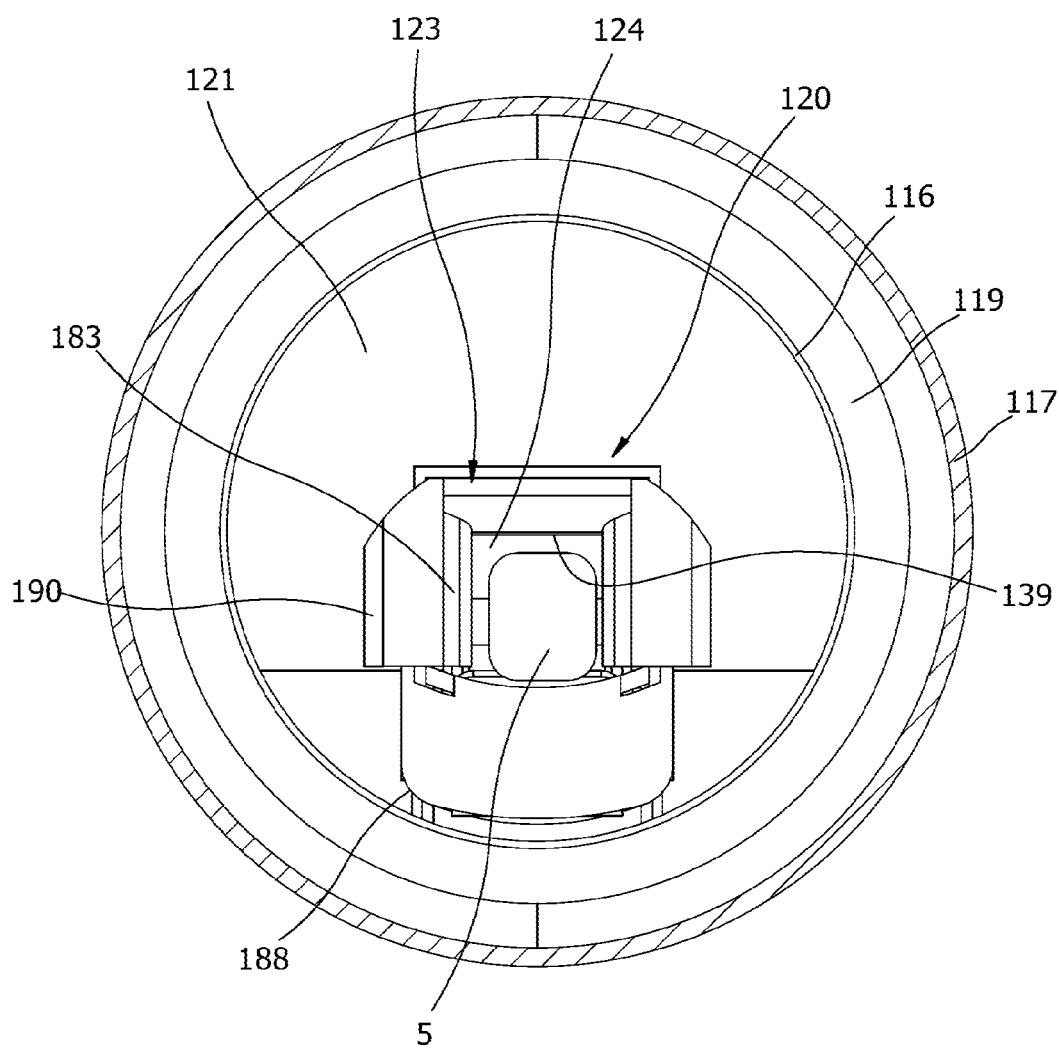
FIG. 11 is a bottom cross-sectional view of the contents movement device including the passage device according to the first embodiment of the present invention.
Figure 12:
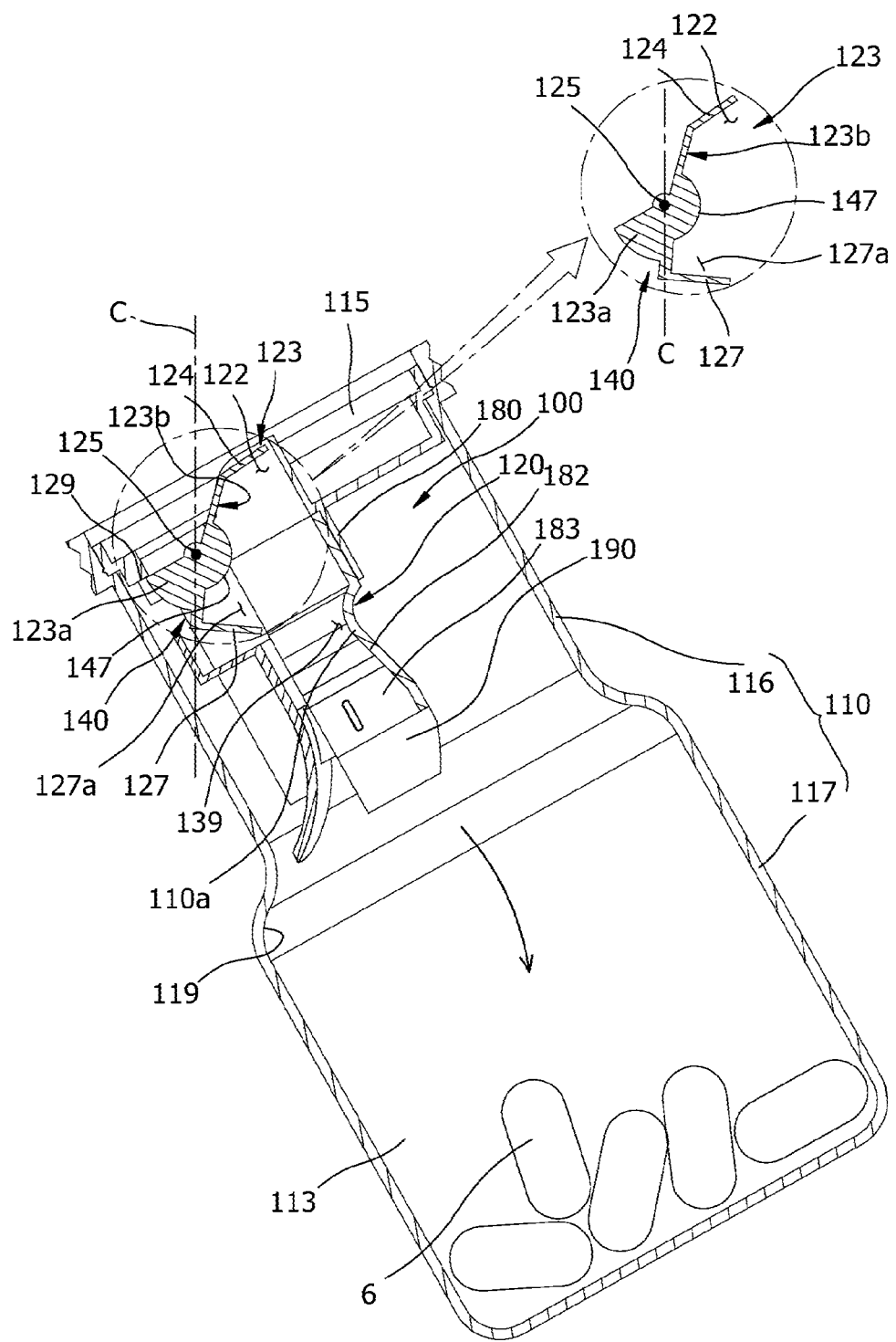
FIG. 12 is a cross-sectional view illustrating a state in which the contents movement device including the passage device returns to an initial state after being used according to the first embodiment of the present invention.

FIG. 9 is a cross-sectional view illustrating a state in which the contents movement device including the passage device is used according to the first embodiment of the present invention, FIG. 10 is a front cross-sectional view of the contents movement device including the passage device according to the first embodiment of the present invention, FIG. 11 is a bottom cross-sectional view of the contents movement device including the passage device according to the first embodiment of the present invention, and FIG. 12 is a cross-sectional view illustrating a state in which the contents movement device including the passage device returns to an initial state after being used according to the first embodiment of the present invention.

As shown in FIGS. 1 to 12, a contents movement device 1 including a passage device 100 according to the first embodiment of the present invention includes a housing 110, a passage operation portion 120, and a supply guide portion 119.

The housing 110 is a container which stores contents 5 and includes the passage operation portion 120 therein so as to form the supply guide portion 119.

Here, the contents 5 are a material capable of passing through a contents passage means 123 such as solid matter, powder, a liquid, or the like.

Here, the housing 110 forms a passage-anterior portion 113 which is a part anterior to the passage operation portion 120 and stores the corresponding contents 5. Additionally, the housing 110 may form a standby storage portion 115 in a space after the contents 5 pass through the passage operation portion 120.

That is, the passage-anterior portion 113 is a space in the housing 110 which stores the contents 5, and the standby storage portion 115 means a space or an open side where the contents 5 are in waiting to be withdrawn.

The passage-anterior portion 113 and the standby storage portion 115 are partially connected to each other through an opening portion 122 formed in the passage operation portion 120, whereby the contents 5 of the passage-anterior portion 113 may move to the standby storage portion 115 through the opening portion 122.

Accordingly, the passage operation portion 120 is provided in the housing 110 and guides movement of the contents 5. The passage operation portion 120 performs a function of inducing movement of a fixed quantity or a demanded quantity of the contents 5. Here, "the fixed quantity" means the same number or quantity and a quantity or number of different movements within a permissible range. "The demanded quantity" is a quantity (number) needed by a user and is included within the range of "the fixed quantity."

Particularly, the passage operation portion 120 includes a contents passage means 123 and a passage path portion 139.

The contents passage means 123 performs a function of allowing the contents 5 to be passed from the passage-anterior portion 113 to the standby storage portion 115.

Particularly, the contents passage means 123 includes a passage movement portion 140.

The passage movement portion 140 performs a function of being opened by movement to allow the contents 5 to pass therethrough.

That is, the passage movement portion 140 interconnects to an opening member 124 and closes the opened opening portion 122. Here, the passage movement portion 140 includes a blocking member 127 and the opening member 124.

For example, in one embodiment in which a fixed quantity of contents is one, when one piece of the contents 5 passes through a front of the passage path portion 139, another piece of the contents 5 passes through a rear of the passage path portion 139 while adjacently behind the front-passing contents 5 and the rear-passing contents 5 moves and comes into contact with the blocking member 127.

Here, the blocking member 127 may be formed to be bent, and a blocking member bent portion 127b of the blocking member 127 may be linearly bent or formed to be a curved surface.

An angle of the blocking member bent portion 127b formed by bending the blocking member 127 may be a steep tilt close to a right angle so as to not allow the contents except the demanded quantity to enter the passage operation portion 120. Of course, the blocking member bent portion 127b may be bent at a variety of angles.

Afterwards, the blocking member 127 at least partially blocks the opening portion 122 such that the contents 5 may be prevented from moving more than the fixed quantity into the opening portion 122.

Particularly, as shown in FIG. 3, in an initial state in which the housing 110 stands on the floor, an action of equiponderance force of the passage movement portion 140 or the passage movement portion 140 may maintain, by using a stopper 129, a state in which the opening member 124 blocks the opening portion 122.

That is, as shown in FIG. 3, although a force of rotating the passage movement portion 140 clockwise on the basis of a movement member 125 is applied by a weight of the opening member 124, the stopper 129 prevents the passage movement portion 140 from rotating clockwise.

In a general container storage state in which the housing 110 stands, the opening member 124 blocks the opening portion 122 such that foreign materials such as air, dust, or the like may be prevented from moving into the housing 110 through the opening portion 122.

In addition, as shown in FIG. 3, in the initial state in which the housing 110 stands (in a state of rotating at 0 degree), a rightward weight-leaning action of the passage movement portion 140 to rotate clockwise by an action of a force to move to a weight-balanced state is suppressed by the stopper 129 to remain in the weight-balanced state (a stationary state). Particularly, when the passage movement portion 140 is in the rightward weight-leaning state, the stopper 129 at a top end of a left side suppresses clockwise rotation of the passage movement portion 140.

Of course, the stopper 129 may change to a variety of shapes and positions.

FIG. 4 illustrates a state of the passage movement portion 140 as the housing 110 tilts to guide a passage of the contents 5. Particularly, the passage movement portion 140 pivots (moves) bidirectionally on the basis of the movement member 125 as a criterion.

Also, FIG. 5 illustrates a state of the passage movement portion 140 when the housing 110 tilts at 135 degrees counterclockwise from the initial state.

That is, when the housing 110 tilts at 135 degrees counterclockwise, the housing 110 tilts leftward (on the basis of the movement member 125) in a direction in which the passage movement portion 140 is located. However, since the housing 110 tilts while not more than horizontality (−90 degrees), the contents 5 change to a state of not being slidable.

A tilting angle of the housing 110 is not limited. In addition, a perpendicularly downward direction of a rotating shaft 125 of the passage movement portion 140 indicates a gravitational direction. Although, on the basis of a perpendicular direction C, a weight of a right side is greater such that a force of the passage movement portion 140 to rotate rightward is generated, a substantial rotation does not occur due to the stopper 129.

That is, since the right side of the perpendicular direction C is heavier when the housing 110 is horizontal (−90 degrees), a force is generated to cause the passage movement portion 140 to rotate rightward, that is, clockwise. However, the substantial rotation does not occur due to the stopper 129. Accordingly, the housing 110 rotates along an axis of a wrist without rotation of the passage movement portion 140 as much as the rotation on the basis of the axis of wrist.

The passage movement portion 140 moves corresponding to movement caused by a gravitational action to the contents and opens the passage operation portion 120 to allow the contents to pass. When the passage operation portion 120 tilts or moves, the passage movement portion 140 may move by at least one among a weight of the passage movement portion 140, inertia of the passage movement portion 140, and a force of the contents pressing the passage movement portion 140.

Rotational movement of the passage movement portion 140 which passes the contents, as shown in FIGS. 6 to 8, is performed by gravitational movement of the contents or transmission of a movement force of the contents to the passage movement portion 140, which is caused by a position of a movement portion rotational center 210 which is a central axis of the rotational movement of the passage movement portion 140 and is located in a downward direction which is a gravitational direction or an operation of the passage operation portion 120 by tilting, being turned over, or shaken.

Also, the rotational movement of the passage movement portion 140 may be formed of a movement force caused by a weight of the contents pushing the contents passage means 123.

When a position of a movement portion gravitational center 215 of the passage movement portion 140 is located in a direction opposite an external passage direction of the passage device 100, which is behind a position of the movement rotational center 210 of the passage movement portion 140, such that, as shown in FIG. 5, the position of the movement portion rotational center 210 which is a rotational movement center of the passage movement portion 140 is located in the downward direction which is the gravitational direction and the passage operation portion 120 tilts, the rotational movement of the passage movement portion 140 may be suppressed or delayed by a difference between the positions of the movement portion weight center 215 and the movement portion rotational center 210.

In addition, the passage path portion 139 performs a function of restricting a movement amount of the contents 5 which move toward the contents passage means 123.

In detail, in the passage path portion 139, when a length between ends of one side of a piece of the contents 5 differs from a length between ends of the other side thereof, a minimum inner diameter L1 of a path width which is a minimum length inner diameter of an inner space of the passage path portion 139 is less than or equal to two times of a maximum outer diameter L2 of the piece of the contents 5 in a widthwise direction, which is a maximum outer length of the piece of the contents 5 in the widthwise direction, such that two or more pieces of the contents 5 can not enter or pass through the passage path portion 139 at the same time and only one piece of the contents 5 may enter or pass through the passage path portion 139 at once.

Also, when the length between the ends of one side of the piece of the contents 5 which passes through the passage path portion 139 differs from the length between the ends of the other side thereof, the passage path portion 139 guides the contents 5 to pass through the passage path portion 139 in a longitudinal direction L3 of lengthwise ends.

The contents passage means 123 includes the blocking member 127 which interconnects to the opening member 124 and closes the open opening portion 122. When one piece of the contents 5 passes through the front of the passage path portion 139, another piece of the contents 5 passes through the rear of the passage path portion 139 while adjacently behind the front-passing contents 5, and the rear-passing contents 5 moves and comes into contact with the blocking member 127 such that the blocking member 127 at least partially blocks the opening portion 122 so as to prevent the contents 5 which exceed the fixed quantity from unnecessarily moving into the opening portion 122.

In the embodiment, to allow the fixed quantity of pieces of the contents 5 to enter a position of the opening member 124 is present, before the contents 5 come into contact with the opening member 124, the opening member 124 is in a closed state and the blocking member 127 is in an open state as shown in FIG. 5 due to a weight-balancing force of the passage movement portion 140 and they remain in those states until the fixed quantity of the contents 5 enters the passage operation portion 120.

Also, when the fixed quantity of the contents 5 come into contact with the opening member 124, as shown in FIGS. 7 and 8, the opening member 124 and the blocking member 127 interconnect with each other and rotate together such that the opening member 124 changes to an open state and the blocking member 127 changes to a closed state. Here, according to the closed state of the blocking member 127, the contents 5 in addition to the fixed quantity thereof may be prevented from continuously entering the opening portion 122.

The passage movement portion 140 is pivotably provided in a fixing member 121 corresponding to an inner surface of the opening portion 122. The opening portion 122 is opened in a sequence shown in FIGS. 6 to 8 through operations of tilting the passage operation portion 120 in a sequence shown in FIGS. 3 to 5 so as to withdraw the contents 5. Then, as shown in FIG. 12, when the passage operation portion 120 returns to a position of standing, due to the weight-balancing force of the passage movement portion 140, the passage movement portion 140 returns to a state in which the blocking member 127 is opened on the basis of the movement member 125 as shown in FIG. 3 or 12.

Accordingly, when the passage operation portion 120 tilts again in a sequence shown from FIG. 3 which is a return position to FIG. 5, another fixed quantity of the contents 5 which firstly accesses the passage movement portion 140 to be withdrawn again may enter the blocking member 127 without blocking and may come into contact with the opening member 124. Due to the above-described pivoting operation of the passage movement portion 140, all the contents 5 in a container body 110 may be withdrawn as much as the fixed quantity of the contents.

A movement guide portion 180 which induces the contents 5 into the passage path portion 139 is provided below the passage path portion 139.

Particularly, at least a part of the movement guide portion 180 is formed to be inclined such that the contents 5 are guided along an inclined surface to a place in which the passage path portion 139 is located.

That is, when the housing 110 which is provided with the passage operation portion 120 tilts, the contents 5 moves along the inclined surface of the movement guide portion 180 in a gravitational direction.

Particularly, the passage operation portion 120 has the opening portion 122 and is formed such that the opening portion 122 rises to a certain height.

In addition, the inclined surface is formed to be at least partially curved and to become gradually narrower such that the contents 5 are induced to move toward the passage operation portion 120 through a curved surface which becomes narrower.

Also, a movement angle of the opening member 124 may be restricted by at least one of the stopper 129 provided in the contents passage means 123 and a cover 30 connected to the housing 110 which includes the passage operation portion 120.

In addition, the stopper 129 extends from the movement member 125 and maintains a state in which the opening member 124 does not move further and the blocking member 127 completely blocks the opening portion 122. That is, the stopper 129 is formed at the contents passage means 123 or the housing 110 and restricts a rotational angle of the opening member 124.

A contents accommodation device 1 which includes the passage device 100 may be a container device.

In more detail, the contents passage means 13 includes the passage movement portion 140 which is opened by moving in order to pass the contents 5.

Also, the passage movement portion 140 includes the opening member 124 configured to move in a passage direction of the contents 5 and to form a passage space for the contents 5 and the blocking member 127 configured to interconnect to the opening member 124 and block at least a part of the opening portion 122 to not allow the contents 5 to pass therethrough or only partially pass therethrough.

Due to this, the blocking member 127 may interconnect to the opening member 124 and at least partially block the opening portion 122 so as to prevent an excessive quantity, which exceeds the fixed quantity, of the contents 5 from passing through the opening portion 122.

Also, the passage operation portion 120 includes the fixing member 121 which includes the opening portion 122 to pass the contents 5 therethrough and the movement guide portion 180 configured to guide the contents 5 to move toward the contents passage means 123.

Here, the contents 5 pass through due to deformation of the contents passage means 123, and more particularly, to pivoting of the opening member 124.

That is, the passage operation portion 120 includes the opening portion 122 connected to the passage-anterior portion 113 in which the contents 5 are located before passage so as to allow the contents 5 located in the passage-anterior portion 113 to pass through. Particularly, the contents passage means 123 moves the contents 5 through the opening portion 122.

In other words, the passage space for the contents 5 may be formed by at least one of an unfixed free end of the opening member 124 being pushed by the weight of the contents 5, shaking of the housing 110 including the passage operation portion 120, and the weight of the opening member 124.

Meanwhile, the passage device 100 may be an opening or closing device which is applied to the contents movement device 1 or accommodation device to be openable or closable from a body of the contents movement device 1 or accommodation device.

Also, the passage device 100 includes the passage operation portion 120. In addition, the passage operation portion 120 guides the contents 5 in the passage-anterior portion 113 of the body of the contents movement device 1 or accommodation device toward the passage device 100. Here, the body of the contents movement device 1 or accommodation device may refer to the housing 110.

In addition, the passage movement portion 140 includes the movement member 125. The movement member 125 may movably connect to the opening member 124.

The passage operation portion 120 includes the passage path portion 139 which extends from a passage discharge side which is a side in contact with the contents passage means 123 toward a passage enter side in which the contents 5 enter.

Also, the passage path portion 139 performs a function of guiding the contents 5 to move toward the contents passage means 123.

In addition, the passage movement portion 140 may include a balancing portion 123*b* configured to suppress the passage movement portion 140 from tilting with the passage operation portion 120 at a tilt which is more than a tilt of the passage operation portion 120 when the passage operation portion 120 tilts.

Through the opening portion 122, the contents 5 are guided to pass depending on whether the passage space formed by the movement of the opening member 124 is open or not. Here, the opening member 124 may be directly or indirectly connected to the fixing member 121.

In other words, when the passage operation portion 120 tilts toward the passage device 100, that is, in a direction in which the contents 5 slide, the weight-leaning force is applied in a direction opposite to the direction in which the passage operation portion 120 tilts such that the passage movement portion 140 suppresses the opening member 124 from tilting at or above an angle at which the passage operation portion 120 tilts, in the direction in which the passage operation portion 120 tilts, due to the weight of the opening member 124.

In addition, the balancing portion 123b is configured to allow the balancing portion 123b in a weight-balanced state to generate a rotational force in a direction opposite a tilting direction of the passage operation portion 120 which tilts to pass the contents 5 through such that a force for not allowing the opening member 124 to tilt in the tilting direction of the passage operation portion 120 and to rotate in the direction opposite the tilting direction of the passage operation portion 120 is applied.

Here, the fixing member 121 may be provided on an inner circumferential surface of an inner through hole space of the passage device 100 to which the opening member 124 is connected or may be a member of the housing 110 included in the passage device 100.

Particularly, when the contents 5 move while being in contact with an external curved surface of the movement member 125 or an outer surface of the opening member 124 in a passage direction or a direction opposite the passage direction, the contents 5 are moved with resistance outward from a circumference of a movement fixing portion 125a.

Here, due to movement of the contents 5 outward from the circumference of the movement fixing portion 125a, an effective passage space of the opening portion 122 becomes narrow and blocks a passage of the contents 5 other than a demanded quantity thereof.

That is, as the passage operation portion 120 tilts, when the contents 5 come into contact with the opening member 124, at least a part or all of the weight of the contents 5 is added to the balancing portion 123b such that weight-leaning of the balancing portion 123b occurs in the tilting direction of the passage operation portion 120. Here, when the weight-leaning of the balancing portion 123b in the tilting direction of the passage operation portion 120, which occurs due to the weight of the contents 5 added to the opening member 124, exceeds a balance-maintaining force of only the balancing portion 123b which rotates in the direction opposite the tilting direction of the passage operation portion 120 to reach a position of a balanced state, the balancing portion 123b rotates in the tilting direction of the passage operation portion 120.

In addition, the contents 5 are pushed and move in a direction opposite an axis along the external curved surface of the movement member 125 such that the effective passage space through which other contents may pass together is lost.

Here, a protruding configuration formed as a curve or the like along the outer surface of the movement member 125 to reduce the effect passage space through which other contents pass together is a bottom height changing member 147 which relatively increases a bottom height of the movement member 125 with which contents come into contact while passing and reduces a space of the opening portion 122, which is opened to pass the contents.

Also, at least the weight or the center of gravity of the passage movement portion 140 including the opening member 124 or the balancing portion 123b may be formed by allowing the passage movement portion 140 to have a shape or by combining a component of the passage movement portion 140 so as not to allow necessary contents to rotate due to the weight of the passage movement portion 140 before coming into contact with the opening member 124 when the housing 110 including the passage operation portion 120 tilts.

Also, the contents passage means 123 includes the movement member 125, which pivotably connects to the opening member 124.

Particularly, the passage operation portion 120 includes the fixing member 121, which includes the opening portion 122 to pass the contents 5 therethrough.

The contents passage means 123 includes the opening member 124 and the movement member 125.

The opening member 124 is connected to the fixing member 121. Thus, the opening member 124 is moved and may receive and guide the contents 5 depending on whether the opening portion 122 is opened.

Also, the movement member 125 movably connects to the opening member 124.

Accordingly, when the contents 5 press on the opening member 124, the contents 5 are induced as the opening member 124 tilts. The blocking member 127 interconnects to the opening member 124 and blocks at least a part of the opening portion 122 so as to prevent an excessive quantity of the contents from passing.

Here, when the contents movement device or accommodation device 1 tilts, due to a force of the passage movement portion 140 to rotate in a direction opposite a tilting direction of the contents movement device or accommodation device 1 to maintain balance thereof or to be balanced with the center of gravity of the passage movement portion 140, the passage movement portion 140 tilts more than the contents movement device or accommodation device 1 such that the balancing portion 123b does not tilt any further.

Here, as shown in FIG. 5, a direction of the force of the passage movement portion 140 or the balancing portion 123b to maintain balance thereof or to be balanced is opposite to the tilting direction of the contents movement device or accommodation device 1, and the rotating force is generated by a force of the passage movement portion 140 or the balancing portion 123b. Particularly, the passage movement portion 140 may additionally include a movement control member 123a for a balance of the weight of gravity of the passage movement portion 140.

When the passage operation portion 120 tilts, a weight-balancing force of the movement control member 123a, is applied to the center of gravity of the balancing portion 123b due to weights of the opening member 124 and the movement control member 123a or weights of the opening member 124, the movement control member 123a, and an additional member which moves with the opening member 124. The movement control member 123a may prevent the opening member 124 from tilting more than the passage operation portion 120 by a force for maintaining a position of the center of gravity in a gravitational direction.

When the passage operation portion 120 tilts in the direction in which the contents 5 slide toward the passage device 100, the weight-leaning force is applied in a direction opposite to the direction in which the passage operation portion 120 tilts such that the passage movement portion 140 suppresses the opening member 124 from tilting at an angle equal to or greater than an angle at which the passage operation portion 120 tilts, in the direction in which the passage operation portion 120 tilts, due to the weight of the opening member 124.

As the passage operation portion 120 tilts, the contents slide downward and come into contact with the opening member 124 such that the weight of the contents 5 is added in the direction in which the passage operation portion 120 tilts to generate weight-leaning in the direction in which the passage operation portion 120 tilts. Before this, the balancing portion 123b including the opening member 124 suppresses movement of the opening member 124 in a direction of being opened to discharge the contents which is caused by the weight of the opening member 124 and maintains the opening member 124 in an open standby state before the contents 5 come into contact therewith.

As described above, the passage movement portion 140 may become the balancing portion 123b, and the balancing portion 123b may be configured to generate a force for rotating in the direction opposite to the tilting direction of the passage operation portion 120 which tilts to pass the contents in a weight-balanced state of the balancing portion 123b. Accordingly, due to the weight balance of the balancing portion 123b, the opening member 124 does not tilt in the tilting direction of the passage operation portion 120 and a force of the balancing portion 123b to rotate in the direction opposite the tilting direction of the passage operation portion 120 is applied.

Also, the force of the balancing portion 123b to rotate in the direction opposite the tilting direction of the passage operation portion 120 may be resisted by a member of the contents device such as the fixing member 121 or the housing 110 so as to be suppressed not to rotate in the direction opposite the tilting direction of the passage operation portion 120. Accordingly, the balancing portion 123b does not tilt in the tilting direction of the passage operation portion 120 due to a force of the balancing portion 123b to maintain a balanced state direction or to rotatably move and is resisted by the fixing member 121 or the housing 110 such that rotation in the direction opposite to the tilting direction of the passage operation portion 120, which is caused by the force of the balancing portion 123b to maintain the balanced state direction or to rotatably move, is suppressed.

That is, as the passage operation portion 120 tilts, when the contents comes into contact with the opening member 124, at least a part or all of the weight of the contents 5 is added to the balancing portion 123b such that weight-leaning of the balancing portion 123b occurs in the tilting direction of the passage operation portion 120 which is a leftward direction in FIGS. 7 and 8. Here, when the weight-leaning of the balancing portion 123b in the tilting direction of the passage operation portion 120 which occurs due to the weight of the contents 5 added to the opening member 124 exceeds a balance-maintaining force of only the balancing portion 123b which rotates in the direction opposite the tilting direction of the passage operation portion 120 to reach a position of a balanced state, the balancing portion 123b rotates in the tilting direction of the passage operation portion 120. Here, the rotation of the balancing portion 123b may come into contact with and be resisted by the member of the contents device such as the fixing member 121 or the housing 110 and may prevent the balancing portion 123b from unnecessary rotating in the tilting direction of the passage operation portion 120.

When the passage operation portion 120 and the contents movement device or accommodation device 1 tilt together, the balancing portion 123b or the passage movement portion 140 may not tilt more than the passage operation portion 120 tilts and maintain a position and a tilt in the passage operation portion 120 due to an action of balancing weight by using the center of gravity of the balancing portion 123b or the passage movement portion 140.

That is, the passage movement portion 140 is provided in the opening portion 122 to move like a seesaw such that the passage operation portion 120 remains in an initial state and the opening member 124 does not open the opening portion 122 when the passage operation portion 120 tilts within the preset angle.

The opening portion 122 is opened by a force of the contents pushing on the passage movement portion 140 or the weight of the passage movement portion 140 and the force of the contents pushing on the passage movement portion 140 and a preset quantity of the contents passes and is guided to pass through.

The preset angle may be set to be a tilting angle which is less than 180 degrees from the initial state in which the contents movement device or accommodation device 1 with the opening portion 122 stands.

The passage movement portion 140 may perform the seesaw movement due to a weight-leaning phenomenon on a left side or a right side on the basis of the movement member 125 which is a rotational center.

In a standby state in which the contents movement device or accommodation device 1 which includes the opening portion 122 tilts, a weight leans on the blocking member 127 on the basis of the movement member 125, which is the rotational center, and the blocking member 127 is held by the stopper such that the passage movement portion 140 may maintain a state in which the blocking member 127 does not block and opens the opening portion 122.

When the contents movement device or accommodation device 1 which includes the opening portion 122 tilts within a preset angle, the passage movement portion 140 may maintain a state in which the opening member 124 blocks the opening portion 122.

When the contents movement device or accommodation device 1 which includes the opening portion 122 tilts, the weight of the contents which move toward the opening portion 122 is increased such that the passage movement portion 140 may pivot on the basis of the movement member 125, which is the rotational center, and open the opening portion 122.

As described above, the passage movement portion 140 may reciprocally pivot at the opening portion 122 on the basis of the movement member 125 due to a weight-balancing principle of a seesaw lever and may open or close the opening portion 122.

The passage movement portion 140 may maintain a state in which the opening portion 122 is closed by the weight thereof when the passage operation portion 120 pivots within a preset angle and sequentially open or close the opening portion 122 due to a force of the contents pushing on the passage movement portion 140 and due to the weight of the passage movement portion 140 so as to guide a passage of a preset quantity of contents.

The passage movement portion 140 may include the balancing portion 123b configured to suppress the passage movement portion 140 so as to not to tilt more than the passage operation portion 120 tilts due to the weight of the passage movement portion 140.

The passage movement portion 140 may include the opening member 124 which moves in a passage direction of the contents and forms a passage space for the contents.

The passage movement portion 140 may include the blocking member 127 which interlocks with the opening member 124 to block at least a part of the opening portion 122 such that the contents do not pass therethrough or only partially pass therethrough.

The passage operation portion 120 or the contents passage means 123 may have shapes that prevent pivoting, which is caused by the weight of the passage movement portion 140 due to weight balance, before the preset quantity of contents comes into contact with the opening member 124.

The passage movement portion 140 may further include the movement control member 123a for setting a balance in a center of gravity of a lever movement.

The passage operation portion 120 includes a resistance member 110a provided therein. The resistance member 110a restricts a passage of the contents which pass through the passage operation portion 120.

The passage operation portion 120 includes the resistance member 110a provided therein, and the resistance member 110a restricts the passage of the contents which pass through the passage operation portion 120 and resists the passage of the contents in conjunction with the blocking member 127.

The resistance member 110a may be configured to protrude into the passage operation portion 120 so as to prevent contents which exceed a demanded quantity thereof from easily entering. Also, in conjunction with the blocking member 127 which moves, entry of contents which exceed the demanded quantity thereof may be more effectively prevented.

The resistance member 110a may have various forms. For convenience, it is shown that a part of a resistant top plate member 182 is formed to be recessed inward.

Also, the passage movement portion 140 includes an accommodation member 127a.

The accommodation member 127a moves toward the opening member 124 in conjunction with the opening member 124 and moves with the opening member 124 while accommodating the demanded quantity of contents.

In addition, the contents 5 come into contact with one or more of the resistant top plate member 182 and a resistant side plate member 183 such that a residual quantity of contents which pass through the opening portion 122 is restricted.

The resistant top plate member 182 may be provided in the movement guide portion 180, and the resistant side plate member 183 may be connected to the resistant top plate member 182 or the fixing member 121.

Particularly, although the resistant side plate member 183 may be formed on a surface of the fixing member 121 which faces the passage direction of the contents 5 when the openable cover 30 is provided, the resistant side plate member 183 may be formed on the cover 30 to move when the cover 30 is opened so as to not interfere with picking up contents.

Of course, the resistant top plate member 182 and the resistant side plate member 183 may have a variety of shapes in the passage direction and a passage-side direction of the contents 5.

Also, the movement guide portion 180 includes a contents induction portion 188 at an inlet side of the contents 5. The contents induction portion 188 divides a height difference which occurs during movement of contents toward the contents passage means 123 into a plurality of steps or inclines such that the height difference does not block the movement of the contents and induces the movement of the contents in order to induce the contents in the passage-anterior portion 113 to stably move toward the passage path portion 139. Of course, the contents induction portion 188 is modifiable to a variety of shapes.

Meanwhile, the passage device 100 further includes the supply guide portion 119.

The supply guide portion 119 is formed in the housing 110 to set a movement direction and a movement state of the contents 5 to allow the contents 5 which move toward a discharge side of the passage operation portion 120 to be discharged one by one or in a fixed quantity thereof.

Particularly, the housing 110 includes a reduced-diameter portion 116 and an enlarged-diameter portion 117.

The reduced-diameter portion 116 holds the fixing member 121 and has a reduced diameter to guide the contents 5 to move toward the movement guide portion 180. Here, the diameter of the reduced-diameter portion 116 is similar or equal to a circumference formed along the contents induction portion 118, a guide member 190, and the resistant top plate member 182.

Also, the enlarged-diameter portion 117 has an inner space larger than that of the reduced-diameter portion 116 to store an initially set quantity of contents. Of course, a diameter of the enlarged-diameter portion 117 is not limited.

Also, the supply guide portion 119 is formed at a connection part between the reduced-diameter portion 116 and the enlarged-diameter portion 117 of the housing 110 to be formed convexly inward with a curvature along the circumference. Then, a preset quantity of the contents 5 move along the supply guide portion 119 and are guided to move into the contents induction portion 188 and the guide member 190 as much as a preset quantity thereof.

Of course, the supply guide portion 119 is modifiable to a variety of shapes.

A sliding-beginning end of the contents induction portion 188 which induces the contents toward the passage path portion 139 is located to be adjacent to or in contact with an inner diameter of the reduced-diameter portion 116 which corresponds to a neck part of the housing 110 which is a container body according to the embodiment. Accordingly, the sliding-beginning end of the contents induction portion 188 is located to be connected to the supply guide member 119 which has a curved shape such that the contents smoothly move and are guide to move slidably from the enlarged-diameter portion 117 to the passage path portion 139.

An injection-blown container includes the reduced-diameter portion 116 which is a neck part narrower than the enlarged-diameter portion 117 which is a container body because air pressure is applied to an opening of the container housing 110.

Accordingly, the injection-blown container has a shape in which an end part of the contents induction portion 188 provided in the passage device 100 is inclined, bent, or includes a step to entirely or partially connect an inner diameter of a container neck 116 to an inner diameter of the container body 117 so as to allow the contents to smoothly move toward the passage path portion 139 when the housing 110 tilts and the contents slide.

Like the embodiment, when a step is present between a contents entry part of the contents induction portion 188 and the enlarged-diameter portion 117, a shape modification portion 119 which connects a step between the contents entry part of the contents induction portion 188 and the enlarged-diameter portion 117 may be provided. In the embodiment, the shape modification portion 119 is the supply guide portion 119 which connects a step between the reduced-diameter portion 116 and the enlarged-diameter portion 117 to supply and move the contents at the step in the housing.

Also, like the embodiment, in the case of not only an injection-blown container in which an inlet is narrower than a container body but also an injection container in which an inlet is not narrower than a container body, since an operation position of a rotating shaft of the opening member 124 of the passage movement portion 140 is located to be spaced apart from an inner diameter of the container housing 110 in an inward direction, a difference in a position of solid contents, which slidably move, may occur and a contents entry part of the contents induction portion 188 which faces a container bottom may be inclined, bent, or include a step to connect a step therebetween.

In the case of both the injection-blown container and the injection container, an operation position of the opening member 124 is located inside the inner diameter of the container such that a difference from a position of the contents which approaches from the container body 117 and the contents induction portion 188 is configured to be inclined, bent, or with a step to connect the difference.

In the embodiment, the container body 110 is an injection-blown container and includes the reduced-diameter portion 116 which is narrower than the enlarged-diameter portion 117 because air pressure is applied to an upper opening of a body.

In the embodiment, the contents induction portion 188 is provided to connect a step between the inner diameter of the reduced-diameter portion 116 and the opening member 124 located to be spaced apart from the inner diameter of the reduced-diameter portion 116. In the case of the injection-blown container like the embodiment, a step connection portion 188 connects an inside of the container reduced-diameter portion 116 and an inside of the container body 117 such that contents smoothly slide.

Also, the supply guide portion 119 is included, which is an inclined part which connects the reduced-diameter portion 116 narrower than the container body 117 to the enlarged-diameter portion 117 in which contents are stored and wait for movement. The supply guide portion 119 may perform a function of connecting a step which occurs when the housing 110 tilts to move the contents in the enlarged-diameter portion 117 to the contents induction portion 188.

Unlike the embodiment, when a step-beginning point, which is a step-beginning end of the contents induction portion 188 which faces the container bottom, is larger than the inner diameter of the reduced-diameter portion 116, in order to insert the passage device 100 into the housing 110, it is necessary to perpendicularly insert a bottom of the passage device 100, which includes the beginning point of the contents induction portion 188 which faces the container bottom and is a step-beginning end of the contents induction portion 188, to horizontally move a position of the passage device, and to perpendicularly insert the passage device 100 such that three operations of perpendicularly moving, horizontally moving, which is an intermediate operation, and perpendicularly moving are necessary for assembly.

Meanwhile, like the embodiment, the contents induction portion 188 of the passage device 100 allows the guide member 190 and the beginning point of the contents induction portion 188 which is close to the inner diameter of the housing to be located inside the reduced-diameter portion 116 so as to directly insert the passage device 100 into the housing 110 in one direction during assembling.

Particularly, this is shown in features of a blown container which includes the container neck 116 part which is the reduced-diameter portion 116 that is narrower than the container body 117 which is the enlarged-diameter portion 117. The housing 110 is an injection-blown container with a convex body and the reduced-diameter portion 116 in which significant portions of the passage device 100 are located.

Accordingly, when an outer diameter of the entire bottom of the passage device 100 including the contents induction portion 188 which faces the enlarged-diameter portion 117 is configured to be smaller than the inner diameter of the container reduced-diameter portion 116, the passage device 100 may be inserted into the housing 110 in one direction at once without horizontal movement which is the intermediate operation of assembling into the container body.

Meanwhile, when the passage device 100 is assembled in the container body, a top end of the reduced-diameter portion 116 may be configured to be wider to support the bottom from above, or a step may be formed in the reduced-diameter portion 116.

Also, to prevent the passage device 100 which is a contents passage dispenser from being separated outward due to the weight of the contents in contact therewith when the container tilts, a protruding portion may be formed on an upper outer diameter of the passage device 100, and a groove may be formed in the top end of the reduced-diameter portion 116 of the housing 110 corresponding thereto so as to engage the reduced-diameter portion 116 with the housing 110 when the reduced-diameter portion 116 is inserted therein.

A variety of shapes of lids may be combined with the top end of the reduced-diameter portion 116.

The housing 110 may be linearly connected without division between the enlarged-diameter portion 117 and the reduced-diameter portion 116 or may have a variety of shapes. That is, the housing 110 may be manufactured as, for example, a container having a uniform diameter.

As a result, in an initial standing state, a state in which the opening member 124 blocks the opening portion 122 is maintained by a weight-balancing force of the passage movement portion 140. That is, when a force of rotating to one side (a right side) is applied, the stopper 129 blocks one-side rotation of the passage movement portion 140.

Also, the passage movement portion 140 does not tilt toward the other side (a left side), which is a position direction, nor tilt more than horizontality such that it enters a state in which the contents 5 do not slide. In addition, when the container 110 tilts at a certain angle (within 90 degrees), gravity works in a vertically lower direction of a rotational center of the passage movement portion 140. Thus, even when a weight of one side based on a vertical line is greater and a force of rotating in one side direction occurs, an actual rotation does not occur due to the stopper 129.

When the container 110 is in a level state, one side of a certain vertical line becomes heavier such that the force to rotate in one side direction is generated. However, the actual rotation does not occur due to the stopper 129. Accordingly, the passage movement portion 140 itself does not rotate.

In addition, when the container 110 further tilts past horizontality, the blocking member 127 is opened and is in a standby state without movement of the passage movement portion 140. Here, the contents 5 slidably move in the gravitational direction according to an incline of the inside of the container 110.

Particularly, even when a step is present between the container 110 and the guide member 190, a piece of the contents 5 having a tablet shape lies down and does not stand so as to enter the guide member 190.

Here, a first piece of the contents 5 among the contents 5 in the container 110 do not enter a passage compartment portion 124*a* provided between the opening member 124 and the blocking member 127 of the passage movement portion 140.

In addition, the contents 5 which have an oblong shape and not a flat shape do not stand and stably slide along an incline of the guide member 190.

Here, before the container 110 tilts over 90 degrees, the contents 5 do not come into contact with the passage movement portion 140.

Meanwhile, when the container 110 tilts over 90 degrees, the passage movement portion 140 moves (pivots) with the contents 5 in a space of the passage compartment portion 124a due to friction between the contents 5 and a bottom member or a force of the contents 5 pushing the opening member 124.

Here, as the weight of the contents 5 and a weight of the embodiment on the left side of the vertical line which is the gravitational direction increase more than a weight of the right side such that weight-leaning on the left side occurs (refer to FIG. 9), the passage movement portion 140 rotates toward the left side based on the rotational center 125, that is, in a counterclockwise direction, and passes the contents 5 outward.

Since the fixed quantity of the contents 5 moves outward and does not come into contact with the passage movement portion 140, the passage movement portion 140 has a greater weight on the right side such that the force of rotating in a rightward direction is generated. However, the residual contents 5 come into contact with the blocking member 127 due to gravity and remain as they are.

Particularly, FIG. 5 illustrates a state in which the housing 110 tilts beyond horizontality (−90 degrees or more). Here, the initial state in which the blocking member 127 is opened and the passage movement portion 140 does not move (pivot) is maintained. The contents 5 start moving while sliding along the incline of the inside of the housing 110 due to a force in the gravitational direction C.

Even when a step is present between the housing 110 and the guide member 190, a piece of the contents 5 having a tablet shape does not stand and lie to enter the guide member 190. Here, it becomes a state in which a first piece of the contents (tablets) 5 does not enter the passage compartment portion 124a provided between the opening member 124 and the blocking member 127 of the passage movement portion 140.

The contents 5 which have a tablet shape and not a flat shape do not stand and stably slide along the incline of the guide member 190.

Although the passage movement portion 140 tilts counterclockwise by more than 90 degrees on the basis of the initial state due to the tilt of the housing 110, the contents 5 do not come into contact with the passage movement portion 140. The passage movement portion 140 attempts to rotate clockwise, which is a rightward direction, due to weight leaning on the right side based on the movement member 125 but is suppressed by the stopper 129 to remain in a standby state.

FIG. 6 illustrates a state in which the blocking member 127 is opened and the contents 5 enter an internal space of the passage movement portion 140.

The weight of the contents 5 is added to the balancing portion 123b of the passage movement portion 124 such that weight-leaning on a left part of the gravitational vertical line C which is a side of the opening member 124 increases relatively. Accordingly, in order for the contents 5 to come into contact with the opening member 124, the contents 5 approach the opening member 124, or as the contents approach the opening member 124, the passage movement portion 140 may rotate counterclockwise, tilting more than the housing 110.

Here, due to friction between the contents 5 which move along the incline in the gravitational direction or a force of pushing the opening member 124, the passage movement portion 140 moves with the contents 5 in the space of the passage compartment portion 124a.

FIG. 7 illustrates a state in which the passage movement portion 140 rotates further counterclockwise on the basis of the movement member 125 from the initial state such that the blocking member 127 starts blocking contents 6 which enter after the fixed quantity of the contents (tablets) 5.

Here, with the weight of the contents 5 having a tablet shape, a weight of the left side of the gravitational vertical line C becomes greater than a weight of the right side such that weight leaning on the left side may occur and the passage movement portion 140 rotates counterclockwise, that is, the left side of the rotational center of the movement member 125 passes the contents 5 outward.

As shown in FIG. 8, when the passage movement portion 140 rotates further counterclockwise on the basis of the movement member 125 from the initial state, the fixed quantity of the contents 5 pushing the passage movement portion 140 moves outward and does not come into contact with the opening member 124 side of the passage movement portion 140 any further such that the passage movement portion 140 has a greater weight on the right side based on the central line C and a force of rotating clockwise, that is, in the rightward direction, is generated. However, as the residual contents 6 come into contact with the blocking member 127 due to gravity, a valve 100 can not return to the right side and maintains a present state such that the contents 5 do not enter any further in the space of the passage compartment portion 124a.

As shown in FIG. 10, when a piece of the contents 5 has a tablet shape with a length X equal or similar to a width Y and a height Z or in any shape which is not flat, a space of the passage path portion 139 may be configured to have a lateral width which is greater than the width of one piece of the contents and is two times or less the width of the piece of the contents 5 which is the fixed quantity.

When a single quantity passes as the fixed quantity, a passage space allowance of the passage path portion 139 may be provided within a range in which a shortest lateral width is greater than and two times less than an axial length of a cross section of the piece of the contents 5. This is to prevent the contents 5 which exceed the single quantity from passing through the passage path portion 139 at the same time. When it is necessary to pass a plurality of pieces of the contents 5, the passage space allowance is adjustable be greater than or equal to two times the shortest lateral width of a cross section of the piece of the contents 5.

In FIG. 11, when the fixed quantity of the contents 5 is a single piece and the single piece as the fixed quantity passing through the space which has a longitudinal height which is equal to or is less than two times a maximum length of a height or a width of one piece of the contents 5, a passage space allowance, in which a shortest longitudinal width of the passage path portion 139 is equal to and not greater than two times a width of the axis of the cross section of the contents 5, may be provided. This is to prevent the contents 5 which exceed the single quantity from passing through the passage path portion 139 at the same time.

FIG. 12 illustrates a case in which the passage movement portion 140 returns to a state before tilting or a standing state. When the fixed quantity of the contents 5 passes outward and then the housing 110 moves clockwise to return to the initial state, the contents 5 come into contact with the blocking member 127 and the contents 6 which push the blocking member 127 move down due to the gravity C and are separated from the blocking member 127 and the passage movement portion 140 rotates clockwise, which is the rightward direction, due to weight-leaning on the right side on the basis of the movement member 125 and rotates until the point when the stopper 129 resists to return to the initial state. When the blocking member 127 returns while being opened and tilts leftward again, it enters a passage standby state in which the passage movement portion 140 does not rotate until the contents 5 initially come into contact with the passage movement portion 140.

Afterwards, when the housing 110 tilts toward the opening portion 122, as shown in FIG. 5, a condition for a preparation operation in which a passage of the fixed quantity of the contents may be induced may be satisfied.

Figure 13:
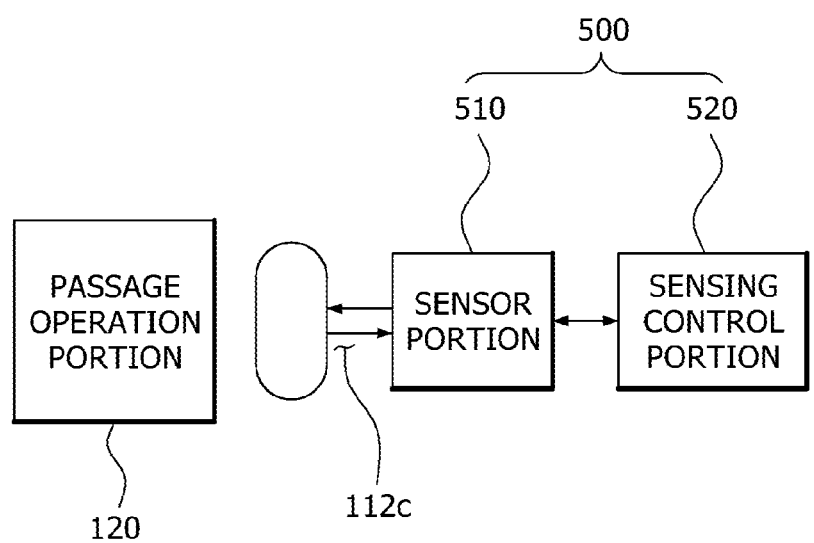
FIG. 13 is a block configuration diagram illustrating a sensor module provided in a passage device according to a second embodiment of the present invention.
Figure 14:
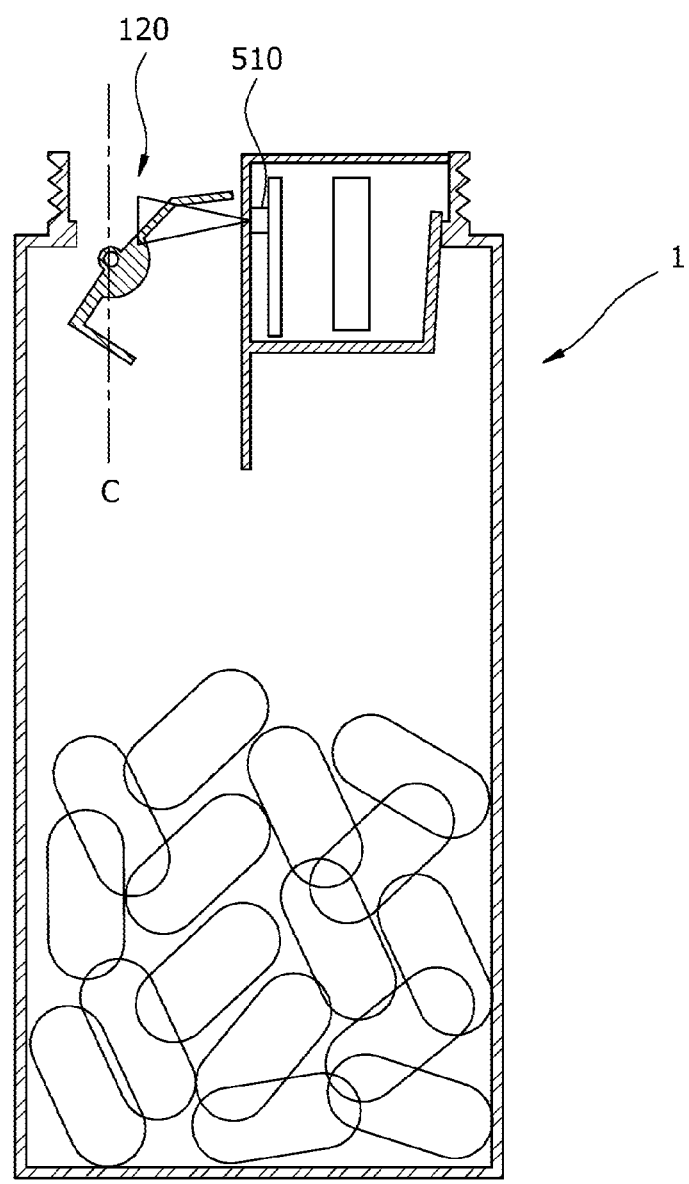
FIG. 14 is a schematic view of an administration management device according to the second embodiment of the present invention.
Figure 15:
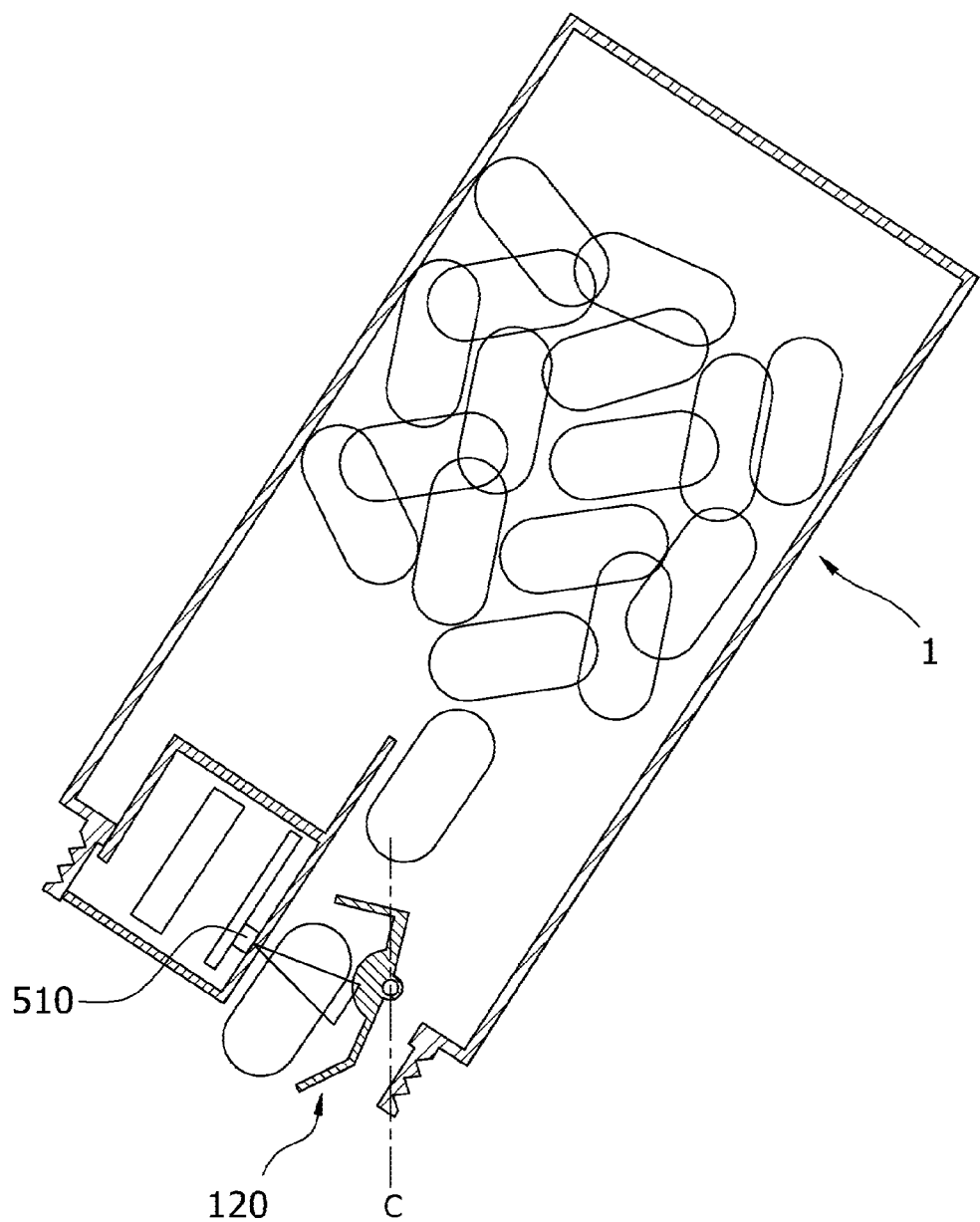
FIG. 15 is an operation state diagram illustrating a state in which the administration management device tilts according to the second embodiment of the present invention.

FIG. 13 is a block configuration diagram illustrating a sensor module provided in a passage device according to a second embodiment of the present invention, FIG. 14 is a schematic view of an administration management device according to the second embodiment of the present invention, and FIG. 15 is an operation state diagram illustrating a state in which the administration management device tilts according to the second embodiment.

Figure 16:
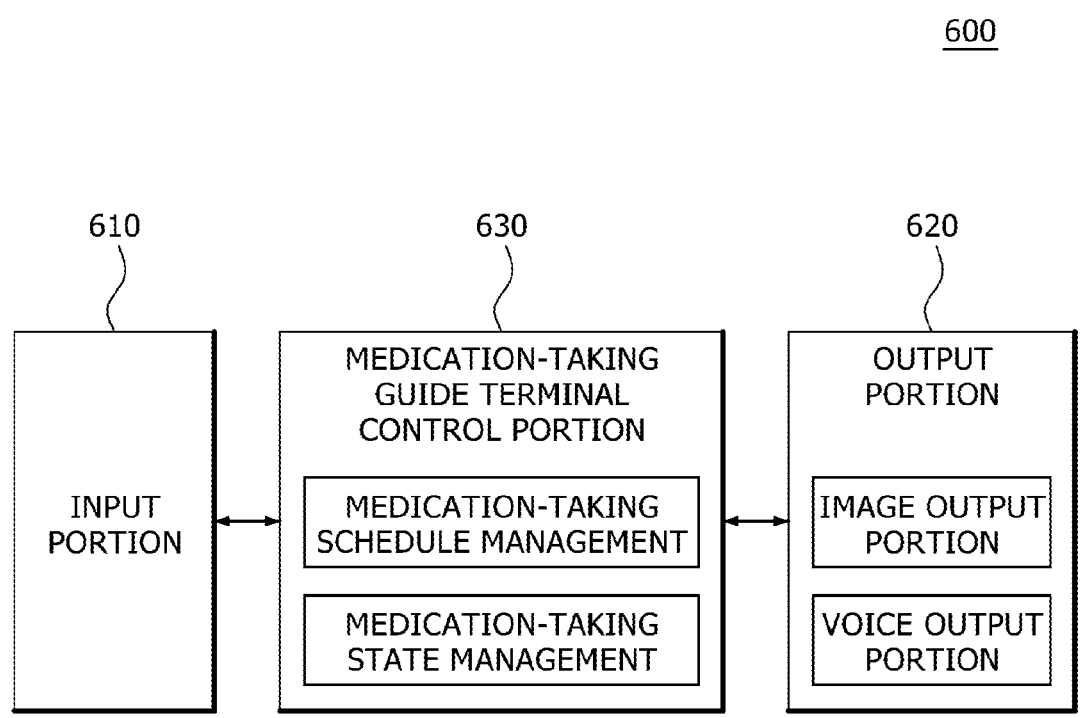
FIG. 16 is a block diagram illustrating a medication-taking guide terminal of the administration management device according to the second embodiment of the present invention.
Figure 17:
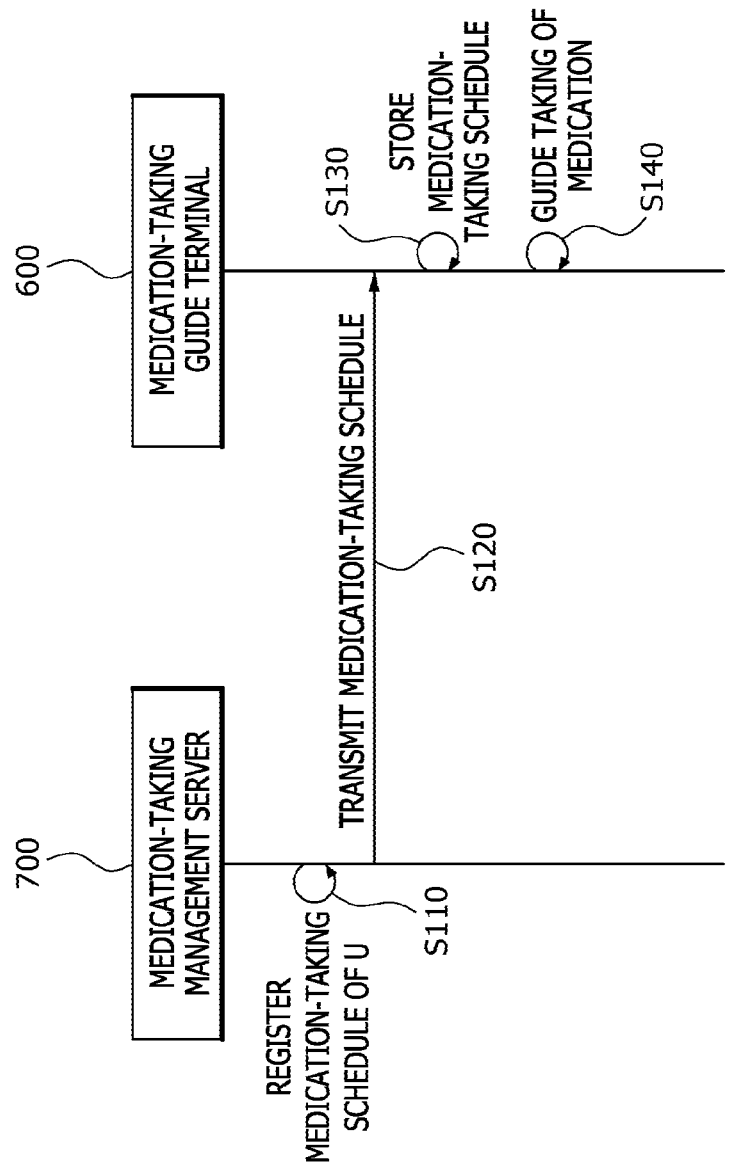
FIG. 17 is an operational diagram illustrating the medication-taking guide terminal according to the second embodiment of the present invention.
Figure 18:
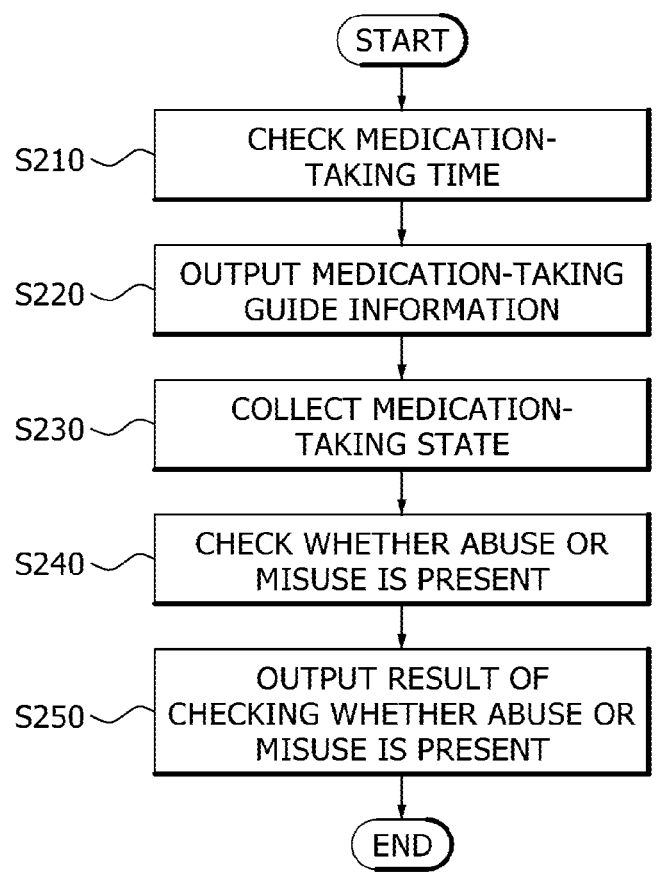
FIG. 18 is a flowchart illustrating operations performed by the administration management device according to the second embodiment of the present invention.

FIG. 16 is a block diagram illustrating a medication-taking guide terminal of the administration management device according to the second embodiment of the present invention, FIG. 17 is an operational diagram illustrating the medication-taking guide terminal according to the second embodiment of the present invention, and FIG. 18 is a flowchart illustrating operations performed by the administration management device according to the second embodiment of the present invention.

Figure 19:
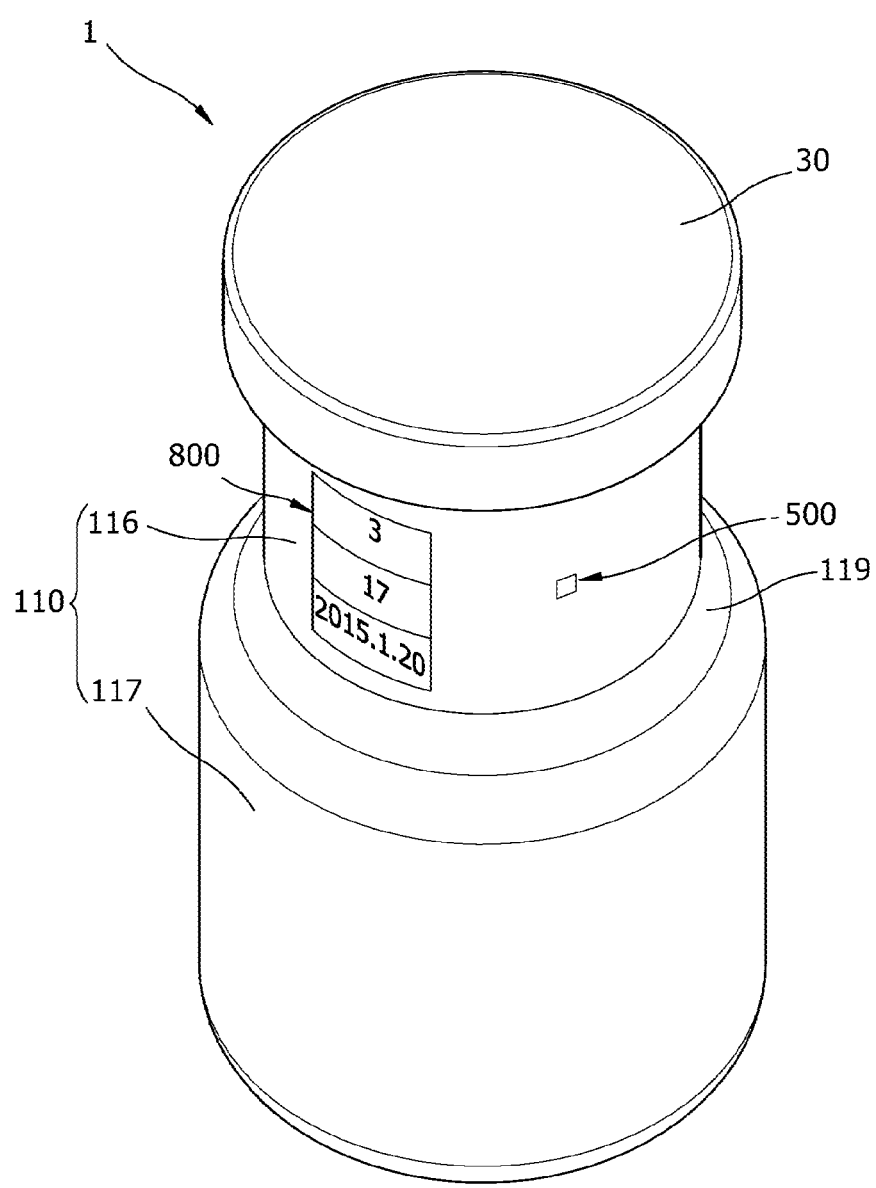
FIG. 19 is a perspective view illustrating a housing including the administration management device according to the second embodiment of the present invention.
Figure 20:
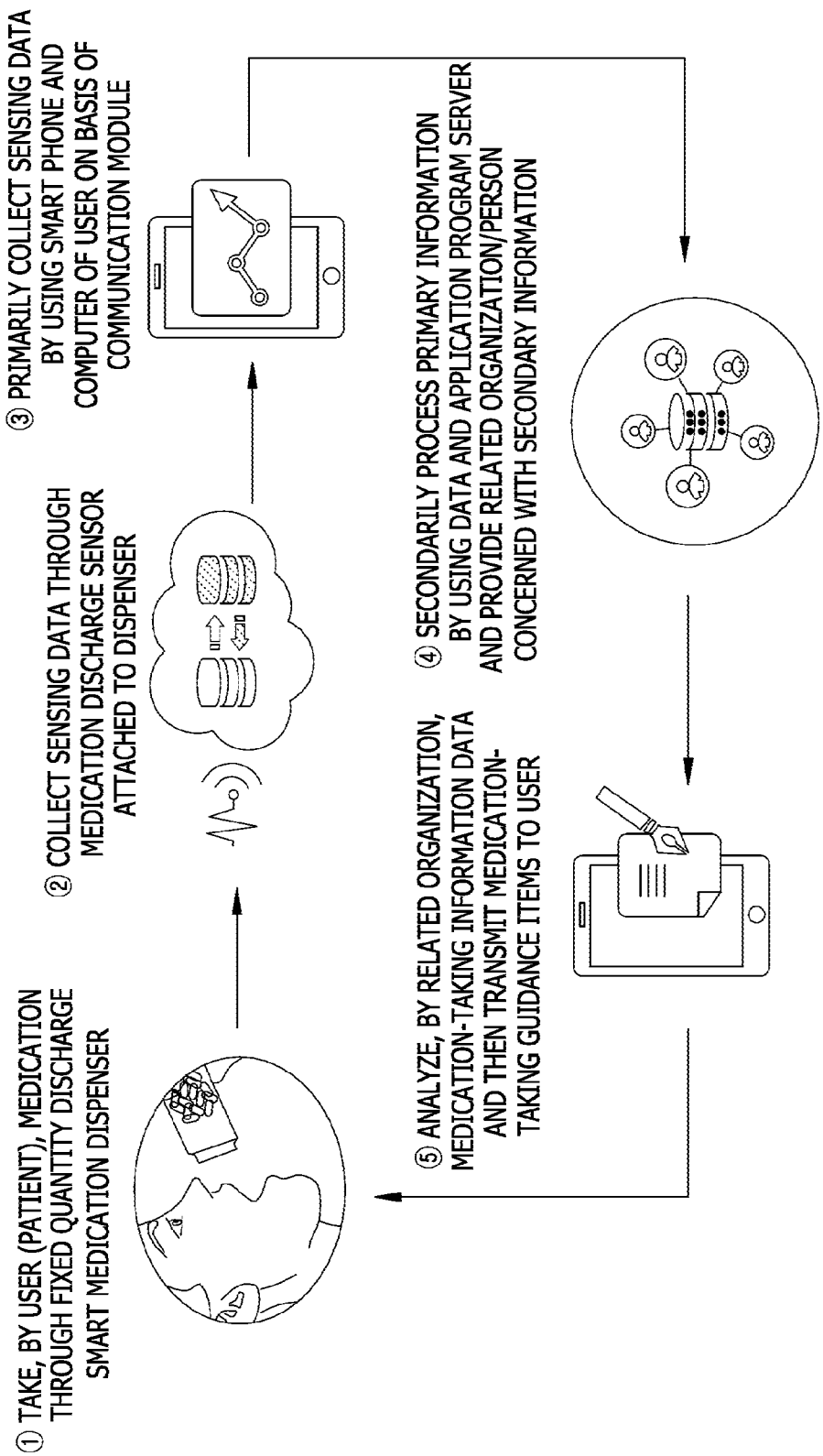
FIG. 20 illustrates a communication system of the administration management device according to the second embodiment of the present invention.
Figure 21:
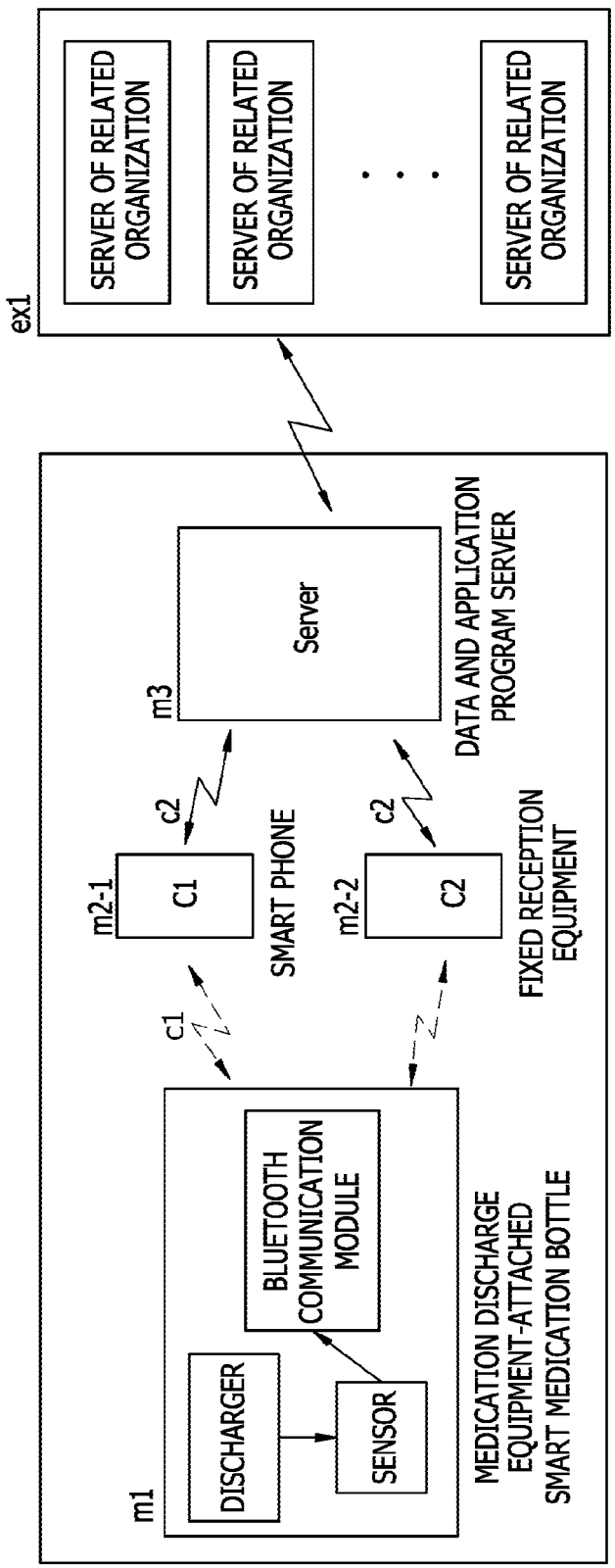
FIG. 21 illustrates a communication operation diagram illustrating the administration management device according to the second embodiment of the present invention.

FIG. 19 is a perspective view illustrating a housing including the administration management device according to the second embodiment of the present invention, FIG. 20 illustrates a communication system of the administration management device according to the second embodiment of the present invention, and FIG. 21 illustrates a communication operation diagram illustrating the administration management device according to the second embodiment of the present invention.

As shown in FIGS. 13 to 21, the contents movement device 1 which includes the passage operation portion 120 of the passage device according to the second embodiment of the present invention includes a medication-taking management device.

Also, the medication-taking management device includes a sensor module 500, a medication-taking guide terminal 600, and a medication-taking management server 700.

The sensor module 500 senses the contents 5 which are discharged by the passage operation portion 120. The passage operation portion 120 allows a preset quantity of the contents 5 to be discharged. Accordingly, when the contents 5 discharged through the passage operation portion 120 are sensed, an amount of the contents 5 discharged from the contents movement device 1 may be precisely sensed.

As described above, the contents are discharged through a passage space 112c of the passage operation portion 120. The sensor module 500 may sense the contents 5 discharged through the passage space 112c. Here, description of seesaw movement and pivoting of the passage operation portion 120 with respect to a rotational center or a weight direction C will be replaced by the above description.

Also, the sensor module 500 senses the contents 5, generates medication-taking state information according to a result of sensing, and transmits the medication-taking state information to the medication-taking guide terminal 600.

Particularly, referring to FIGS. 13 to 15, the sensor module 500 includes a sensor portion 510 and a sensing control portion 520.

The sensor portion 510 senses the contents 5 discharged by an operation of the passage operation portion 120 through the passage space 112c. For this, as shown in FIGS. 14 and 15, the sensor portion 510 is installed on one side of the passage space 112c and is installed on the other side of the passage operation portion 120 with the passage space 112c as a center.

The sensor portion 510 emits light toward the passage space 112c and receives the light reflected by the passage operation portion 120 or the contents 5.

That is, the sensor portion 510 may be installed on the other side of the passage operation portion 120 with the passage space 112c as the center, emit light toward the contents 5 discharged through the passage space 112c, and receive the light reflected by the contents 5 so as to precisely sense the contents 5 being discharged through the passage space 112c.

The sensing control portion 520 controls the sensor portion 510 to sense the contents 5 which pass through the passage space 112c, generates medication-taking state information according to a result of sensing, and transmits the medication-taking state information to the medication-taking guide terminal 600.

That is, the sensing control portion 520 controls the sensor portion 510 to emit light toward the passage space 112c. The light emitted by the sensor portion 510 is reflected by the passage operation portion 120 or the contents 5 depending on whether the contents are discharged through the passage space 112c. The reflected light is received by the sensor portion 510.

When the light is received by the sensor portion 510, the sensing control portion 520 controls the sensor portion 510 to detect a time difference between a time of emitting light and a time of receiving the light by the sensor portion 510.

Subsequently, the sensing control portion 520 compares the time difference with a preset set value and determines that the contents 5 have passed through the passage space 112c when the time difference is within the set value.

Here, the set value is a reference value for determining whether the contents 5 are discharged through the passage space 112c. Generally, when the contents 5 pass through the passage space 112c, a distance between the sensor portion 510 and the contents 5 decreases. Accordingly, when the time difference is within the set value, it may be determined that the contents 5 have passed through the passage space 112c.

The set value may be variously set according to an inner diameter of the passage space 112c, a type of the contents 5, a size of the contents, and the like.

Referring to FIG. 14, when the contents movement device 1 is disposed not to discharge the contents, the contents are not discharged into the passage space 112c.

On the other hand, as shown in FIG. 15, when the contents movement device tilts such that the contents 5 are discharged, since the contents 5 are discharged through the passage space 112c, light emitted by the sensor portion 510 is reflected by the contents 5 and received.

Meanwhile, since the contents 5 are sensed depending on whether the time difference is within the preset set value, the sensing control portion 520 generates medication-taking state information on the basis of a result of sensing the contents 5 and transmits the generated medication-taking state information to the medication-taking guide terminal 600.

The medication-taking state information includes information on the contents 5, whether the contents 5 are sensed, time information of sensing the contents 5, and the like. The information of the contents 5 may be preset in the sensing control portion 520 or the like, and whether the contents 5 are sensed and the sensing time may be detected in real time depending on whether the sensor portion 510 senses the contents 5.

Referring to FIG. 16, the medication-taking guide terminal 600 receives the medication-taking state information from the sensor module 500, receives medication-taking schedule information from the medication-taking management server 700, generates medication-taking management information using the medication-taking schedule information and the medication-taking state information, and outputs the generated medication-taking management information.

The medication-taking schedule information includes at least one of the information of the contents 5, a medication-taking time, a medication-taking interval, and a dosage of the contents 5. The medication-taking schedule information may be generated by the medication-taking management server 700 on the basis of a prescription from a doctor, a pharmacist, or the like.

Here, as the medication-taking guide terminal 600, a smart terminal, a personal computer (PC), a laptop PC, a fixed terminal, personal digital assistants (PDA), and the like may be employed. As the fixed terminal, a medication reminder and the like may be employed.

The medication-taking guide terminal 600 includes an input portion 610, an output portion 620, and a medication-taking guide terminal control portion 630.

The input portion 610 receives a variety of pieces of information and control commands from a user. The information and control commands input through the input portion 610 may include all information and control commands with respect to use, operations, and setting of the medication-taking guide terminal 600 such as user information, a command for executing an application, a command for setting menus, and the like. As the input portion 610, mechanical buttons, a touch screen, or the like may be employed.

The output portion 620 outputs a variety of pieces of information in response to a control signal of the medication-taking guide terminal control portion 630. The information may include medication-taking state information, medication-taking schedule information, medication-taking management information, and the like. Also, the output portion 620 warns of abuse or misuse of the contents 5 through image or voice alerts.

The output portion 620 includes both an image output portion and a voice output portion, which output the information or warnings in images or voices.

The medication-taking guide terminal control portion 630 receives medication-taking state information from the sensor module 500, receives medication-taking schedule information from the medication-taking management server 700, generates medication-taking management information for a user by using the medication-taking schedule information and the medication-taking state information, and outputs the generated medication-taking management information through the output portion 620.

That is, when the medication-taking state information is transmitted from the sensor module 500 and the medication-taking schedule information is transmitted from the medication-taking management server 700, the medication-taking guide terminal control portion 630 compares the medication-taking state information with the medication-taking schedule information and generates and outputs the medication-taking management information according to a result of the comparison. In this case, the medication-taking guide terminal control portion 630 may warn of abuse or misuse of contents through the output portion 620.

In the embodiment, the abuse or misuse includes both a case in which the contents 5 are not taken and a case in which the contents 5 are not taken according to a determined prescription such as a case in which a fixed quantity of the contents 5 is not taken, a case in which the contents 5 are not taken at a fixed medication-taking time, a case in which the contents 5 are not taken, and the like.

Meanwhile, since the medication-taking state information includes the information of the contents 5, whether the contents 5 are sensed, and the sensing time information of sensing the contents 5 and the medication-taking schedule information includes the information of the contents 5, the medication-taking time, the medication-taking interval, and the dosage of the contents 5, the medication-taking guide terminal control portion 630 may check whether the user abuses or misuses the contents by comparing and analyzing these pieces of information and generates and outputs the medication-taking management information to manage accurate taking of the contents 5.

For example, the medication-taking guide terminal control portion 630 may output a text message or a voice which guides the user to take the contents at a fixed medication-taking time when the user does not take the contents 5 at the medication-taking time and may output a text message or a voice which guides the user to take a fixed dosage when the user does not take the determined dosage.

Also, when the medication-taking schedule information is transmitted from the medication-taking management server 700 as described above, the medication-taking guide terminal control portion 630 outputs at least one of the information of the contents 5 and the dosage of the contents 5 through the output portion 620 according to at least one of the medication-taking time and the medication-taking interval.

That is, when the medication-taking guide terminal control portion 630 checks the medication-taking time or the medication-taking interval and the medication-taking time for the user to take the contents 5 arrives, the information of the contents 5 to be taken and the dosage of the corresponding contents 5 are output through the output portion 620 to allow the user to take the fixed quantity of the corresponding contents 5 at the fixed time.

In addition, when the medication-taking state information is transmitted from the sensor module 500 as described above, the medication-taking guide terminal control portion 630 accumulates and stores the medication-taking state information and generates medication-taking history information by using the medication-taking state information. The medication-taking history information includes a date and time of taking medication, the contents 5, a dosage, and the like.

Then, the medication-taking guide terminal control portion 630 outputs the medication-taking history information, for example, the date and time of taking medication, the contents 5, the dosage, and the like according to a control command input by the input portion 610.

Accordingly, the user may easily recognize his or her time of taking medication, the contents 5, the dosage, and the like according to a temporal order.

The medication-taking management server 700 collects prescription information from a terminal of a doctor, a pharmacist, or the like, generates medication-taking schedule information by using the collected prescription information, and transmits the generated medication-taking schedule information to the medication-taking guide terminal 600.

The medication-taking management server 700 includes an information collection portion 710, a medication-taking schedule information generation portion 720, and a control server 730.

The prescription information collection portion 710 collects prescription information for each user from a terminal of a doctor, a pharmacist, or the like.

The medication-taking schedule information generation portion 720 generates and updates medication-taking schedule information for each user by using the prescription information collected by the prescription information collection portion 710.

The control server 730 controls the prescription information collection portion 710 to collect prescription information from a terminal (not shown) of a doctor, a pharmacist, or the like. Then, the control server 730 controls the medication-taking schedule information generation portion 720 to generate the medication-taking schedule information.

When the medication-taking schedule information is generated as described above, the control server 730 detects user information of a corresponding user and transmits the medication-taking schedule information to the medication-taking guide terminal 600 of the corresponding user on the basis of the user information, for example, contact address information.

Hereinafter, a medication-taking management method according to the second embodiment of the present invention will be described with reference to FIGS. 17 and 18.

Referring to FIG. 17, first, the control server 730 collects prescription information for each user from a terminal of a doctor, a pharmacist, or the like by using a prescription collection portion.

When the prescription information is collected, the control server 730 controls the medication-taking schedule information generation portion 720 to generate medication-taking schedule information by using prescription information, and when the medication-taking schedule information is generated by the medication-taking schedule information generation portion 720, stores the generated user medication-taking schedule information (S110).

In addition, as the medication-taking schedule information is generated, the control server 730 detects user information of a corresponding user and transmits the medication-taking schedule information to the medication-taking guide terminal 600 of the corresponding user by using the user information, for example, contact address information (S120).

When the medication schedule information is transmitted, the medication-taking guide terminal 600 stores the corresponding medication-taking schedule information (S130) and performs a medication-taking management process with respect to the user by using the medication-taking state information transmitted from the sensor module 500 and the medication-taking schedule information (S140).

Referring to FIG. 18, first, when the medication-taking schedule information is transmitted from the medication-taking management server 700, the medication-taking guide terminal control portion 630 stores the medication-taking schedule information.

Then, the medication-taking guide terminal control portion 630 checks a medication-taking time of the medication-taking schedule information (S210) and determines whether a current time coincides with the medication-taking time.

As a result of determination, when the current time coincides with the medication-taking time, the medication-taking guide terminal control portion 630 outputs medication-taking guide information, for example, at least one of information of the contents 5 and a dosage for the contents 5 according to the medication-taking time through the output portion 620 (S220).

Accordingly, the user recognizes that the medication-taking time arrives and takes medication with reference to the information of the contents 5 and the dosage of the contents.

In this case, the user tilts the contents movement device 1 to discharge contents, and due to this, the contents 5 are discharged by the passage operation portion 120 through the passage space 112c.

Since the sensing control portion 520 controls the sensor portion 510 to emit light toward the passage space 112c, the light emitted by the sensor portion 510 is reflected by the contents 5.

That is, the light emitted by the sensor portion 510 is reflected by the passage operation portion 120 or the contents 5 depending on whether the contents are discharged through the passage space 112c.

In this case, the sensing control portion 520 detects a time difference between a time of emitting light through the sensor portion 510 and a time of receiving the light by the sensor portion 510, compares the time difference with a preset set value, determines that the contents 5 have passed through the passage space 112c when the time difference is within the set value, and determines that the contents 5 have not passed when the time difference exceeds the set value.

As described above, the sensing control portion 520 generates medication-taking state information on the basis of a result of sensing the contents 5 and transmits the generated medication-taking state information to the medication-taking guide terminal 600.

Meanwhile, the medication-taking guide terminal 600 continuously collects the medication-taking state information transmitted from the sensing control portion 520, generates medication-taking management information for the user by using the medication-taking state information and the medication-taking schedule information received from the medication-taking management server 700, and outputs the generated medication-taking management information through the output portion 620.

That is, the medication-taking guide terminal control portion 630 compares the medication-taking state information and the medication-taking schedule information and generates and outputs the medication-taking management information according to a result of comparing them. Here, the medication-taking guide terminal control portion 630 checks whether the user does not take a fixed quantity of the contents 5, does not take the contents 5 at a fixed medication-taking time, or does not take the contents 5, that is, whether the user abuses or misuses medication and outputs a result of checking such information (S240 and S250).

In this case, the medication-taking guide terminal control portion 630 may output a text message or a voice which guides taking the contents at a fixed medication-taking time when the user does not take the contents 5 at the medication-taking time and may output a text message or a voice which guides taking a fixed dosage when the user does not take the fixed dosage.

In addition, when the medication-taking state information is transmitted from the sensor terminal as described above, the medication-taking guide terminal control portion 630 accumulates and stores the medication-taking state information and generates medication-taking history information by using the medication-taking state information.

Also, as shown in FIGS. 4 and 19, the contents movement device 1 may include the sensor module 500 which senses a passage of the contents when the contents pass through the contents passage means 123. The sensor module 500 senses or measures at least one of a quantity of passing contents, a date, a day of the week, and a time.

Contents measurement by the sensor module 500 may be performed by an electronic sensor or a mechanical operation. The sensor module 500 may measure physical movement of the contents passage means 123 by using a mechanical measurement method. The sensor module 500 includes at least one type of sensing equipment such as a touch sensor, an acceleration sensor, an angular speed sensor, a gravitational sensor, a terrestrial magnetism sensor, a gyroscope sensor, a proximity sensor, an operation-recognition sensor, an electronic compass, a magnetometer sensor, and a gesture sensor.

Also, there is included a display portion 800 which recognizably displays data sensed or measured by the sensor module 500 or whether contents have passed through the passage operation portion 120 by the operation of the contents passage means 123 by using at least one of sense of sight, hearing, and touch of the user. The display portion 800 may display at least one of numbers, letters, symbols, Braille, light emission, lighting, and colors.

Meanwhile, when the sensor module 500 senses that a certain quantity of contents pass through the contents passage means 123 in a certain period or time or an excessive quantity of contents pass through the contents passage means 123, there is included a control portion (not shown) which restricts an operation of the contents passage means 123 for moving the contents.

The sensor module 500 which senses a passage of contents when the contents pass through the contents passage means 123 may be included. It is determined whether the contents pass through or a passage quantity is sensed by the sensor module 500. Whether the contents pass or the passage quantity or whether the contents pass or the passage quantity with at least one of a date, a day of the week, a time of passage may be displayed on the display portion 800. The display portion 800 may display at least one of numbers, letters, symbols, and signals by using a liquid crystal display (LCD) or a light emitting diode (LED).

A communication portion which transmits the data sensed or measured by the sensor module 500 may be included. Whether the contents pass or the passage quantity sensed by the sensor module 500 may be determined, and whether the contents pass, the passage quantity, or whether the contents pass or the passage quantity with at least one of a date, a day of the week, a time of passage may be closely or remotely transmitted through the communication portion.

Also, a locking portion may be included so as to not pass further contents when the sensor module 500 senses the contents which pass through the contents passage means 123 and it is determined that a fixed quantity of contents have passed. The locking portion is provided in the passage device to prevent movement of the contents passage means 123 or block a movement path of the contents in the passage operation portion 120.

Here, the blocking of movement in the contents passage means 123 may be performed by resisting contact with a moving part of the contents passage means, and the movement path in the passage operation portion 120 may be blocked by blocking or resisting the contents at the passage path portion provided at a passage entry side and a passage discharge side of the contents. The locking portion may maintain a locked state before a designated time or an end of a situation when control is necessary such as a case of medication to be taken by a person with dementia which should be restricted, or foodstuffs which should be restricted in intake of an ordinary person.

Also, at least one of numbers, letters, and symbols is displayed on a surface of the contents or inside the contents such that it is possible to observe a display about the contents which have passed through the contents passage means 123 or the contents which have not passed through the contents passage means 123.

FIG. 20 is a data flowchart of a medication-taking data management system according to the second embodiment of the present invention. Here, ① when a user takes prescriptive medication through a fixed quantity discharge smart medication dispenser, a patient who takes medication passes a fixed quantity of contents in a container by only an operation of tilting a medication container so as to discharge medication or a supplement having a tablet shape one by one, which is simple, hygienic, and prevents degeneration of contents, ② since sensing data may be collected by using a medication discharge sensor attached to the dispenser, a medication dispenser for systematically managing medication-taking of a patient is developed by attaching a sensor for checking whether medication is discharged to the dispenser, ③ after the sensing data is primarily collected by using a smart phone, a PC, or the like of a user on the basis of a communication module, ④ primary information is processed to be secondary information by a data and application program server and is provided to a person concerned, ⑤ a related organization analyzes medication-taking information data and transmits medication-taking guidance items to the user such that a remote medication-taking management system utilizing the same may be constructed.

Particularly, a medication discharge checking sensor may be attached to manage medication taking. Communication equipment using the medication discharge checking sensor, Bluetooth, and the like for checking a medication-taking state, which is a mandatory item, may be attached. Also, for cost reduction and manufacturing effectiveness, an integrated sensor and communication-integrated device may be designed and applied.

To maximize an effect of treating illness, not only a medical team (a doctor and a pharmacist) which is a subject of medical practice but also a patient who uses medical services needs active performance of a duty of the patient with respect to the medical practice, which is available using a remote medication-taking system like the embodiment.

Data collected by the sensor attached to the medication dispenser may be primarily collected by using specialized equipment such as a smart phone or a one board computer through the communication module. The primarily collected information may be transmitted to a server and secondary information collected by the server may be processed to be provided to a doctor, a pharmacist, National Health Service (NHS), and the like.

The smart phone or the specialized equipment may notify the patient of an obligation to take medication, continuously notify an administration time and a dosage, and may transmit continuous warnings when the patient does not take medication. For patients who can not use a smart phone such as the elderly and the like, the specialized equipment using the one board computer (for example, Raspberry Pi) in which Bluetooth and wireless fidelity (Wi-Fi) are built may be configured.

FIG. 21 is a flowchart illustrating an application of a medication-taking data management technology according to the second embodiment of the present invention, and a smart medication dispenser attached to medication discharge equipment such as M1 includes a discharger, a sensor, and a Bluetooth communication module. M1 may communicate with an M2-1 (mobile equipment: a smart phone) or M2-2 (fixed equipment: a one board computer) through c1 (Bluetooth communications). Also, M2-1 and M2-2 may communicate with M3 (a server) through C2 (a network).

M3 communicates with Ex1 (a related organization server) through C3 (connected by an open-API or EAI). Here, C1 performs discharge amount transmission and an error or confirm signal transmission. C2 allows m2 to transmit a discharge amount to m3 and allows m3 to transmit medication-taking management content to m2. C3 allows m3 to transmit discharge amount statistics to Ex1 and allows Ex1 to transmit medication-taking management content to M3. C3 communication connects using the open-API or EAI which is a heterogeneous DB connection protocol.

Figure 22:
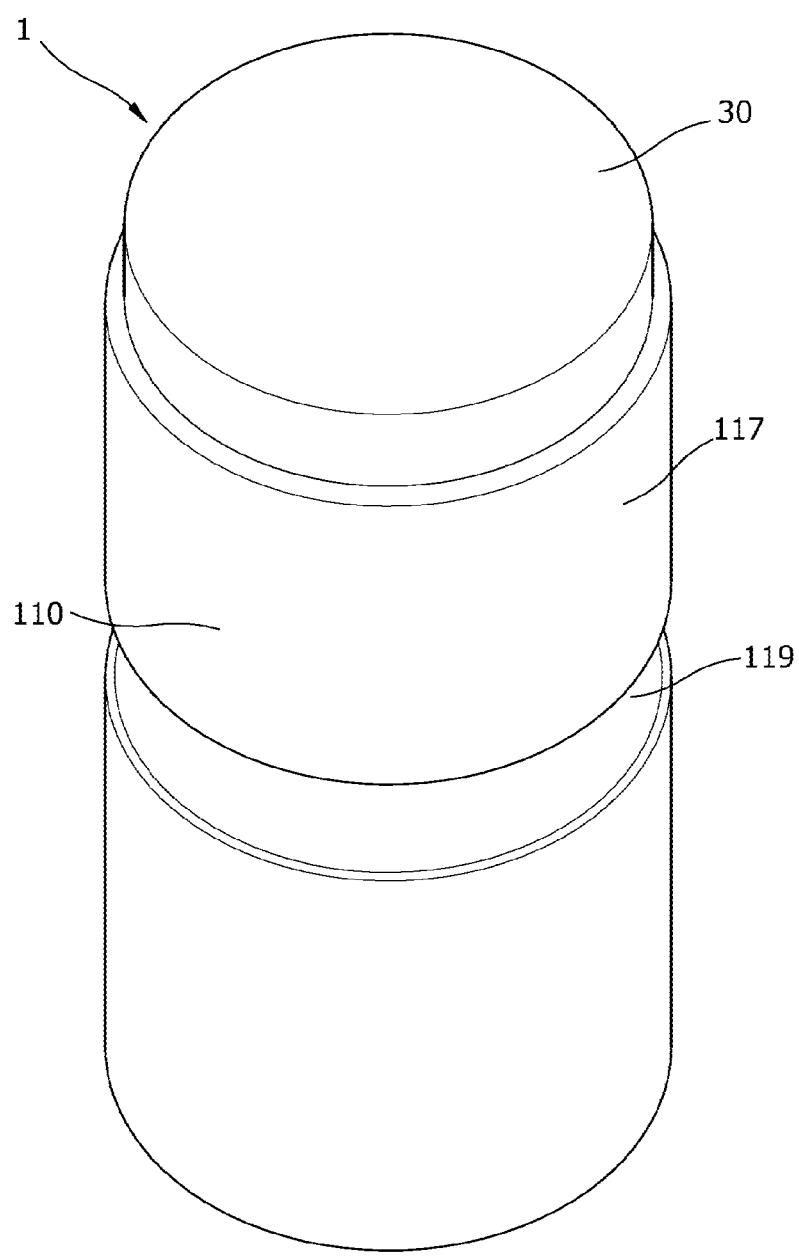
FIG. 22 is a perspective view of a contents movement device including a passage device according to a third embodiment of the present invention.
Figure 23:
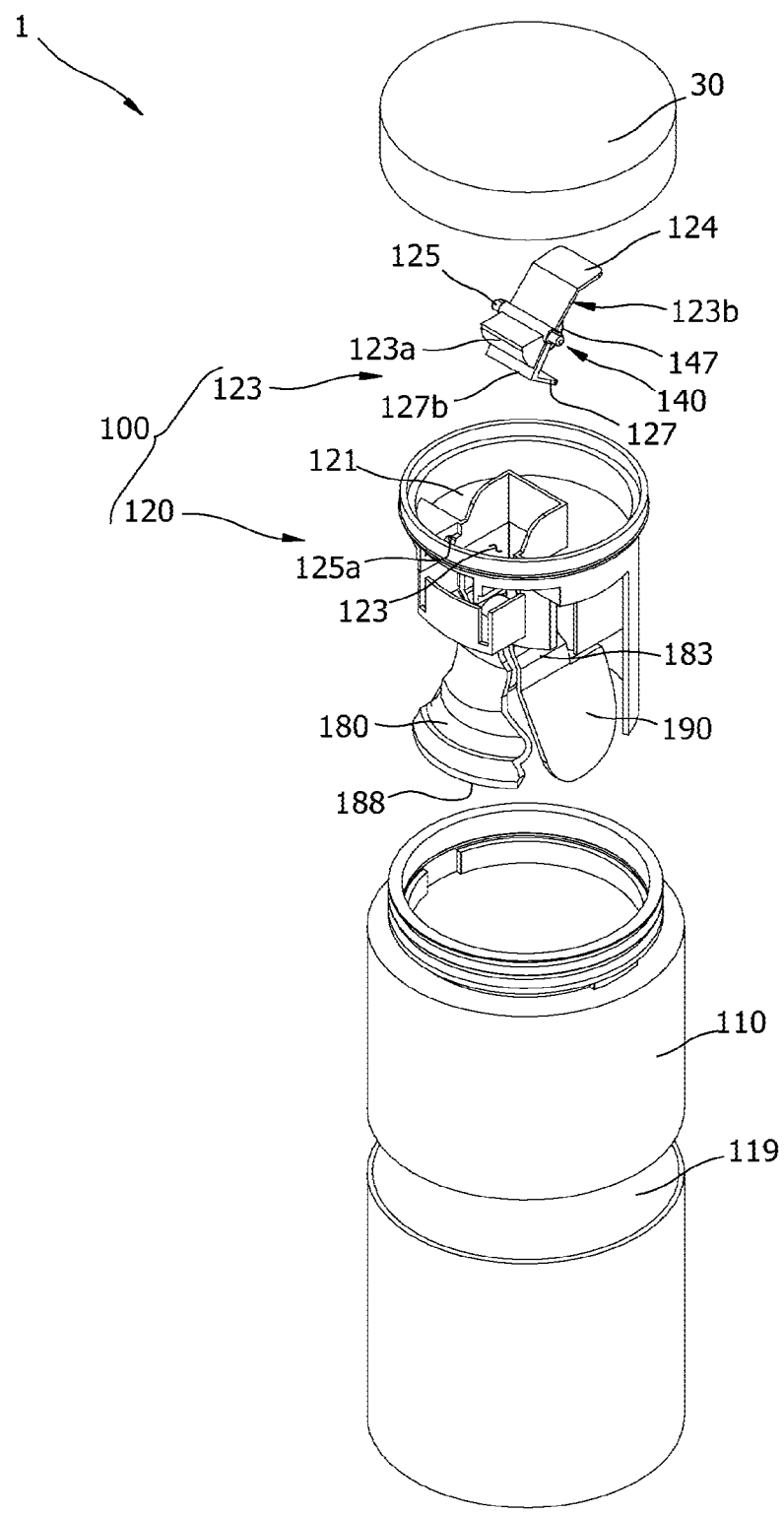
FIG. 23 is an exploded perspective view of the contents movement device including the passage device according to the third embodiment of the present invention.

FIG. 22 is a perspective view of a contents movement device including a passage device according to a third embodiment of the present invention, and FIG. 23 is an exploded perspective view of the contents movement device including the passage device according to the third embodiment of the present invention.

Figure 24:
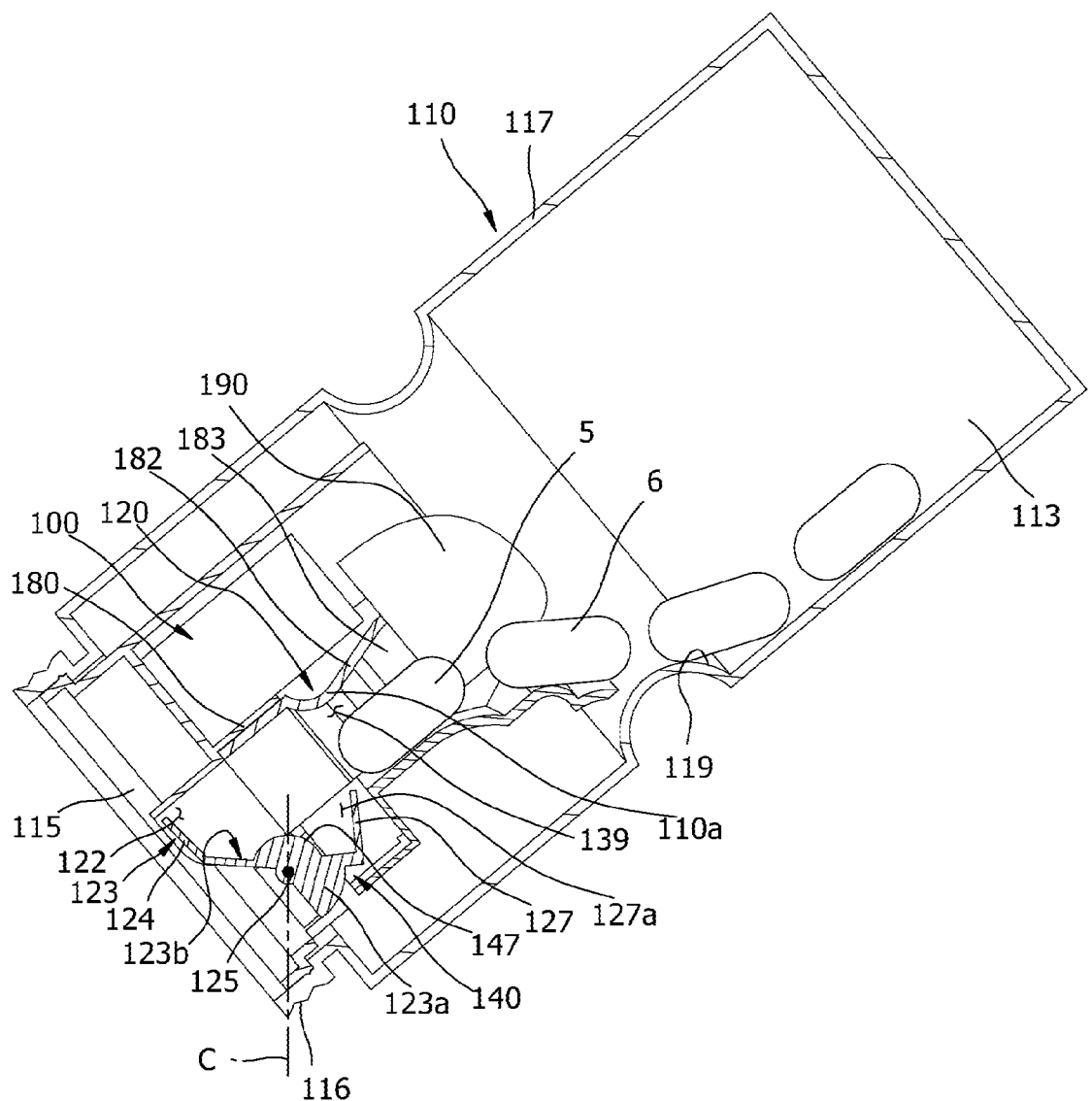
FIG. 24 is a cross-sectional view of the contents movement device including the passage device according to the third embodiment of the present invention.
Figure 25:
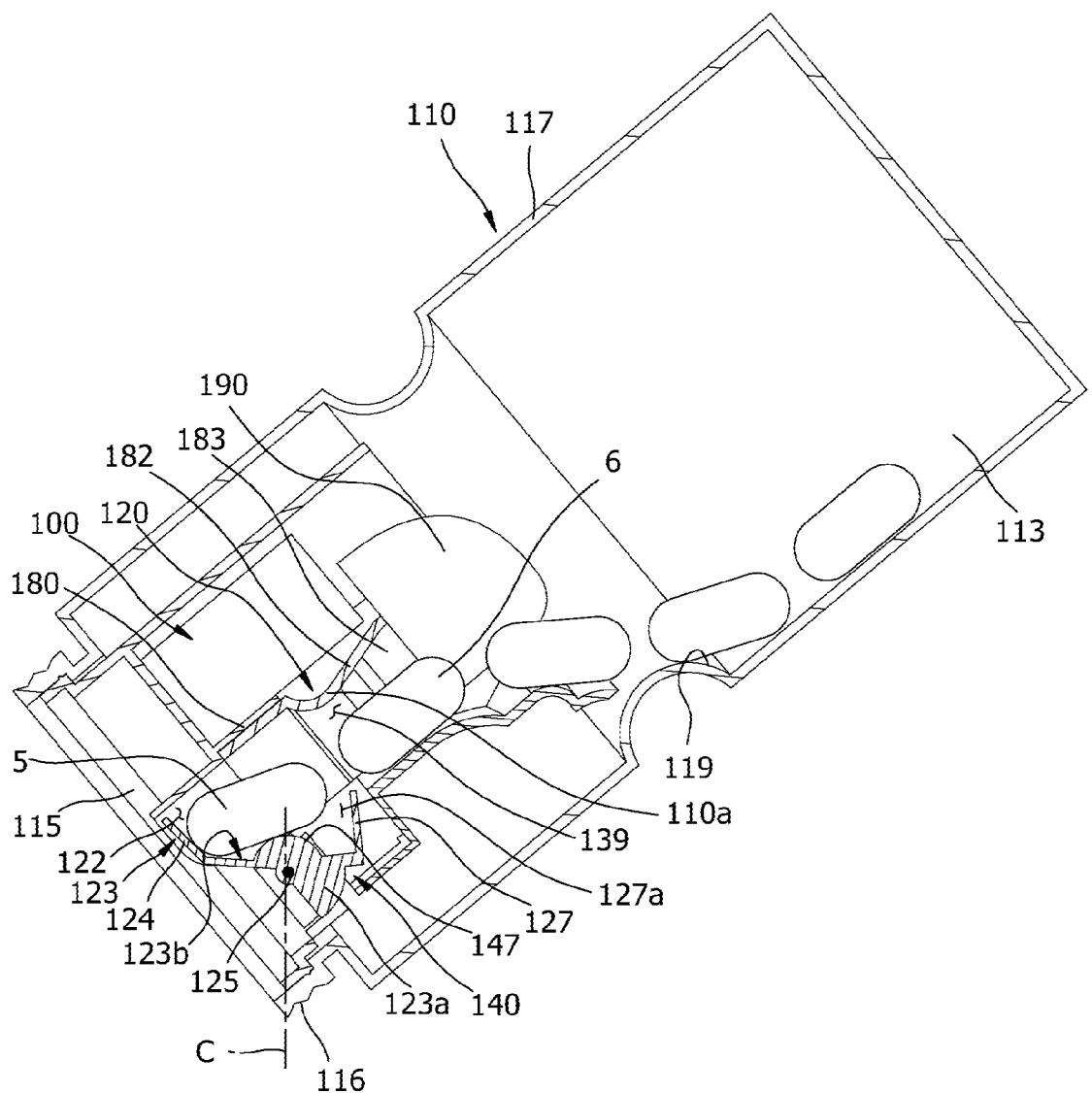
FIG. 25 is a cross-sectional view illustrating a state in which a housing of the contents movement device including the passage device tilts according to the third embodiment of the present invention.
Figure 26:
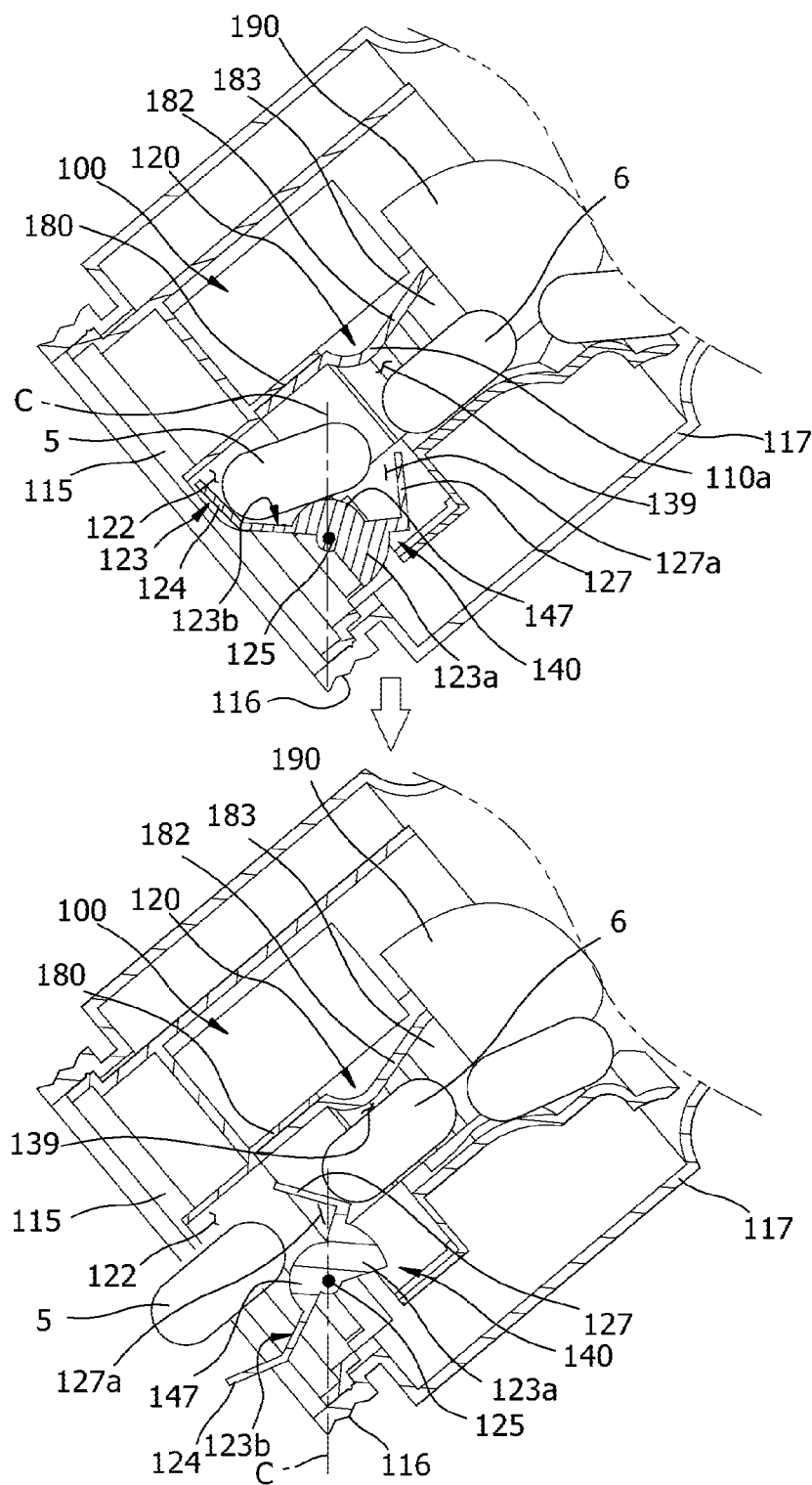
FIG. 26 is a cross-sectional view illustrating a state in which the contents movement device including the passage device is used according to the third embodiment of the present invention.

FIG. 24 is a cross-sectional view of the contents movement device including the passage device according to the third embodiment of the present invention, FIG. 25 is a cross-sectional view illustrating a state in which a housing of the contents movement device including the passage device according to the third embodiment of the present invention tilts, and FIG. 26 is a cross-sectional view illustrating a state in which the contents movement device including the passage device is used according to the third embodiment of the present invention.

As shown in FIGS. 22 to 26, the contents movement device 1 including the passage device 100 according to the third embodiment of the present invention includes the housing 110, the passage operation portion 120, and the supply guide portion 119.

Description of the passage operation portion 120 will be replaced by the above description.

Also, the housing 110 is a container which stores the contents 5, includes the passage operation portion 120 therein, and forms the supply guide portion 119.

Particularly, the housing 110 has an approximately cylindrical shape, holds the fixing member 121, and guides the contents 5 to move toward the movement guide portion 180 through the supply guide portion 119.

Here, the supply guide portion 119 convexly protrudes from an inner surface of the housing 110, which is close to an end of the contents induction portion 188, to form a curvature.

Then, when the housing 110 tilts, a preset quantity of the contents 5 is guided to move into the contents induction portion 188 and the guide member 190.

Of course, the supply guide portion 119 is modifiable to a variety of shapes.

In addition, the contents induction portion 188 or the passage operation portion 120 may be supported by the supply guide portion 119.

In the case of an injection-blown container, when the supply guide portion 119 is not provided, in addition to a step between the contents induction portion 188 and an inner diameter of the reduced-diameter portion 116 which is a neck of the container, the contents induction portion 188 having an incline, being bent, or having a step and connecting steps obtained by adding all steps between the reduced-diameter portion 116 and the enlarged-diameter portion 117 should be present. However, in this case, it is impossible to insert the passage device into the container at once in one direction during assembling.

In the embodiment, like the first embodiment, the contents induction portion 188 of the passage device 100 allows the guide member 190 and a beginning point of the contents induction portion 188, which is close to the inner diameter of the housing, to be located inside the reduced-diameter portion 116 such that the passage device 100 is directly insertable into the housing 110 in one direction during assembling.

Unlike the first embodiment, the beginning point of the step connection portion 188 of the passage device 100 is connected to be close to an inner wall of the enlarged-diameter portion 117 which is a container body, not an inner wall of the reduced-diameter portion 116, such that it is unnecessary for the reduced-diameter portion 116 (a neck of the container) to surround the entire length of the contents induction portion 188.

In the embodiment, the supply guide portion 119, which is located to be connected to the beginning end of the step connection portion of the contents induction portion 188 and has a shape concavely curved in the enlarged-diameter portion 117 of the container body 110, may be provided, and movement of the contents is smoothly performed through the supply guide portion 119 such that the contents slide and are guided to move from the container body 110 to the passage path portion 139 of the passage device 100.

Like the embodiment, when the contents induction portion 188 of the passage device 100 allows the beginning point of the step connection portion 188 which faces a bottom of the container to be located in the enlarged-diameter portion 117 and includes the step connection portion close to the beginning point of the step connection portion which faces the bottom of the container, the movement of the contents is connected to smoothly enter the contents induction portion 188 from the enlarged-diameter portion 117 through the step connection portion.

Description of unstated reference numerals will be replaced by the above description.

Figure 27:
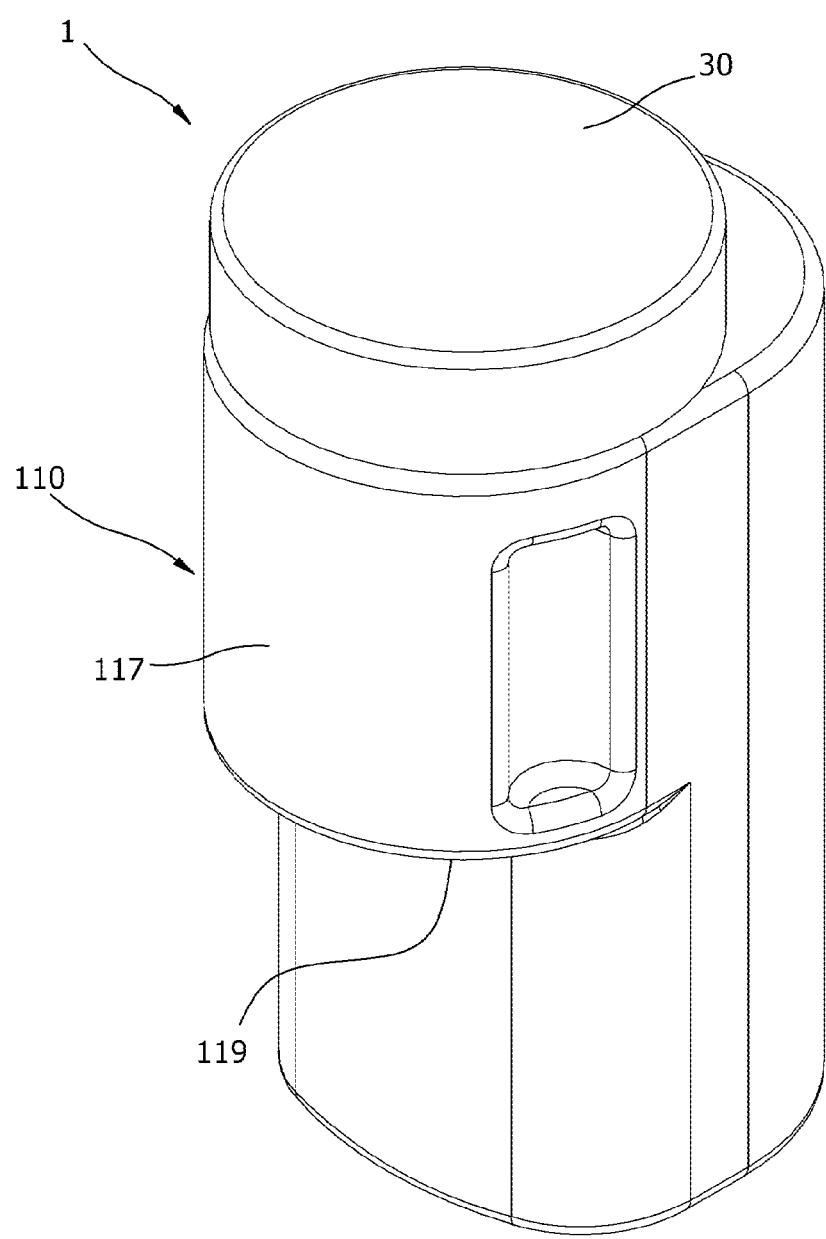
FIG. 27 is a perspective view of a contents movement device including a passage device according to a fourth embodiment of the present invention.
Figure 28:
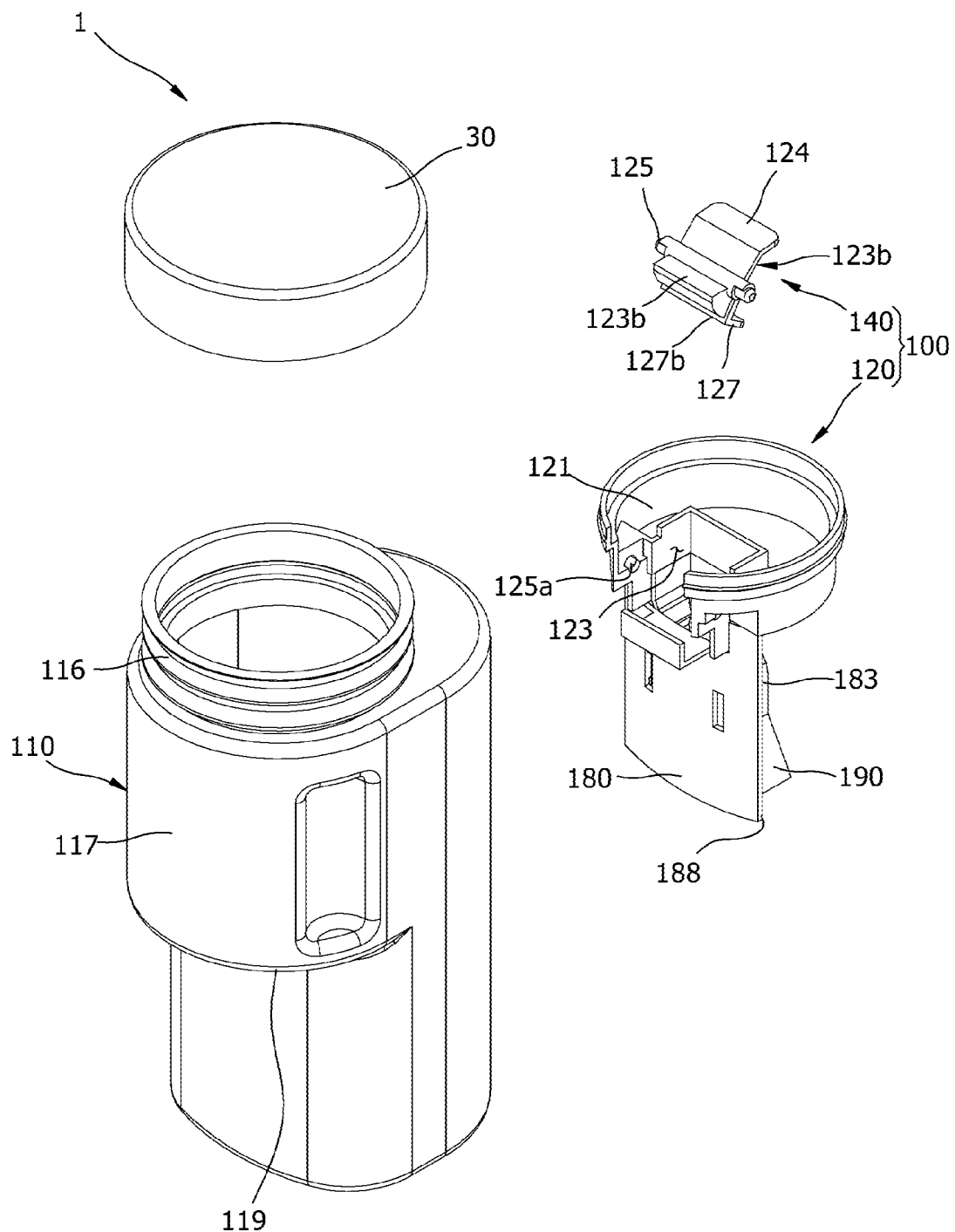
FIG. 28 is an exploded perspective view of the contents movement device including the passage device according to the fourth embodiment of the present invention.

FIG. 27 is a perspective view of a contents movement device including a passage device according to a fourth embodiment of the present invention, and FIG. 28 is an exploded perspective view of the contents movement device including the passage device according to the fourth embodiment of the present invention.

Figure 29:
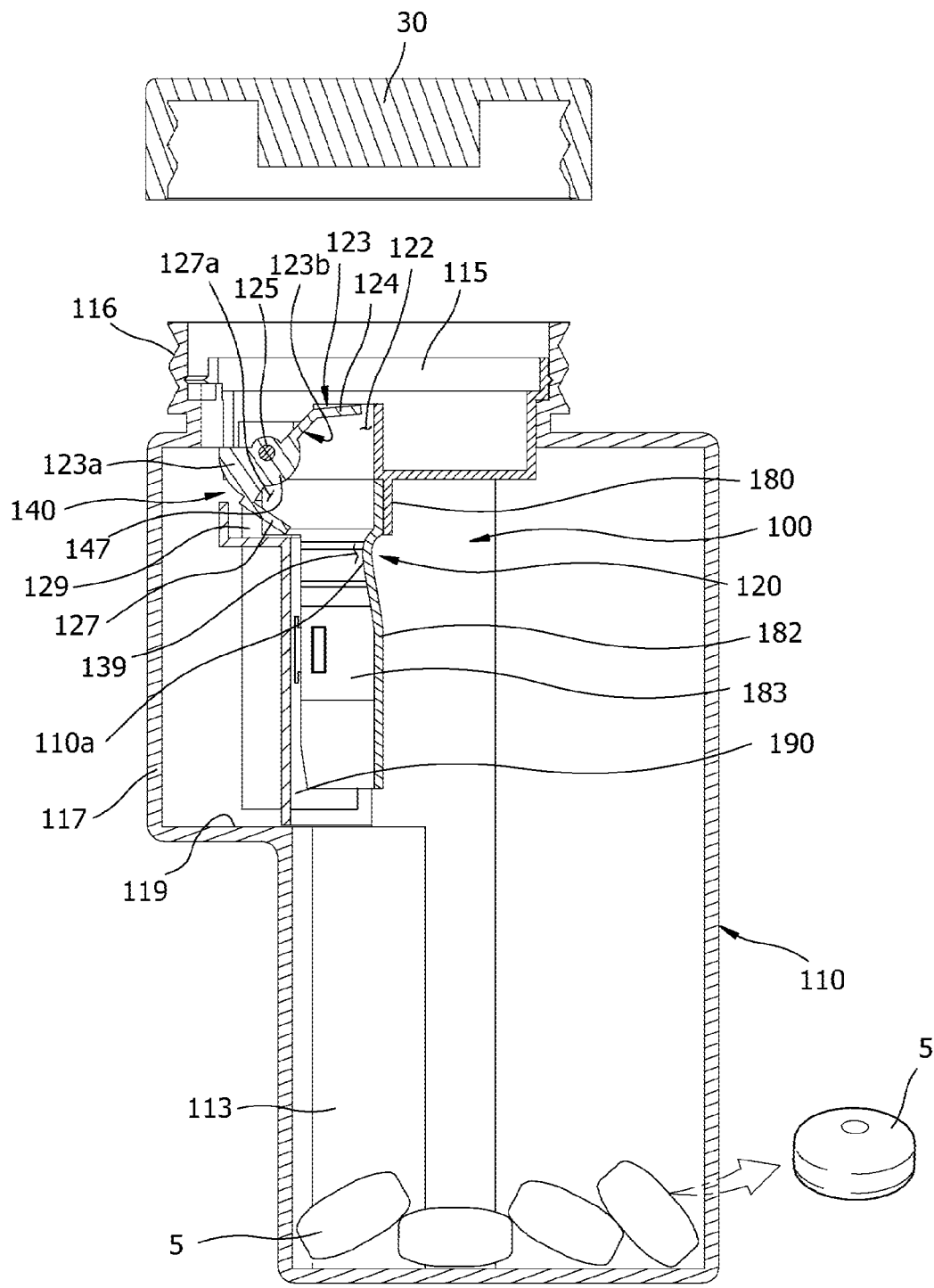
FIG. 29 is a side cross-sectional view of the contents movement device including the passage device according to the fourth embodiment of the present invention.
Figure 30:
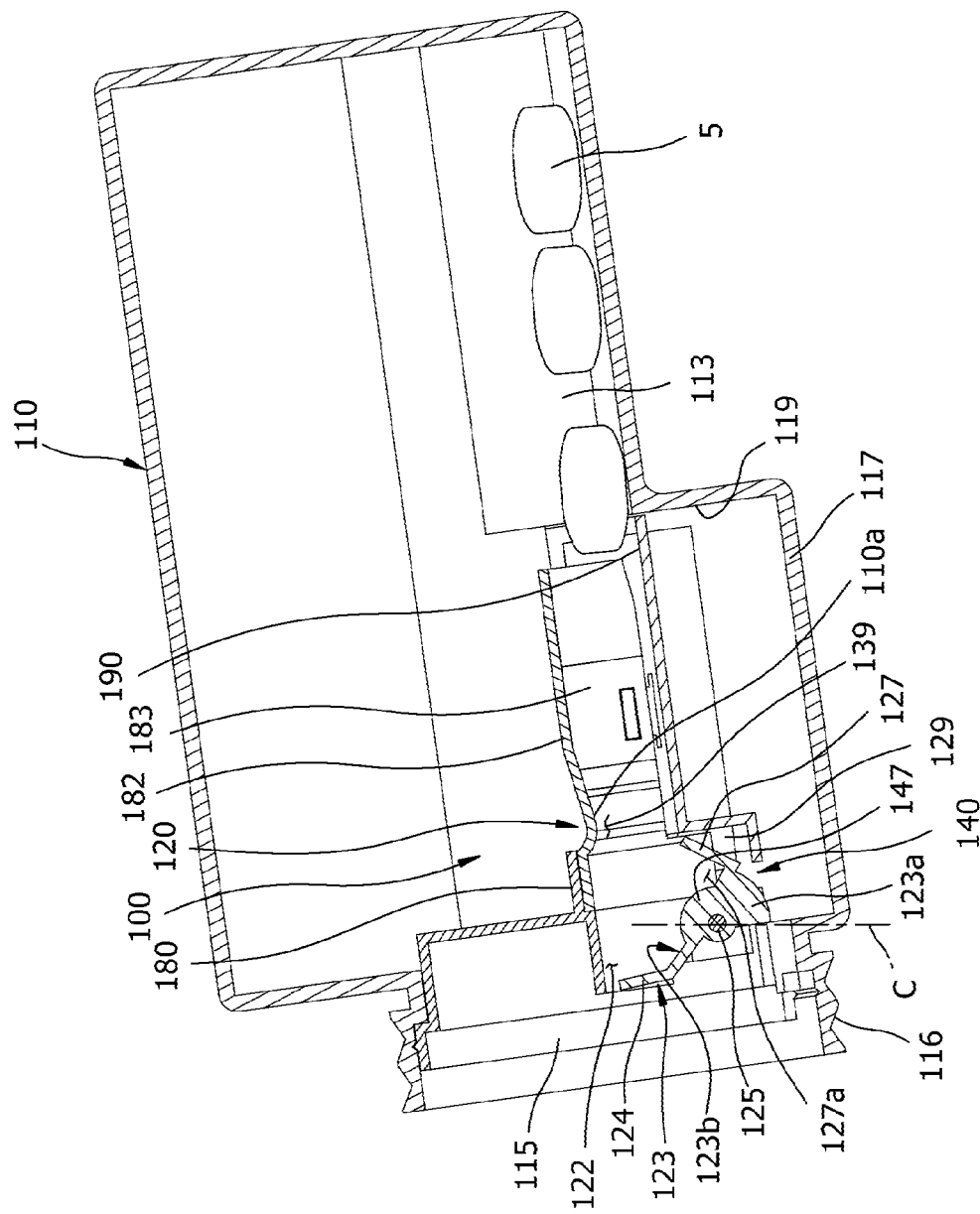
FIG. 30 is a side cross-sectional view illustrating a tilt of the contents movement device including the passage device while contents do not pass therethrough according to the fourth embodiment of the present invention.
Figure 31:
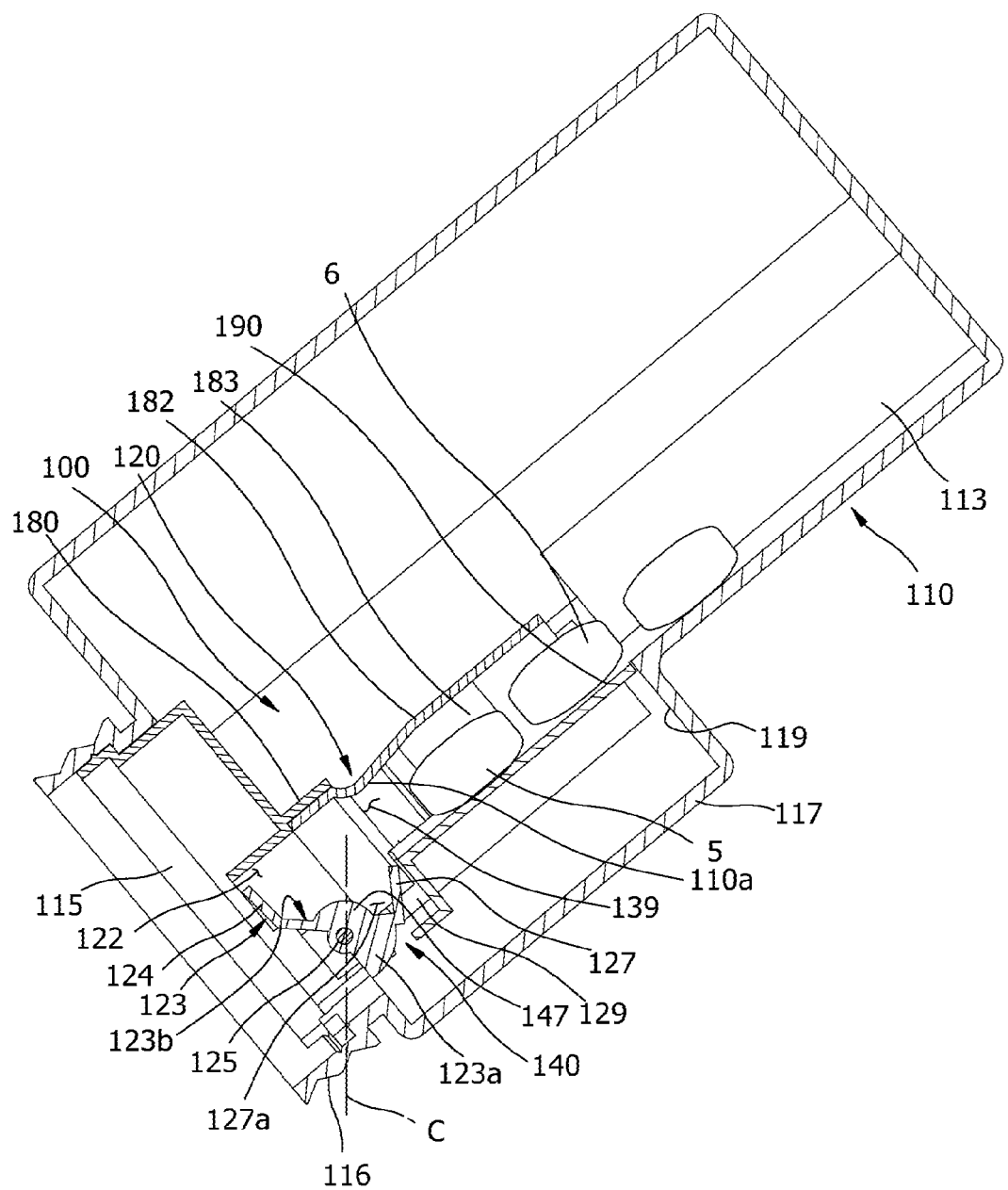
FIG. 31 is a side cross-sectional view illustrating a tilt of the contents movement device including the passage device in a contents passage state according to the fourth embodiment of the present invention.
Figure 32:
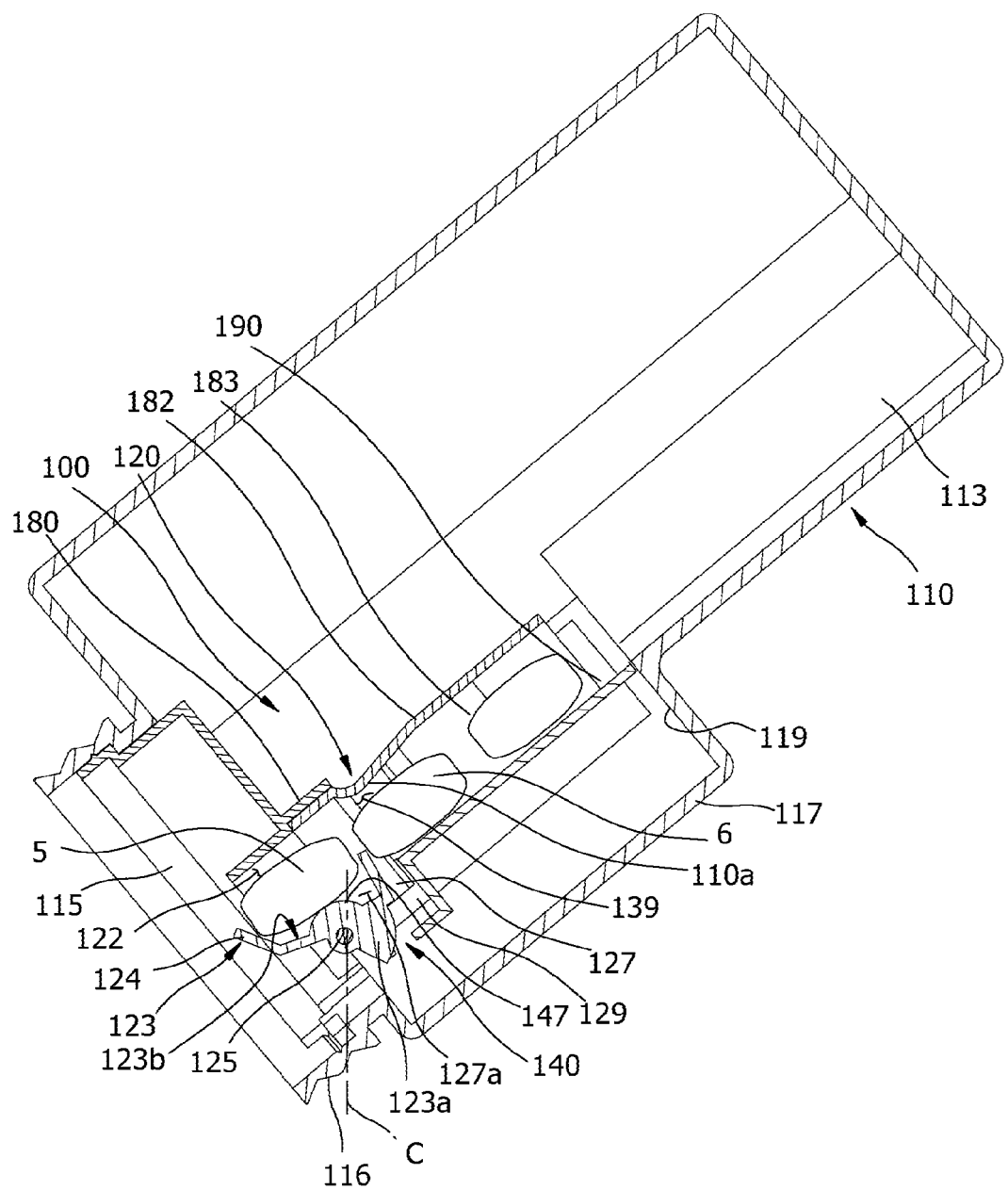
FIG. 32 is a side cross-sectional view illustrating a tilt of the contents movement device including the passage device in a contents passage state and an blocking state according to the fourth embodiment of the present invention.

FIG. 29 is a side cross-sectional view of the contents movement device including the passage device according to the fourth embodiment of the present invention, FIG. 30 is a side cross-sectional view illustrating a tilt of the contents movement device including the passage device while contents do not pass therethrough according to the fourth embodiment of the present invention, FIG. 31 is a side cross-sectional view illustrating a tilt of the contents movement device including the passage device in a contents passage state according to the fourth embodiment of the present invention, and FIG. 32 is a side cross-sectional view illustrating a tilt of the contents movement device including the passage device in a contents passage state and an blocking state according to the fourth embodiment of the present invention.

Figure 33:
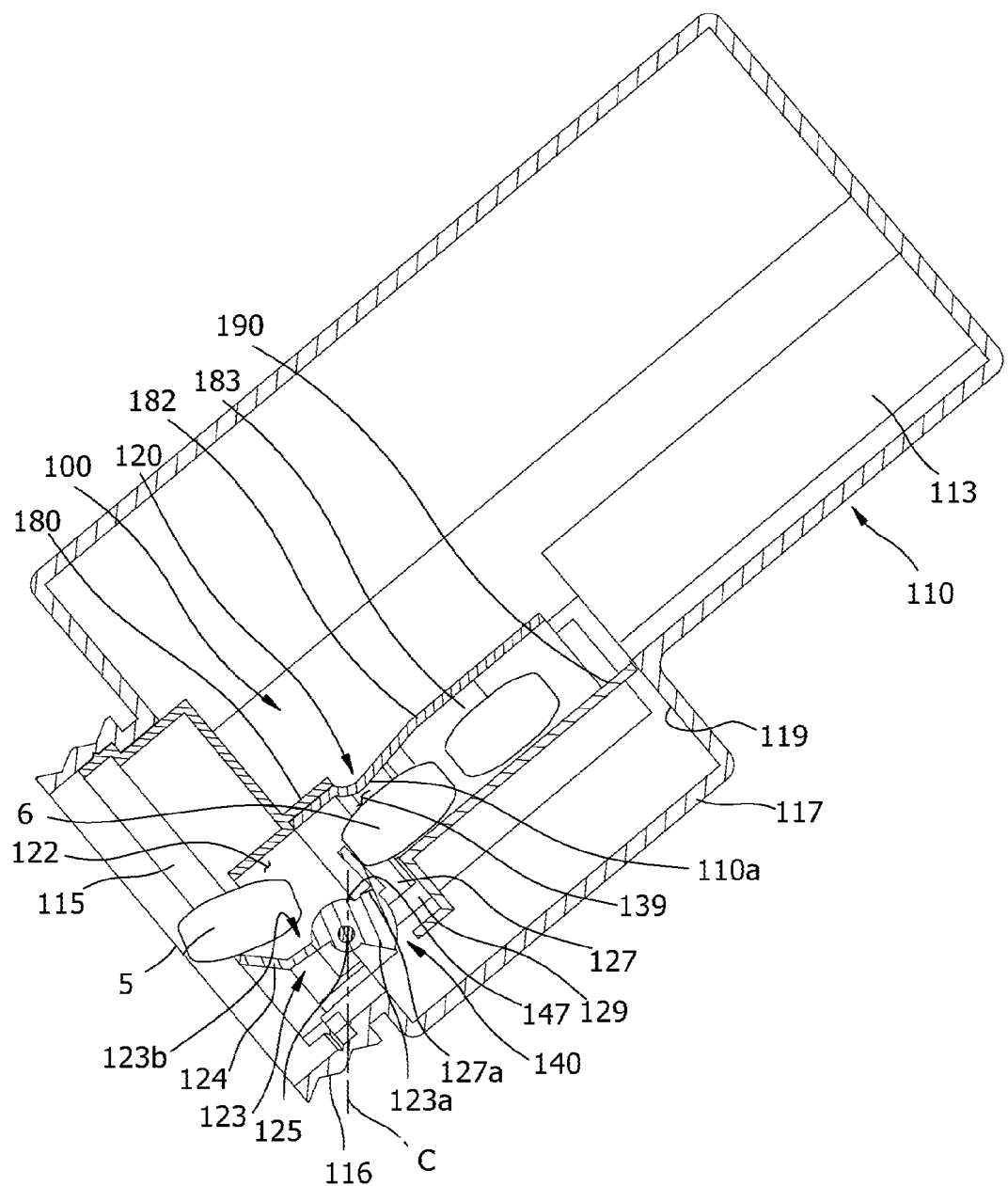
FIG. 33 is a side cross-sectional view illustrating a tilt of the contents movement device including the passage device in a contents blocking state and a passage state according to the fourth embodiment of the present invention.
Figure 34:
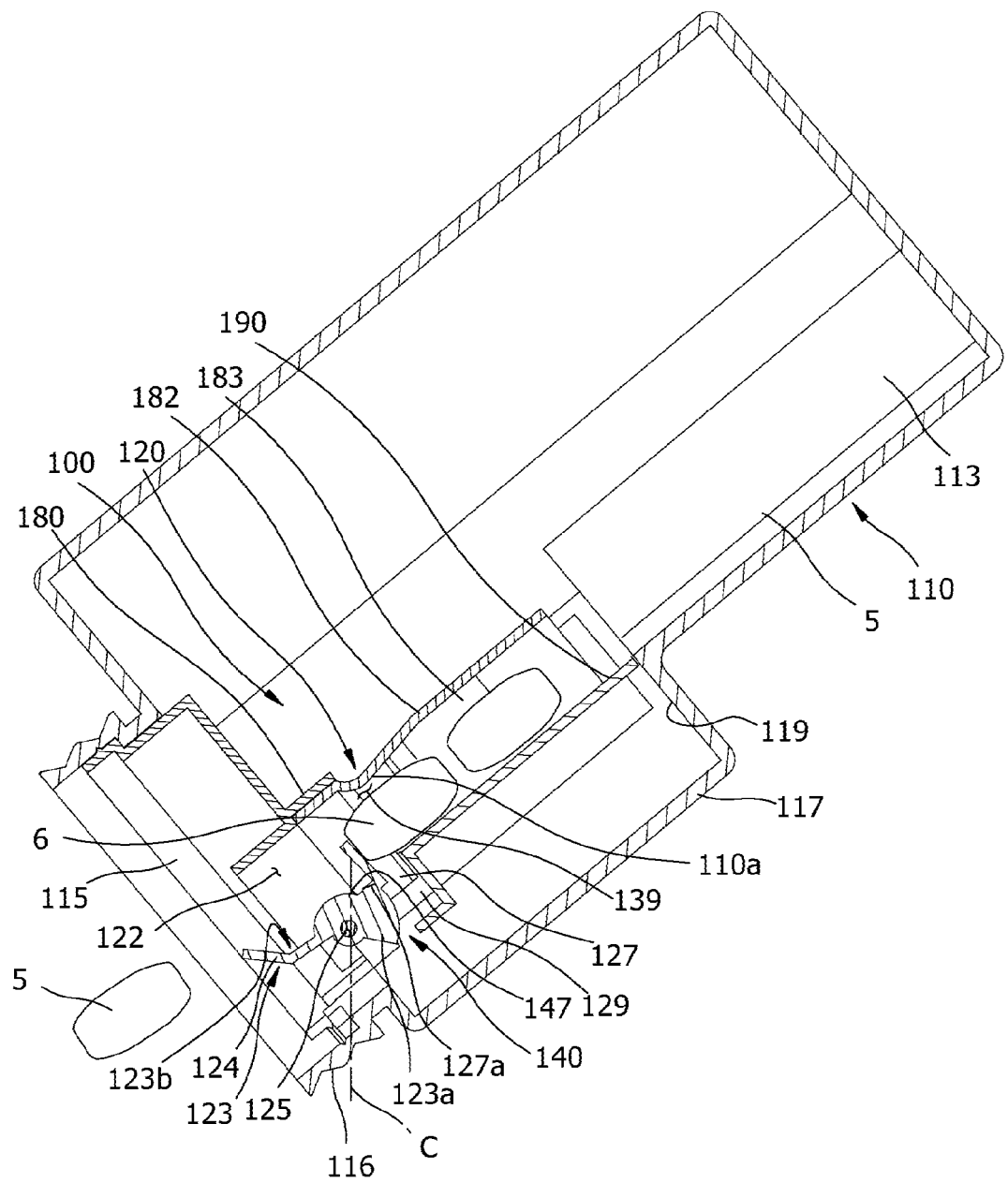
FIG. 34 is a side cross-sectional view illustrating a tilt of the contents movement device including the passage device in a contents blocking state and a complete passage state according to the fourth embodiment of the present invention.
Figure 35:
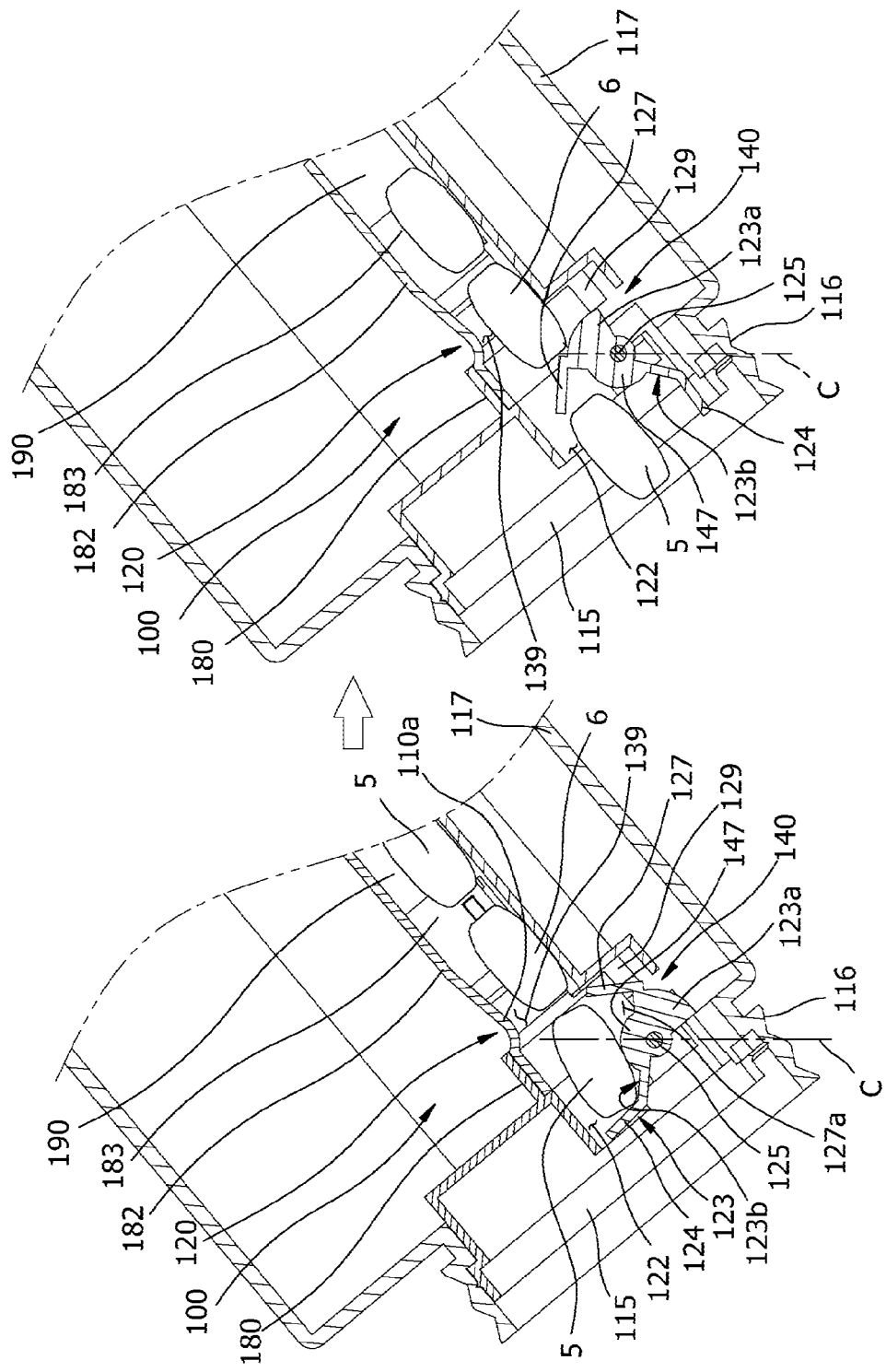
FIG. 35 is a side cross-sectional view illustrating a state of using the contents movement device including the passage device according to the fourth embodiment of the present invention.

FIG. 33 is a side cross-sectional view illustrating a tilt of the contents movement device including the passage device in a contents blocking state and a passage state according to the fourth embodiment of the present invention, FIG. 34 is a side cross-sectional view illustrating a tilt of the contents movement device including the passage device in a contents blocking state and a complete passage state according to the fourth embodiment of the present invention, and FIG. 35 is a side cross-sectional view illustrating a state of using the contents movement device including the passage device according to the fourth embodiment of the present invention.

Figure 36:
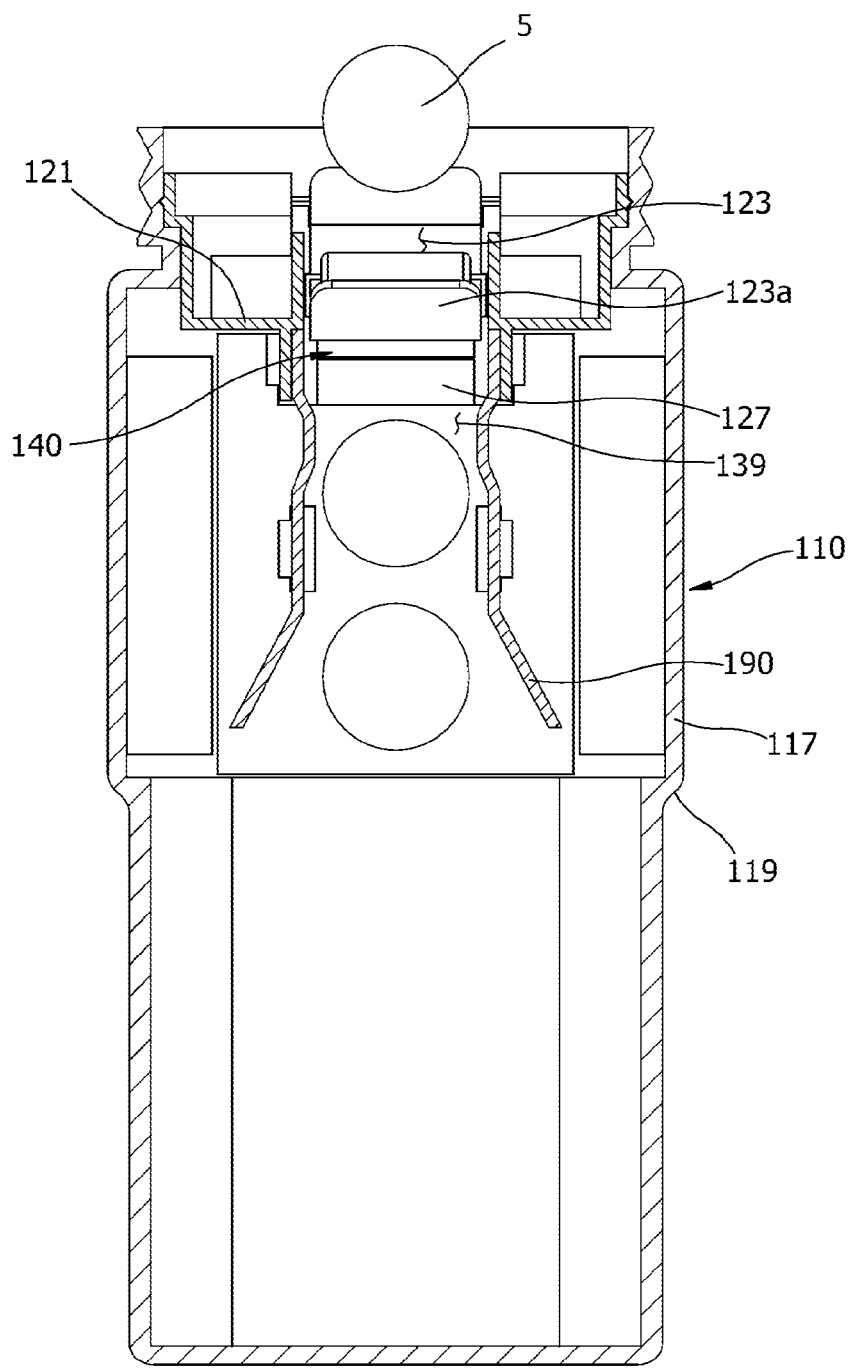
FIG. 36 is a front cross-sectional view of the contents movement device including the passage device according to the fourth embodiment of the present invention.

FIG. 36 is a front cross-sectional view of the contents movement device including the passage device according to the fourth embodiment of the present invention.

Figure 37:
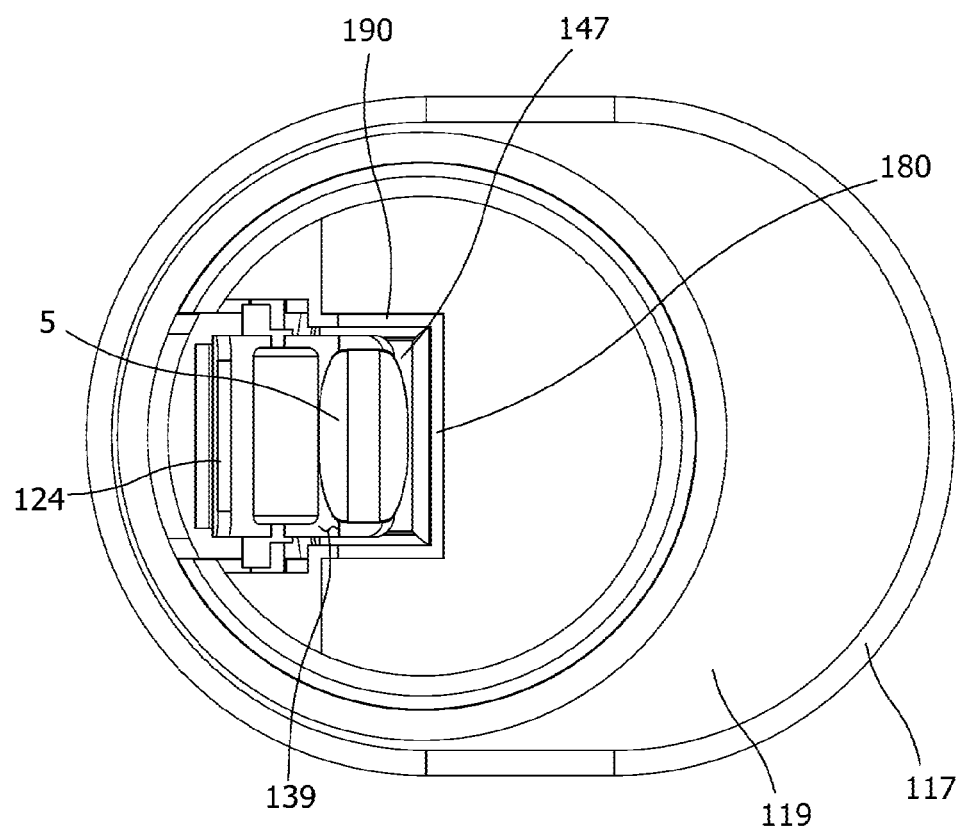
FIG. 37 is a bottom cross-sectional view of the contents movement device including the passage device according to the fourth embodiment of the present invention.

FIG. 37 is a bottom cross-sectional view of the contents movement device including the passage device according to the fourth embodiment of the present invention.

Figure 38:
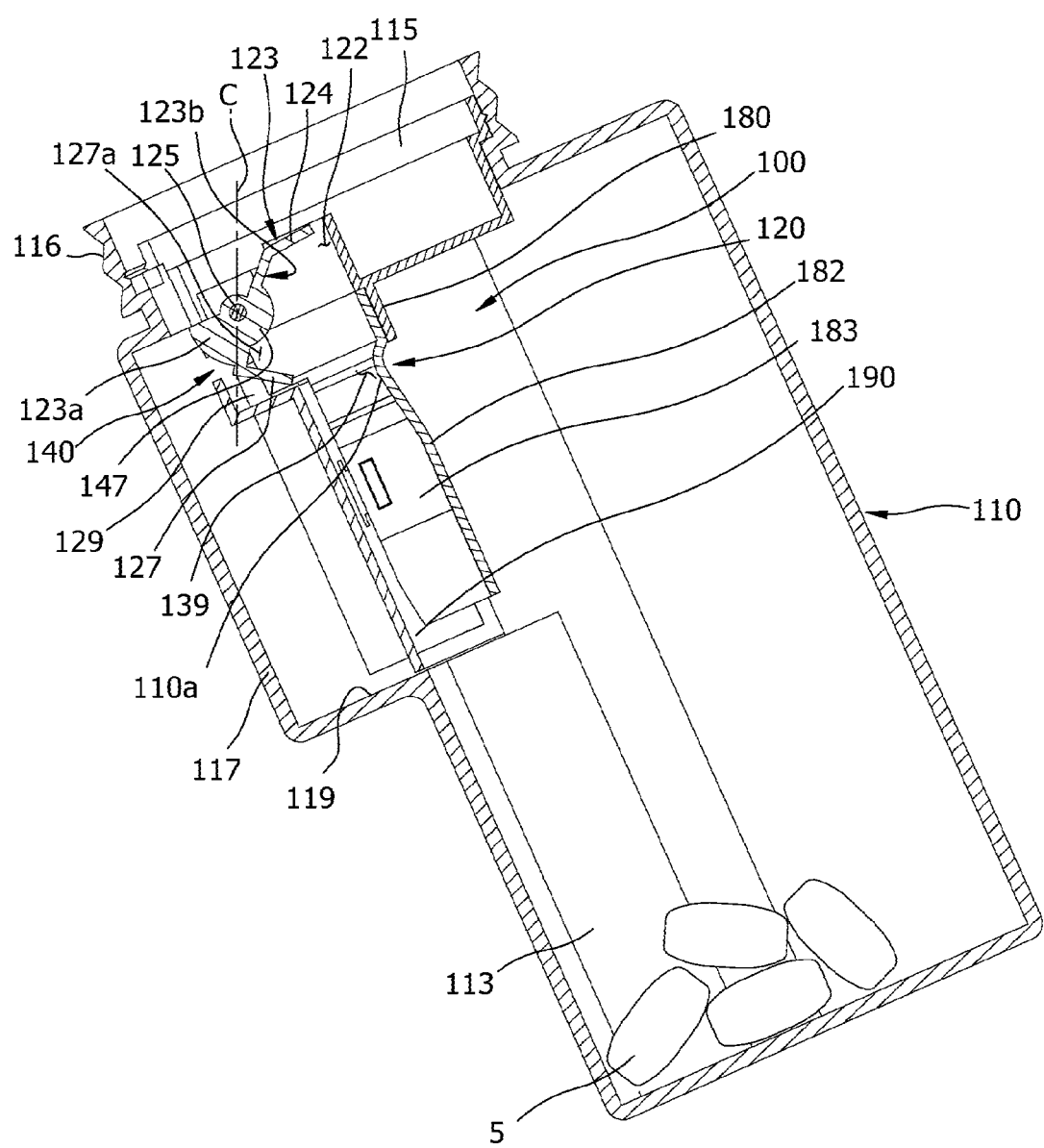
FIG. 38 is a side cross-sectional view illustrating that the passage device remains in an initial state while the contents movement device tilts at a certain angle according to the fourth embodiment of the present invention.

FIG. 38 is a side cross-sectional view illustrating that the passage device remains in an initial state while the contents movement device tilts at a certain angle according to the fourth embodiment of the present invention.

As shown in FIGS. 27 to 38, the contents movement device 1 including the passage device 100 according to the fourth embodiment of the present invention includes the housing 110, the passage operation portion 120, and the supply guide portion 119.

Description of the passage operation portion 120 will be replaced by the above description.

The housing 110 includes the enlarged-diameter portion 117 and the reduced-diameter portion 116.

The enlarged-diameter portion 117 holds the fixing member 121 and has an enlarged diameter to guide the contents 5 to move toward the movement guide portion 180.

Also, the enlarged-diameter portion 117 forms the supply guide portion 119 to guide the contents 5 to move toward the movement guide portion 180.

Here, the supply guide portion 119 supports an end of the movement guide portion 180 which is disposed to be at a height equal or similar to that of the supply guide portion 119 to guide the movement of the contents 5. Particularly, the contents 5 may have a circular and flat shape.

Of course, the supply guide portion 119 is modifiable to a variety of shapes.

In the case of contents which are not an oblong tablet-shaped solid rather a flat tablet-shaped solid, when a path on which the contents slide toward the passage device 100 is curved, the solid may be made to stand and enter the contents induction portion 188 such that a passage of a fixed quantity thereof may not be easily performed. Accordingly, since it is necessary to provide an even sliding bottom in a section in which the flat solid slides, inner walls of the contents induction portion 188 and the container body 110 corresponding to the sliding bottom on which the contents slide to enter the contents induction portion 188 are connected with no curve or with a minimum curve.

Accordingly, the contents induction portion 188 is formed without a curve like the embodiment.

Also, in the case of an injection-blown container, the contents induction portion 188 has a shape with no curve and a space for disposing the passage movement portion 140 therein is necessary so as to be inserted at once. Accordingly, the supply guide portion 119 extends toward an outer circumference of the container body 117 to provide an available space into which the passage device 100 is inserted.

FIG. 29 illustrates a case of the contents 5 which are not tablets but flat.

In FIG. 30, when the supply guide portion 119 (a threshold) or a great curve is present, the contents 5 which are not a tablet but flat are made to stand while siding over the supply guide portion 119 and are unable to enter the passage path portion 139. Accordingly, unlike the above-described embodiment, the passage device 100 needs a continuous smooth sliding bottom. In the above-described embodiment, even when there is a step between the housing 110 and the guide member 190, the tablet contents 5 overcomes the step with a linearly directional movement property thereof and is movable. However, the flat contents 5 may not overcome the step and may be made to stand.

FIG. 36 illustrates that in the case of the contents 5 which are not tablets but flat, when a fixed quantity of the contents 5 is a single piece, a passage space of the passage path portion 139 may be configured to be a space with a lateral width which is greater than a width or equal to two time a width of one piece of the contents.

FIG. 37 illustrates that when the fixed quantity of the contents 5 is a single piece, the passage space is configured to be a space with a vertical height more than a height of one piece of the contents and less than two times thereof such that only the fixed quantity of contents may pass when the fixed quantity is a single piece.

Description of unstated reference numerals will be replaced by the above description.

Figure 39:
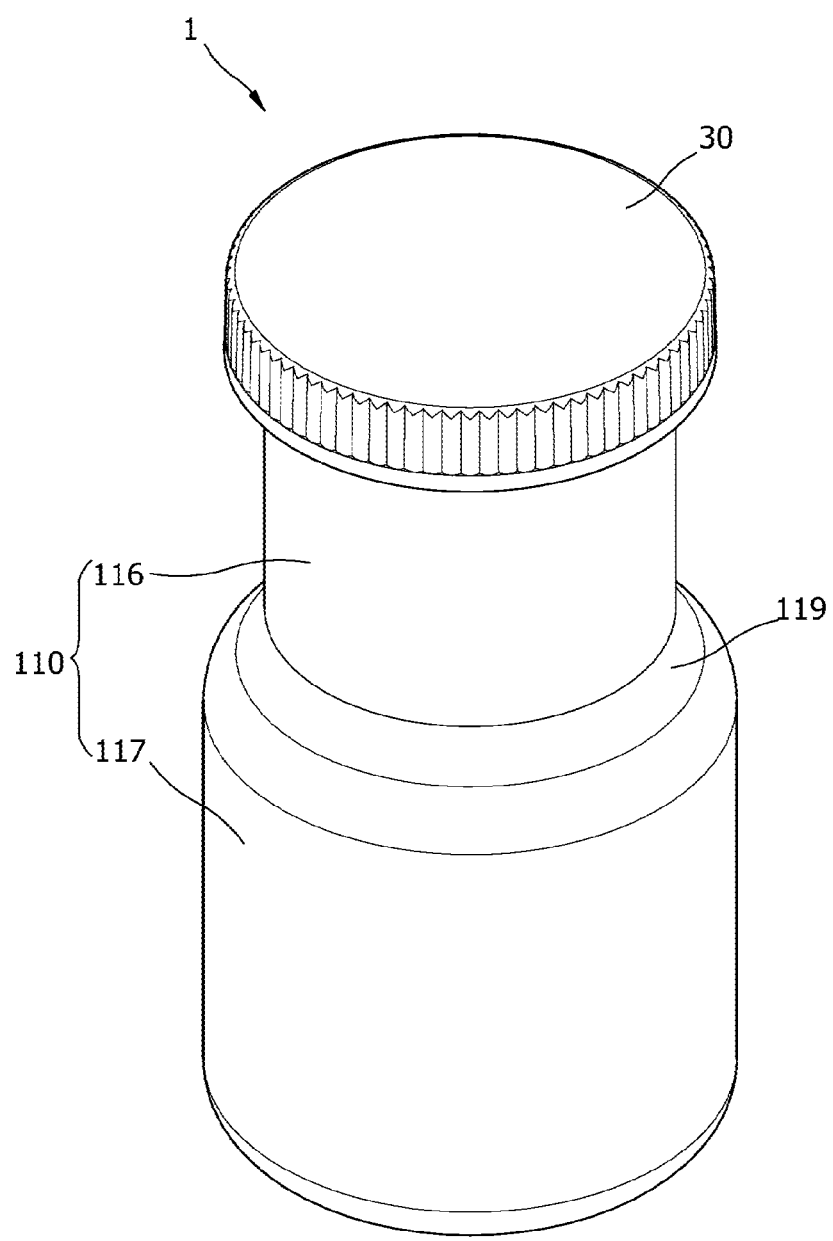
FIG. 39 is a perspective view of a contents movement device including a passage device according to a fifth embodiment of the present invention.
Figure 40:
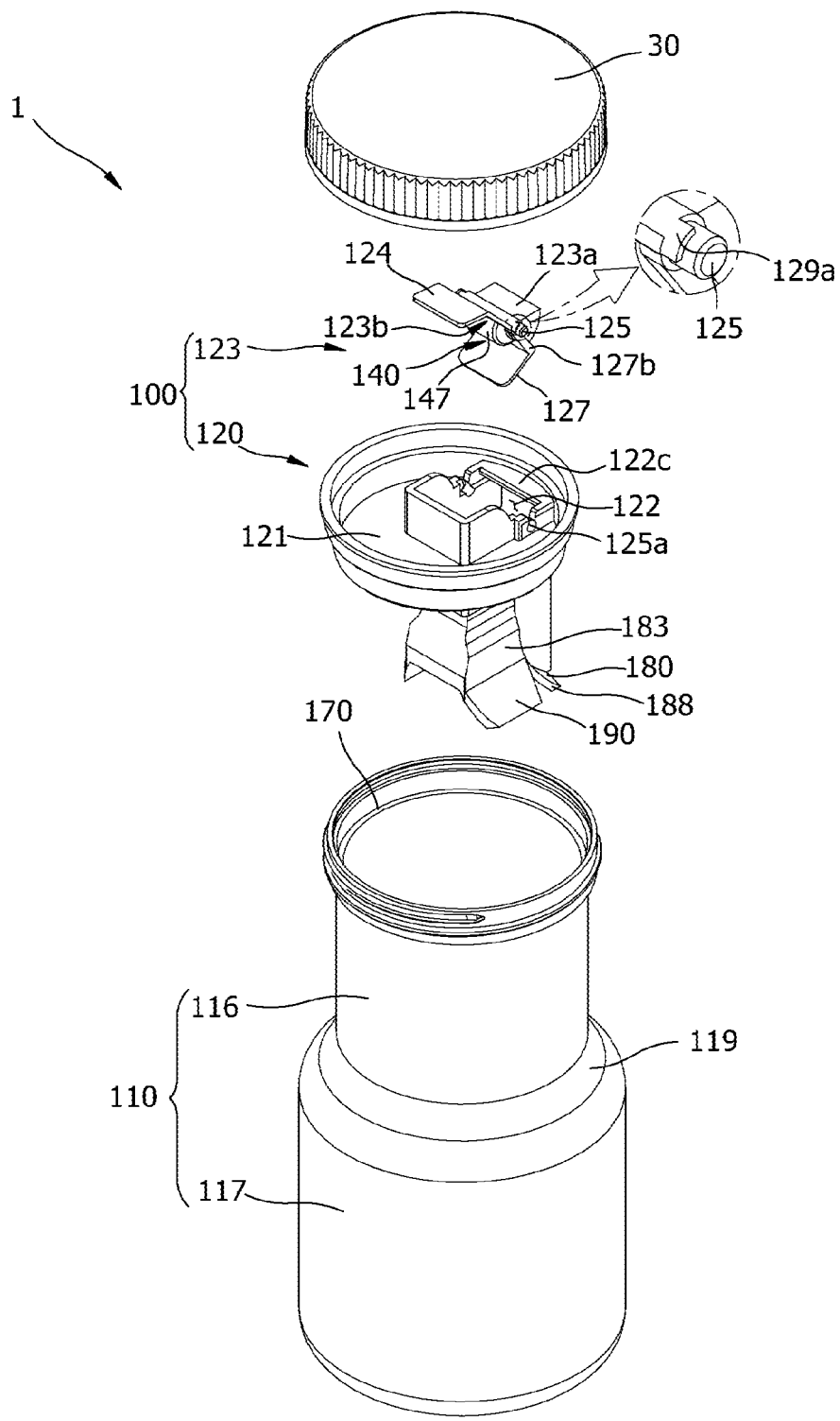
FIG. 40 is an exploded perspective view of the contents movement device including the passage device according to the fifth embodiment of the present invention.

FIG. 39 is a perspective view of a contents movement device including a passage device according to a fifth embodiment of the present invention, and FIG. 40 is an exploded perspective view of the contents movement device including the passage device according to the fifth embodiment of the present invention.

Figure 41:
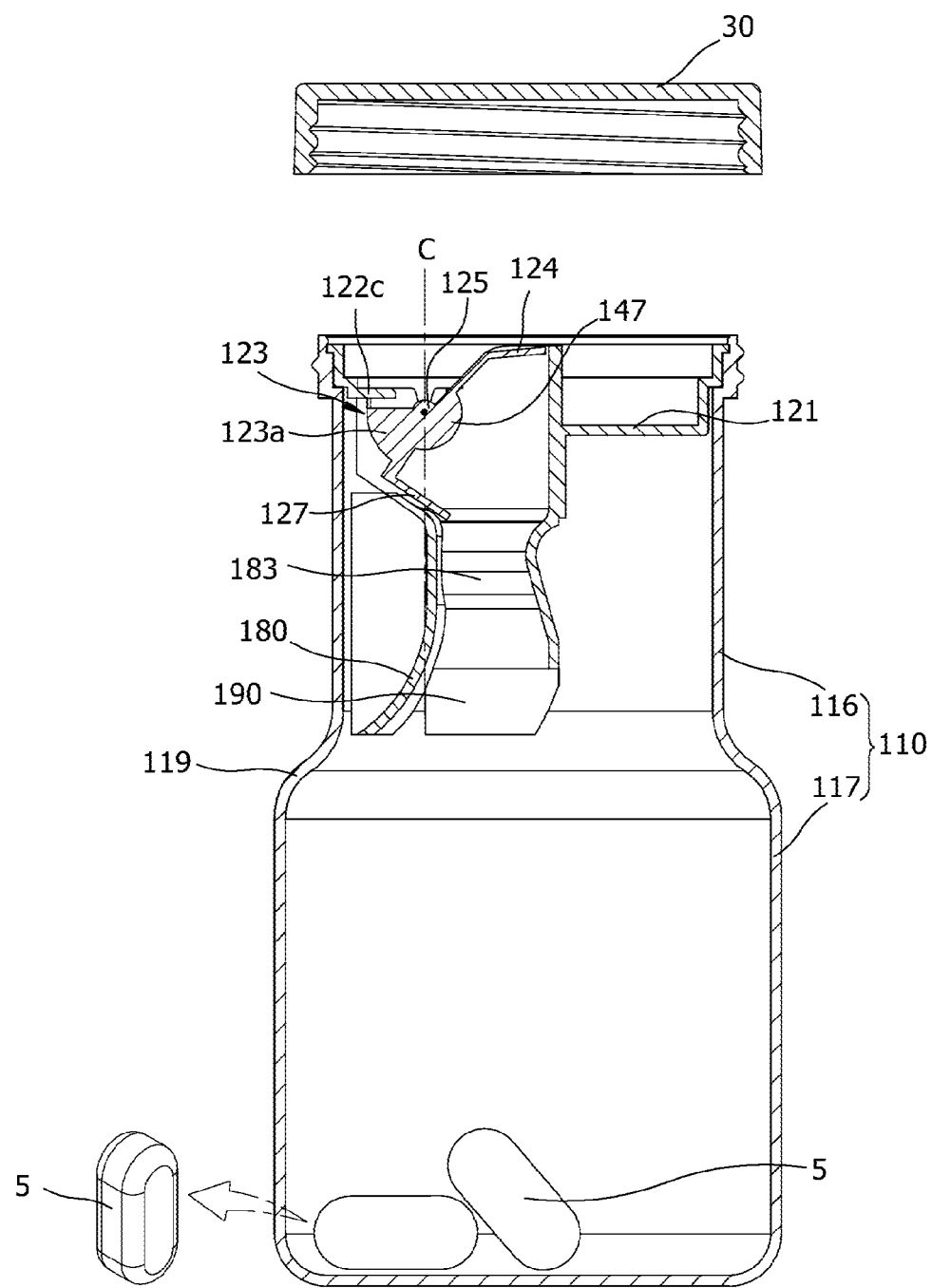
FIG. 41 is a cross-sectional view of the contents movement device including the passage device according to the fifth embodiment of the present invention.
Figure 42:
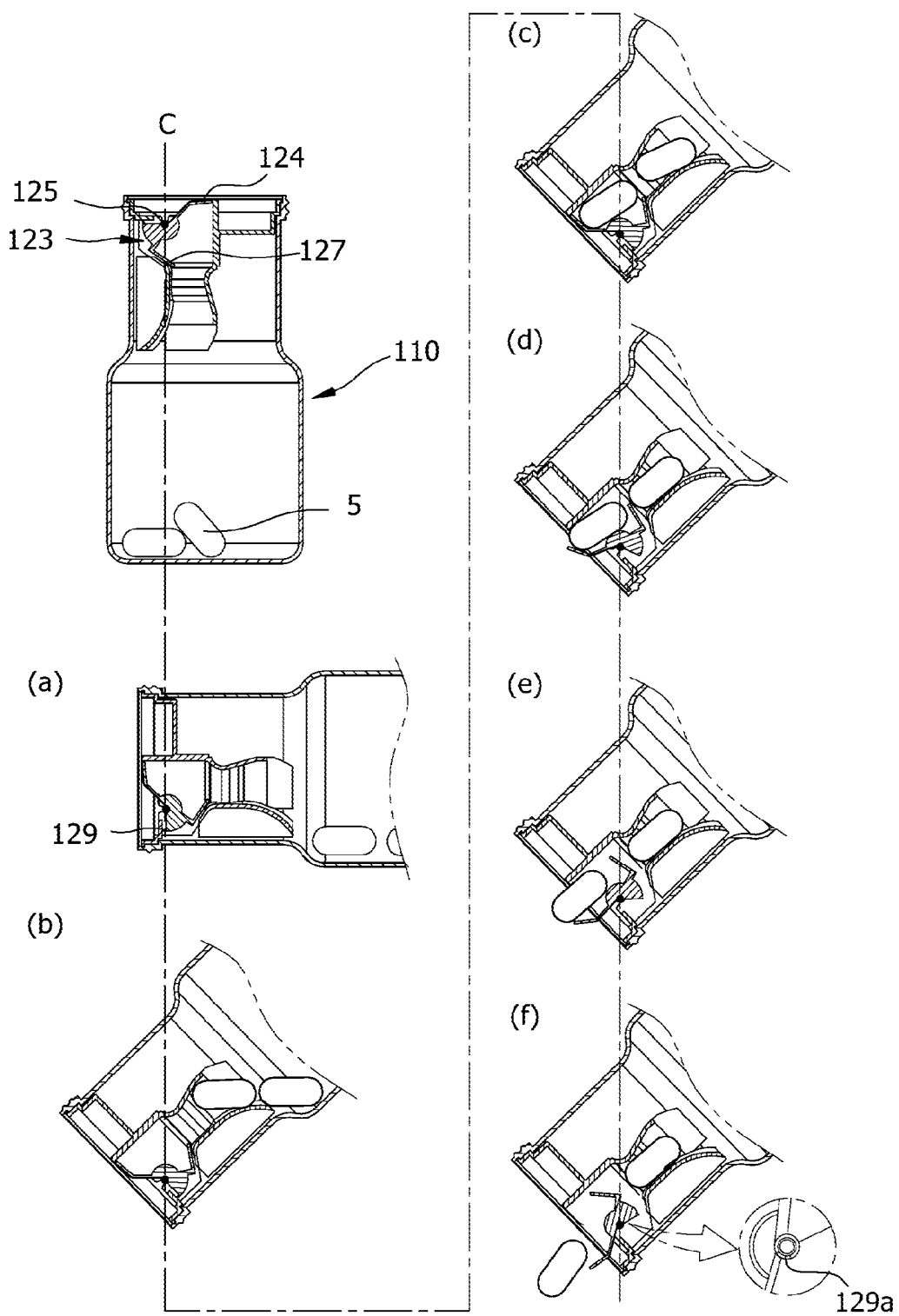
FIG. 42 is an operational diagram of the contents movement device including the passage device according to the fifth embodiment of the present invention.

FIG. 41 is a cross-sectional view of the contents movement device including the passage device according to the fifth embodiment of the present invention, and FIG. 42 is an operational diagram of the contents movement device including the passage device according to the fifth embodiment of the present invention.

As shown in FIGS. 39 to 42, the contents movement device 1 including the passage device 100 according to the fifth embodiment of the present invention includes the housing 110, the passage operation portion 120, and the supply guide portion 119.

Description of the passage operation portion 120 will be replaced by the above description.

The housing 110 includes the enlarged-diameter portion 117 and the reduced-diameter portion 116.

In addition, the passage device 100 includes the passage operation portion 120 and the contents passage means 123.

Here, the passage movement portion 123 includes the blocking member 127 and the opening member 124.

The blocking member 127 may be formed to be bent, and the blocking member bent portion 127b of the blocking member 127 may be formed to be linearly bent or to be a curved surface.

An angle of the blocking member bent portion 127b formed by bending the blocking member 127 may be a steep incline close to a right angle so as to not allow the contents, excluding a demanded quantity, to enter the passage operation portion 120. Of course, the blocking member bent portion 127b may be bent at a variety of angles.

Then, the blocking member 127 at least partially blocks the opening portion 122 included in the passage operation portion 120 such that more than the fixed quantity of the contents 5 may be prevented from moving into the opening portion 122.

Also, the passage operation portion 120 includes a safe cover 122c which blocks a part of the opening portion 122.

Particularly, as shown in FIGS. 41 and 42, the safe cover 122c performs a function of preventing a negligent accident by preventing a child from pushing the movement control member 123a exposed to the opening portion 122 with a finger such that the opening member 124 pivots upward to be held and removed by the child.

The safe cover 122c may be modified to a variety of shapes and may be manufactured to be integrated with the fixing member 121.

Also, as shown in FIGS. 40 to 42, a stopper 129a may be further provided on the movement member 125 of the passage movement portion 140 to restrict rotation of the passage movement portion 140. The stopper 129a is held by the passage operation portion 120 such that rotational angles of the opening member 124 and the blocking member 127 are restricted.

Description of unstated reference numerals will be replaced by the above description.

Figure 43:
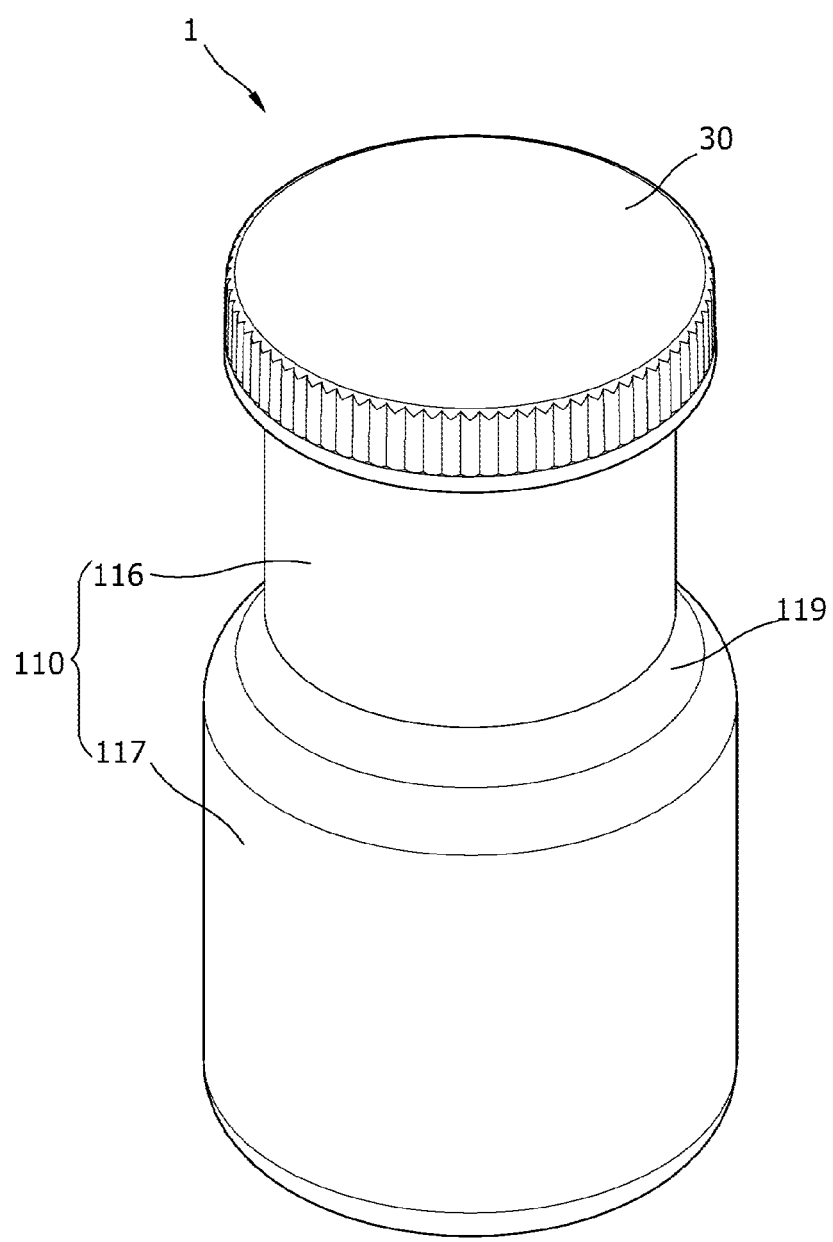
FIG. 43 is a perspective view of a contents movement device including a passage device according to a sixth embodiment of the present invention.
Figure 44:
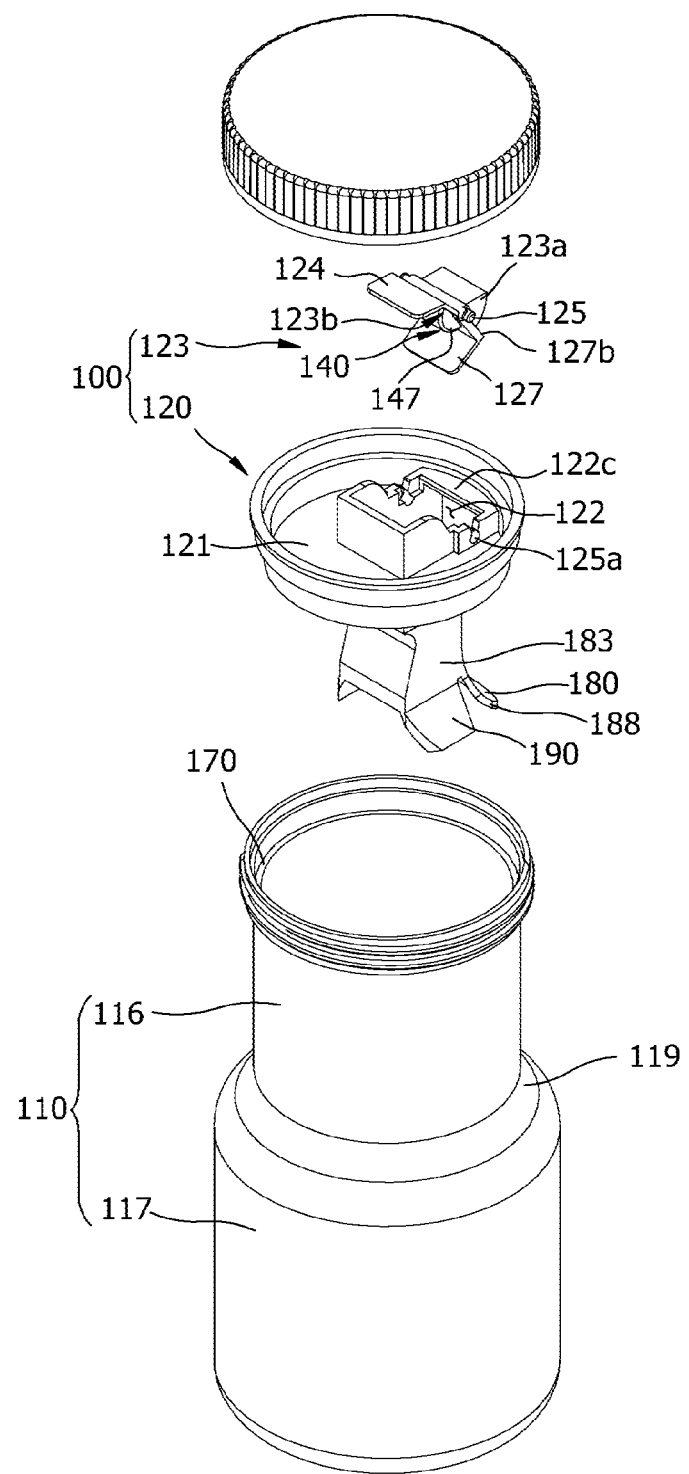
FIG. 44 is an exploded perspective view of the contents movement device including the passage device according to the sixth embodiment of the present invention.

FIG. 43 is a perspective view of a contents movement device including a passage device according to a sixth embodiment of the present invention, and FIG. 44 is an exploded perspective view of the contents movement device including the passage device according to the sixth embodiment of the present invention.

Figure 45:
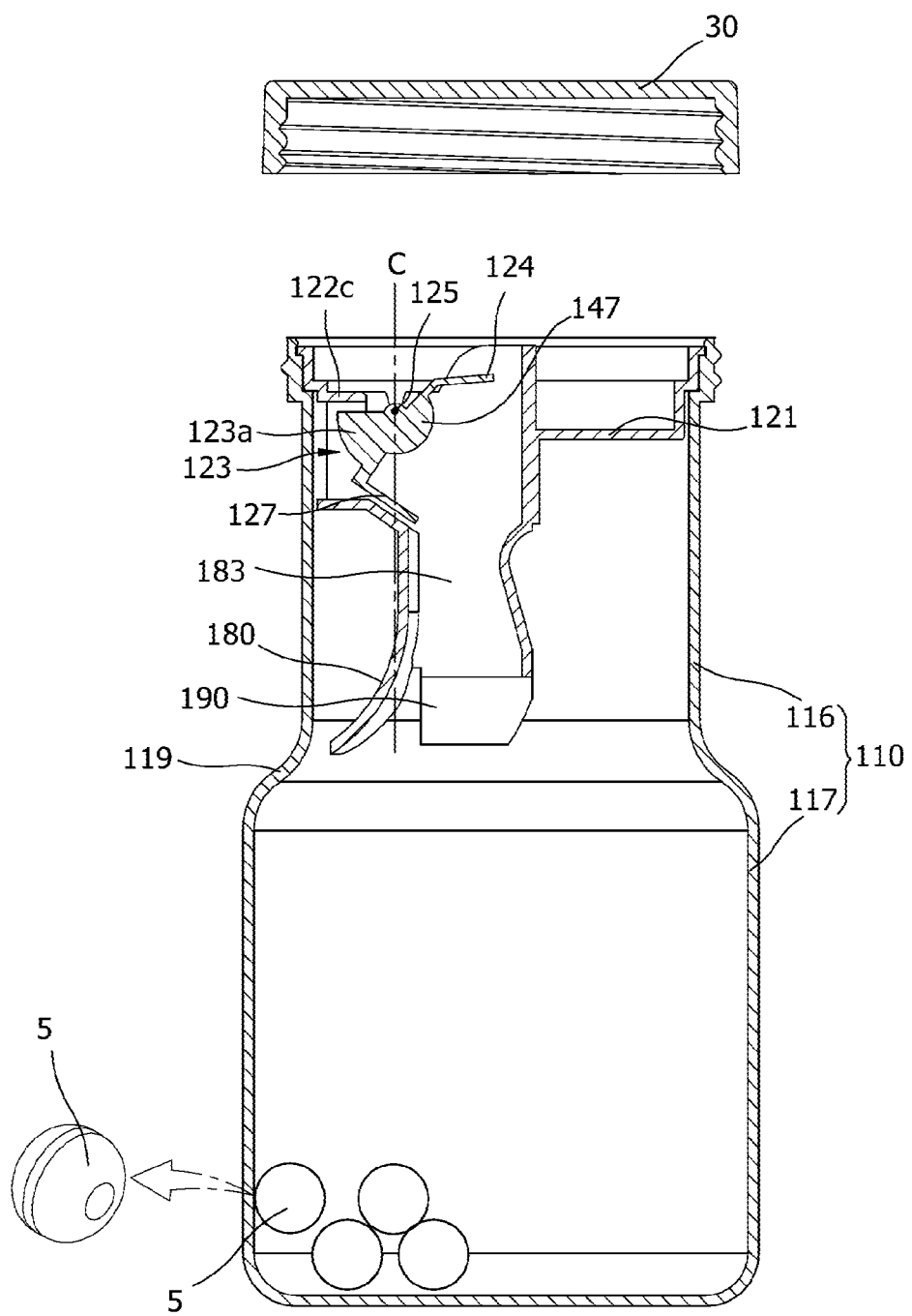
FIG. 45 is a cross-sectional view of the contents movement device including the passage device according to the sixth embodiment of the present invention.
Figure 46:
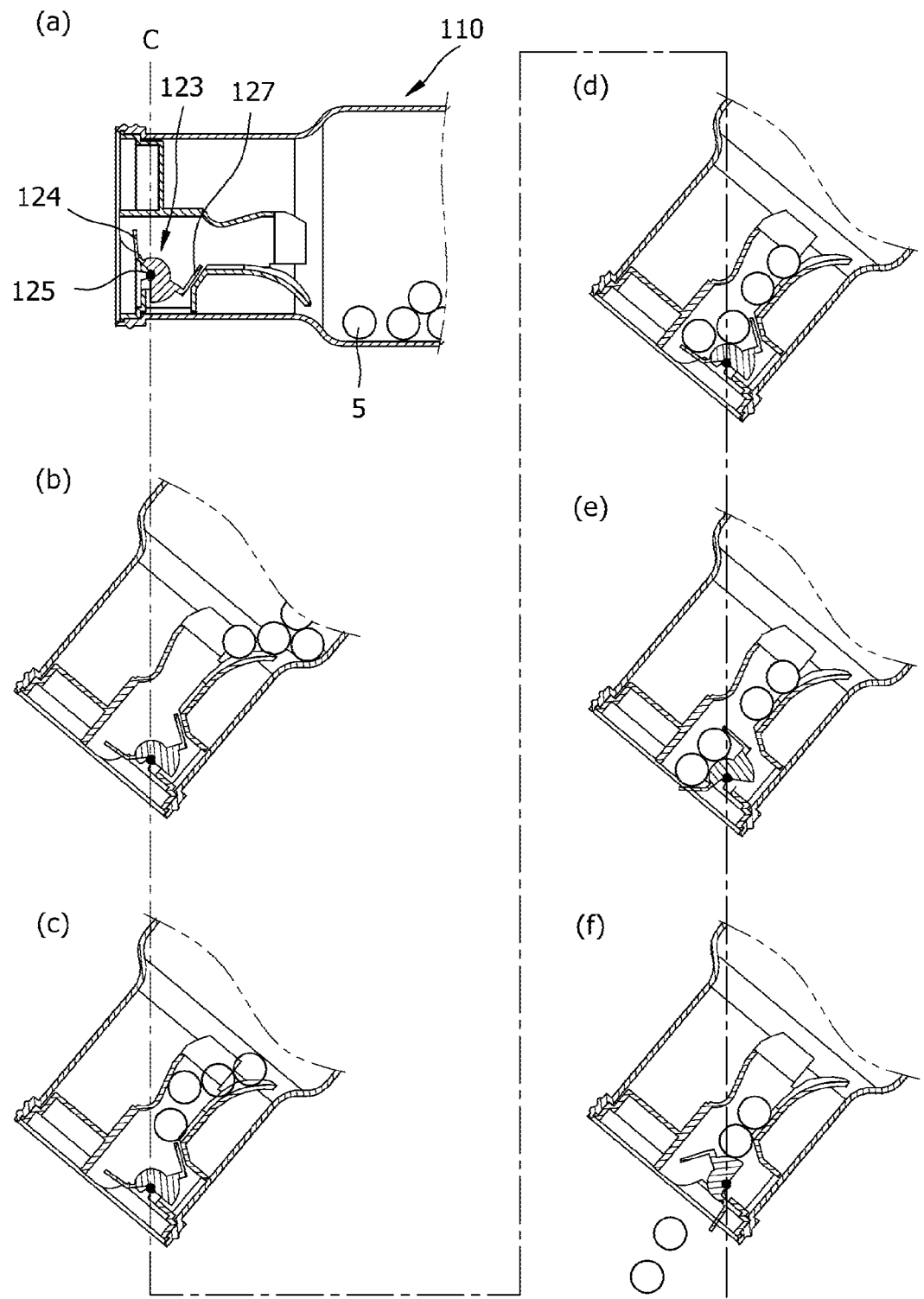
FIG. 46 is an operational diagram of the contents movement device including the passage device according to the sixth embodiment of the present invention.
Figure 47:
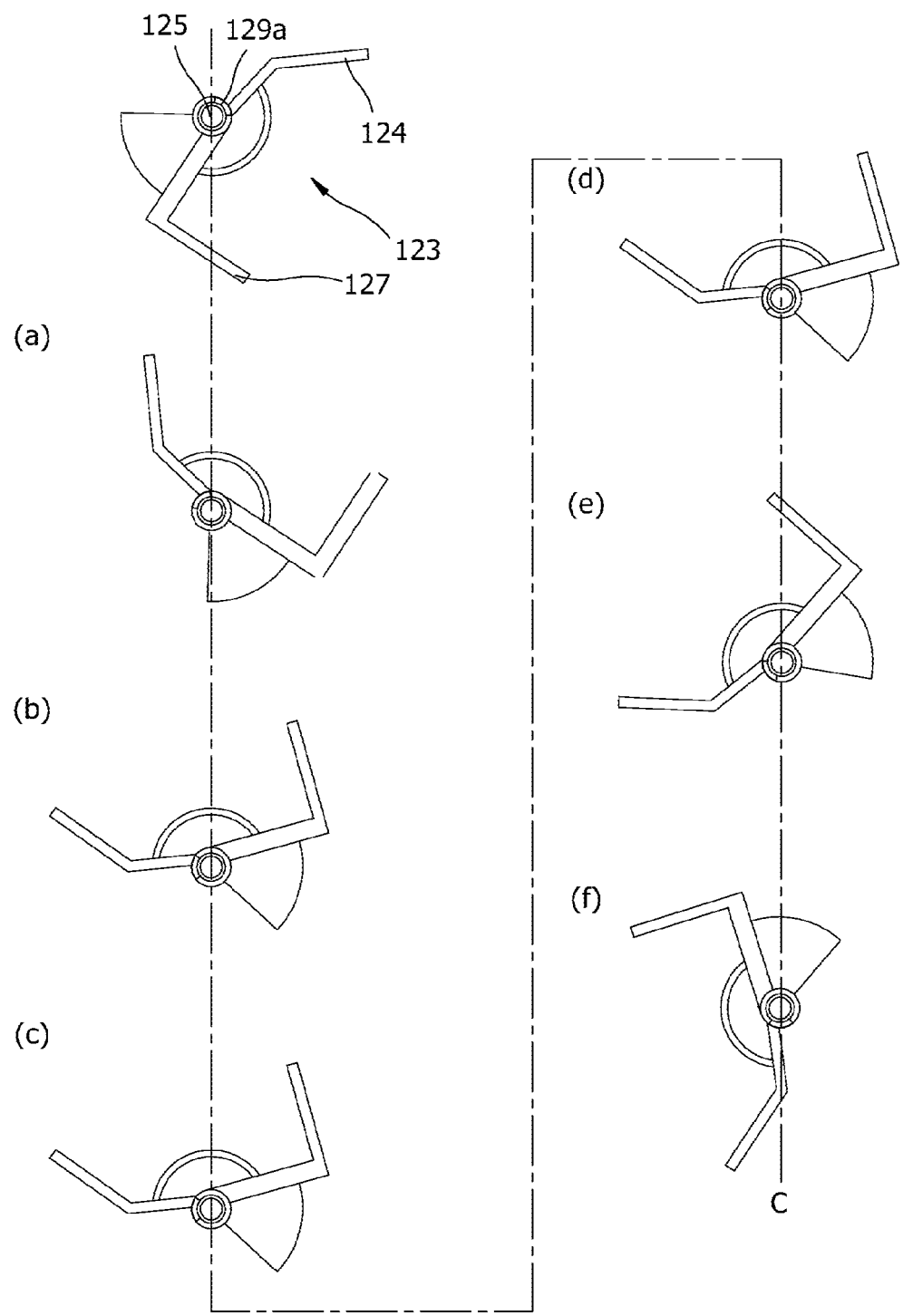
FIG. 47 is a significant part operational diagram of the contents movement device including the passage device according to the sixth embodiment of the present invention.

FIG. 45 is a cross-sectional view of the contents movement device including the passage device according to the sixth embodiment of the present invention, FIG. 46 is an operational diagram of the contents movement device including the passage device according to the sixth embodiment of the present invention, and FIG. 47 is a significant part operational diagram of the contents movement device including the passage device according to the sixth embodiment of the present invention.

As shown in FIGS. 43 to 47, the contents movement device 1 including the passage device 100 according to the sixth embodiment of the present invention includes the housing 110, the passage operation portion 120, and the supply guide portion 119.

Description of the passage operation portion 120 will be replaced by the above description.

The passage operation portion 120 performs a function of inducing movement of a fixed quantity or a demanded quantity of the contents 5. Here, "the fixed quantity" means the same number or quantity and a quantity or number of different movements within a permissible range. "The demanded quantity" is a quantity (number) needed by a user and is included within the range of "the fixed quantity."

In the embodiment, a fixed quantity includes two circular tablets and the two tablets or an allowable quantity close to the number of two tablets may pass through the passage operation portion 120.

In addition, a configuration in which a fixed quantity of the contents 5 having a circular tablet shape passes through the passage operation portion 120 is equal to that of the fifth embodiment and will be replaced thereby.

Also, description of unstated reference numerals will be replaced by the above description.

Figure 48:
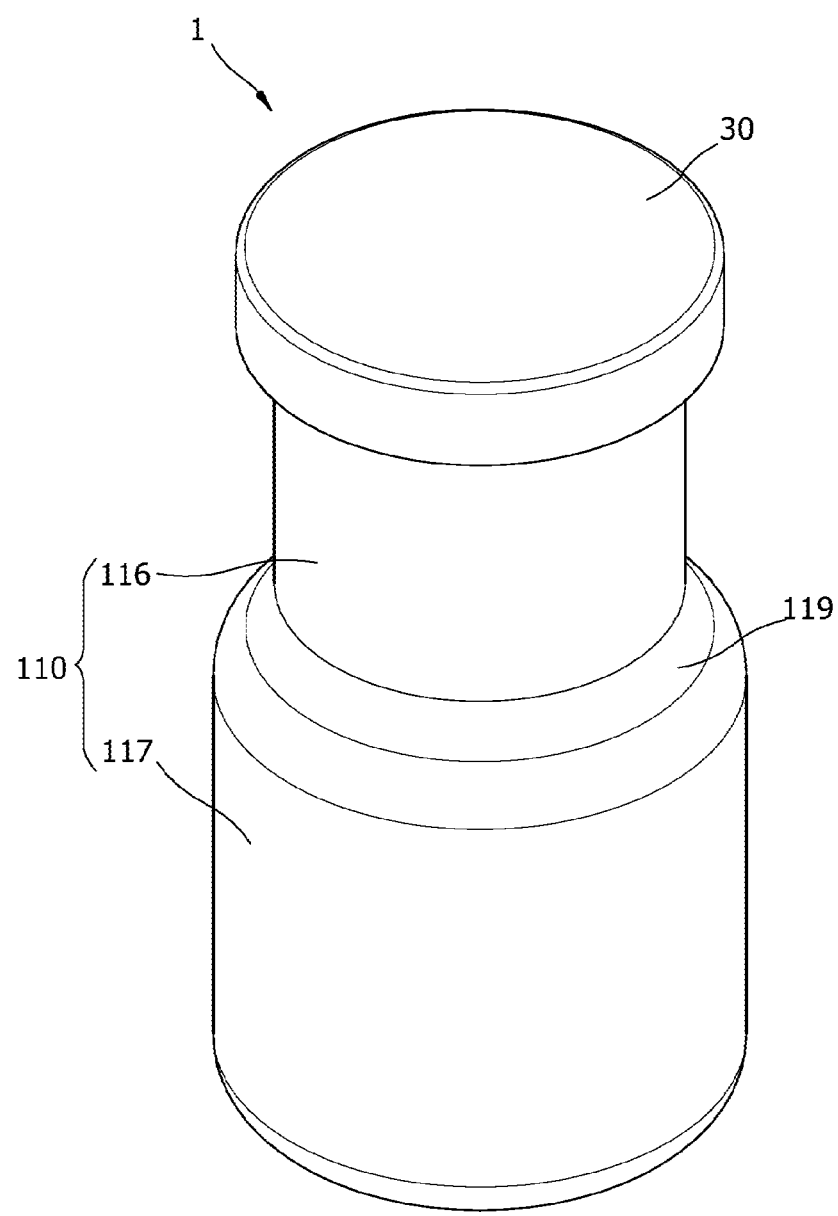
FIG. 48 is a perspective view of a contents movement device including a passage device according to a seventh embodiment of the present invention.
Figure 49:
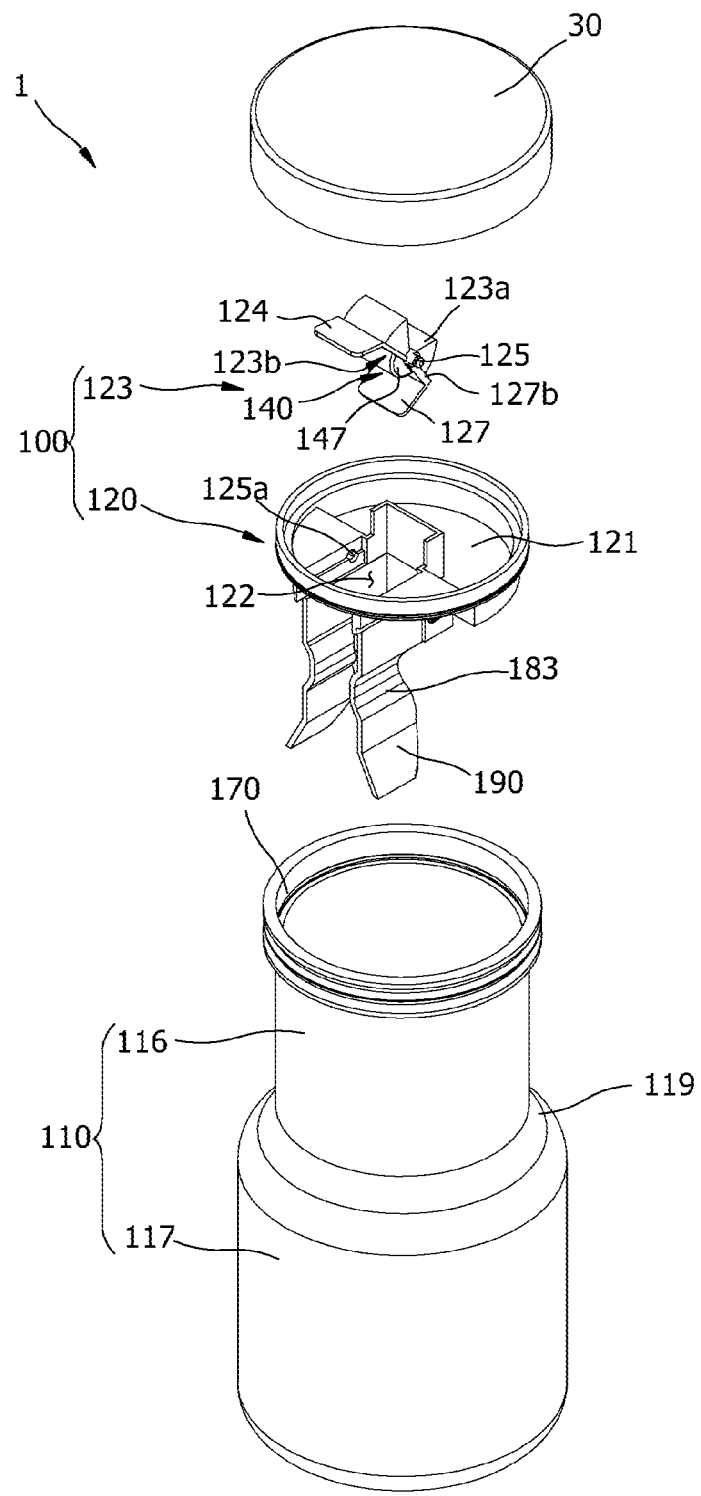
FIG. 49 is an exploded perspective view of the contents movement device including the passage device according to the seventh embodiment of the present invention.
Figure 50:
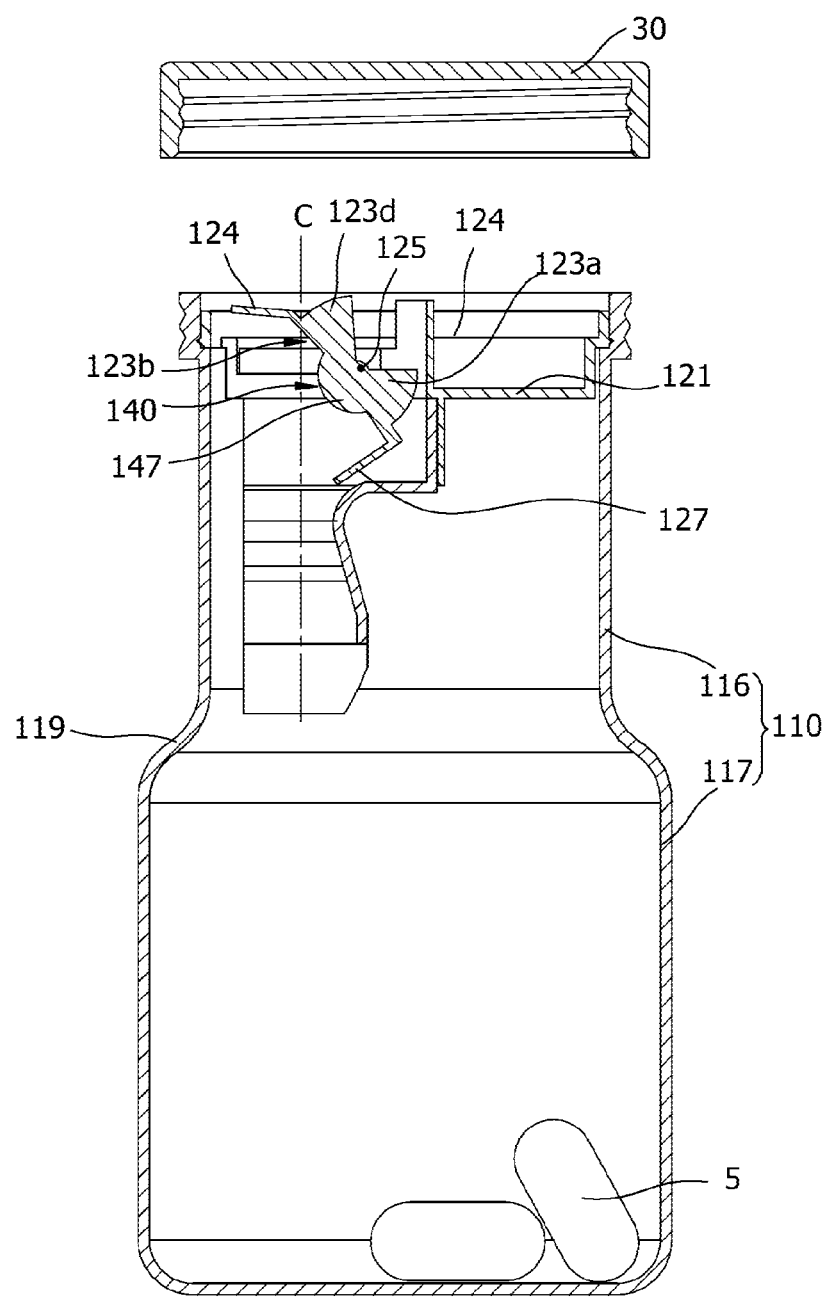
FIG. 50 is a cross-sectional view of the contents movement device including the passage device according to the seventh embodiment of the present invention.

FIG. 48 is a perspective view of a contents movement device including a passage device according to a seventh embodiment of the present invention, FIG. 49 is an exploded perspective view of the contents movement device including the passage device according to the seventh embodiment of the present invention, and FIG. 50 is a cross-sectional view of the contents movement device including the passage device according to the seventh embodiment of the present invention.

Figure 51:
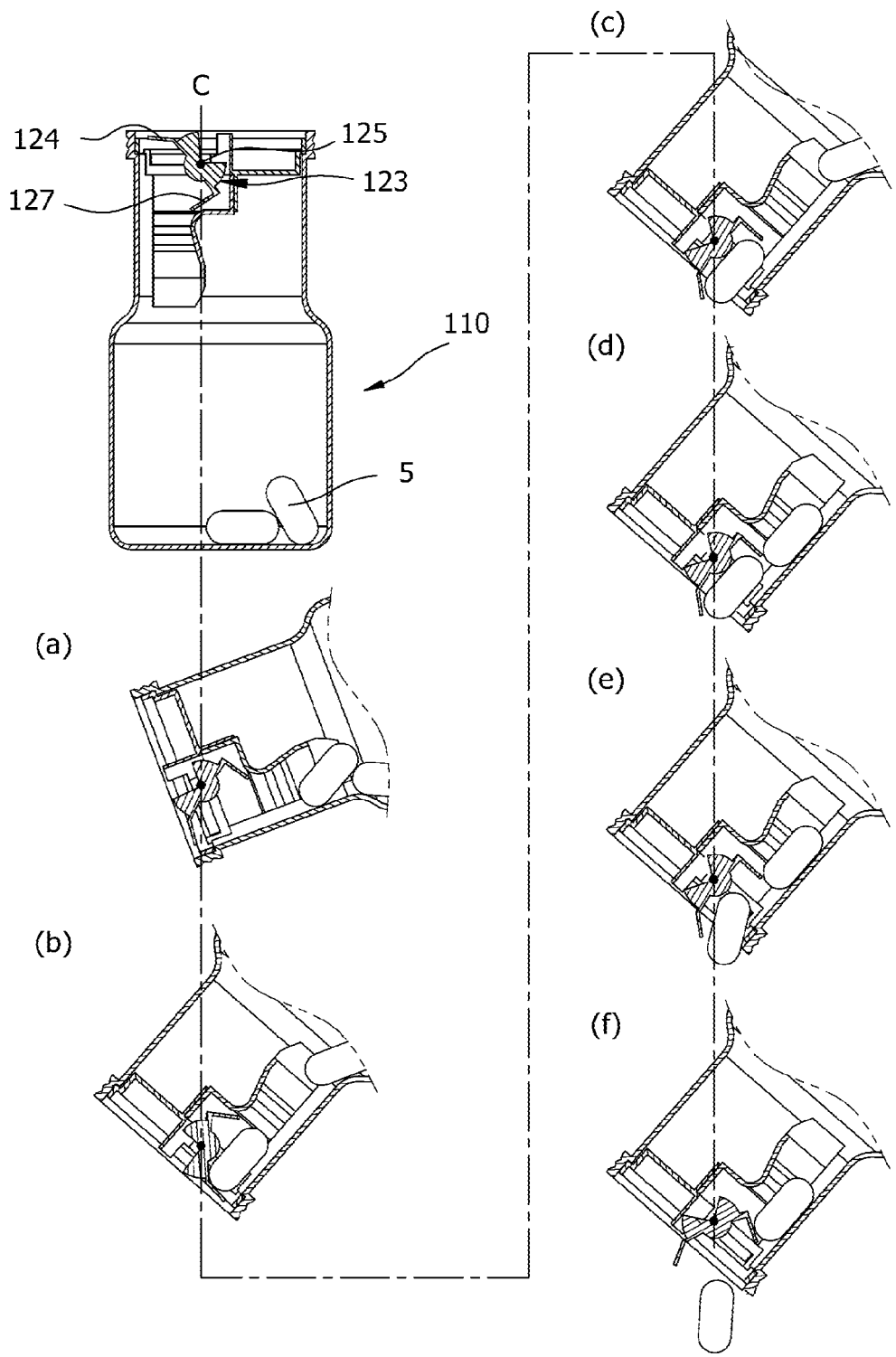
FIG. 51 is an operational diagram of the contents movement device including the passage device according to the seventh embodiment of the present invention.
Figure 52:
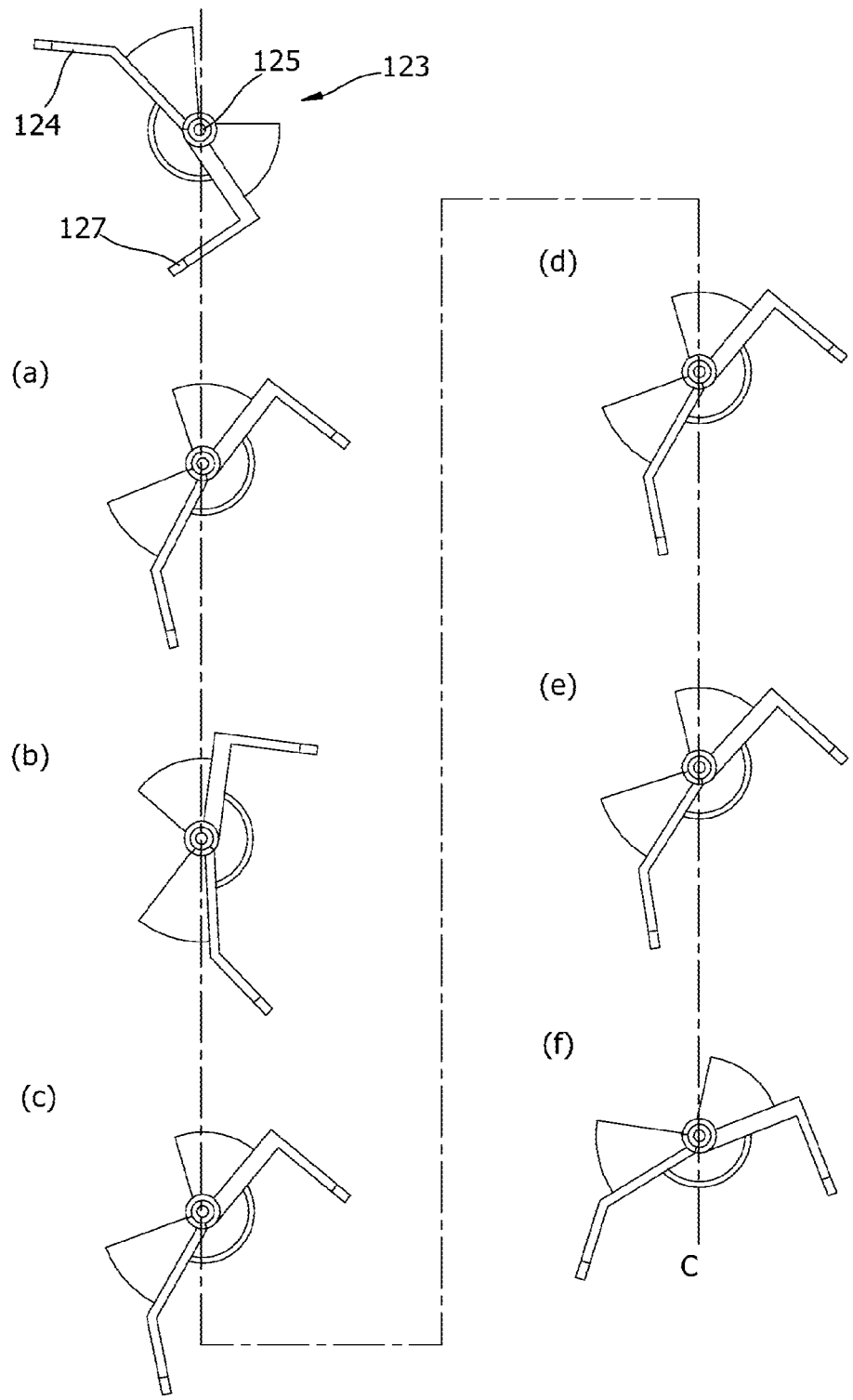
FIG. 52 is a significant part operational diagram of the contents movement device including the passage device according to the seventh embodiment of the present invention.

FIG. 51 is an operational diagram of the contents movement device including the passage device according to the seventh embodiment of the present invention, and FIG. 52 is a significant part operational diagram of the contents movement device including the passage device according to the seventh embodiment of the present invention.

As shown in FIGS. 48 to 52, the contents movement device 1 including the passage device 100 according to the seventh embodiment of the present invention includes the housing 110, the passage operation portion 120, and the supply guide portion 119.

Description of the passage operation portion 120 will be replaced by the above description.

The passage device 100 includes the passage operation portion 120 and the contents passage means 123.

Particularly, the contents passage means 123 includes the passage movement portion 140.

The passage movement portion 140 performs a function of being opened by movement to allow the contents 5 to pass therethrough. That is, the passage movement portion 140 interconnects to an opening member 124 and closes the opened opening portion 122.

Here, the passage movement portion 140 includes the blocking member 127 and the opening member 124.

Particularly, the movement control member 123a included in the passage movement portion 140 protrudes from a surface of the blocking member 127 opposite to the passage movement portion 140 or the balancing portion 123b, and a movement control member 123d protrudes from a surface of the opening member 124 opposite to the passage movement portion 140 or the balancing portion 123b.

That is, the passage movement portion 140 includes the movement control member 123d which protrudes from the other surface opposite to one surface which forms the bottom height changing member 147 to be adjacent to the opening member 124 and the movement control member 123a which protrudes to be adjacent to the blocking member 127.

Particularly, in the embodiment, the passage movement portion 140 is disposed above the contents 5 which pass through the opening portion 122 along the inner surface of the housing 110 or the reduced-diameter portion 116 such that the contents 5 which pass through the contents passage means 123 may come into less contact with the passage movement portion 140 except for the opening member 124 and the blocking member 127.

As shown in FIGS. 51, 52(a), and 52(b), since the movement control members 123a and 123d are formed as a single body or divided to be partitioned, while the housing 110 tilts, the opening member 124 and the blocking member 127 generate a gravitational center balancing force on the basis of a vertical axis C which passes the rotational axis 125 of the passage movement member 124 such that the passage movement portion 140 may maintain a passage standby state until a force is generated of the initially passing contents 5 coming into contact with or pushing the passage movement portion 140 except for the blocking member 127 or the opening member 124.

Particularly, FIGS. 51 and 52(a) illustrate a state in which the housing 110 tilts over horizontality (−90 degrees or more). Here, the initial state in which the blocking member 127 is opened and the passage movement portion 140 does not move (pivot) is maintained. The contents 5 start moving while sliding along the incline of the inside of the housing 110 with a force in the gravitational direction C.

Even when a step is present between the housing 110 and the guide member 190, a piece of the contents 5 having a tablet shape does not stand and lies to enter the guide member 190. Here, it becomes a state in which a first tablet of the contents 5 does not enter the passage compartment portion 124a provided between the opening member 124 and the blocking member 127 of the passage movement portion 140.

The contents 5 which have a tablet shape and not a flat shape do not stand and stably slide along the incline of the guide member 190.

Although the passage movement portion 140 tilts counterclockwise more than 90 degrees on the basis of the initial state due to the tilt of the housing 110, the contents 5 do not come into contact with the passage movement portion 140 and attempt to rotate counterclockwise, which is a leftward direction, due to weight-leaning on a left side based on the movement member 125 but are suppressed by the stopper 129 to remain in a standby state.

FIGS. 51 and 52(b) illustrate a state in which the blocking member 127 is opened and the contents 5 enter an internal space of the passage movement portion 140.

The weight of the contents 5 is added to the balancing portion 123b of the passage movement portion 124 such that weight-leaning on a left part of the gravitational vertical line C which is a side of the opening member 124 increases relatively. Accordingly, due to the balancing portion 123b and resistance of the contents 5, the passage movement portion 140 may rotate clockwise more than the housing 110 tilt while the contents 5 come into contact with the opening member 124 or approach to come into contact with the opening member 124.

Here, due to friction between the balancing portion 123b and the contents 5 which move along the incline in the gravitational direction or by a force of pushing from the opening member 124, the passage movement portion 140 moves with the contents 5 in the space of the passage compartment portion 124a.

FIGS. 51 and 52(c) illustrate a state in which the passage movement portion 140 rotates further clockwise on the basis of the movement member 125 from the initial state such that the blocking member 127 starts blocking contents 6 which enter after the fixed quantity of the contents (tablets) 5.

Here, with the weight of the contents 5 having a tablet shape, a weight of the left side of the gravitational vertical line C becomes greater than a weight of the right side such that weight leaning on the left side may occur and the passage movement portion 140 may rotate clockwise, that is, to the right side of the rotational center of the movement member 125 to pass the contents 5 outward.

As shown in FIGS. 51 and 52(d) to 52(f), when the passage movement portion 140 rotates further clockwise on the basis of the movement member 125 from the initial state, the fixed quantity of the contents 5 pushing the passage movement portion 140 moves outward and does not come into contact with the opening member 124 side of the passage movement portion 140 any further such that the passage movement portion 140 has a greater weight on the right side based on the central line C and a force of rotating clockwise, that is, rightward, occurs. However, as the residual contents 6 come into contact with the blocking member 127 due to gravity, the valve 100 can not return to the right side and remains in a current state such that the contents 5 do not enter the space of the passage compartment portion 124a any further.

As a result, until the housing 110 tilts more than 90 degrees, as shown in FIGS. 51 and 52, the contents 5 do not come into contact with the passage movement portion 140 of the contents passage means 123. Here, the opening member 124 of the passage movement portion 140 maintains a state in which the opening member 122 is blocked by the weight balancing force of the passage movement portion 140.

Also, until the housing 110 tilts within a set angle, particularly, until the contents 5 push the opening member 124, the opening member 124 remains in the state of blocking the opening member 122.

Then, although the housing 110 tilts more than the set angle or tilts within the set angle, when the contents push the opening member 124, the passage movement portion 140 of the contents passage means 123 rotates clockwise on the basis of the movement member 125.

That is, a tilting direction of the housing 110 becomes same to a direction in which the passage movement portion 140 rotates on the rotational shaft 125 of the passage movement portion 140.

In addition, although the housing 110 tilts, when a force of the contents 5 pushing the opening member 124 does not occur, the opening member 124 may block the opening portion 122 due to the housing which tilts from an initial position.

Of course, when the housing 110 tilts more than the set angle, the contents 5 pass through the opening portion 122 and push the opening member 124. Accordingly, the opening member 124 forcibly rotates on the basis of the movement member 125 to open the opening member 122.

Sequentially, as the blocking member 127 blocks the opening portion 122, the opening portion 122 may be sequentially opened and closed by the opening member 124 and the blocking member 127 and the fixed quantity of the contents 5 may be withdrawn.

Particularly, when the housing 110 stands in a direction opposite to the tilting direction thereof, the opening member 124 blocks the opening portion 122 due to weight balance.

That is, the passage movement portion 140 is provided in the opening portion 122 to be movable like a seesaw such that the passage operation portion 120 remains in an initial state and the opening member 124 does not open the opening portion 122 when the passage operation portion 120 tilts within the set angle.

The opening portion 122 is opened by the force of the contents pushing on the passage movement portion 140 or the weight of the passage movement portion 140 and the force of the contents pushing on the passage movement portion such that a set quantity of the contents is guided to pass through. The set angle may be set to be a tilting angle not more than 180 degrees from the initial state in which the contents movement device or accommodation device 1 with the opening portion 122 stands.

The passage movement portion 140 may perform the seesaw movement due to a weight-leaning phenomenon on a left side or a right side on the basis of the movement member 125, which is a rotational center. In a standby state in which the contents movement device or accommodation device 1 which includes the opening portion 122 tilts, a weight leans toward the opening member 124 on the basis of the movement member 125, which is the rotational center, and the blocking member 127 is held by the stopper such that the passage movement portion 140 may maintain a state in which the blocking member 127 does not block and opens the opening portion 122.

When the contents movement device or accommodation device 1 including the opening portion 122 tilts within a set angle, due to weight-leaning toward an same side of a tilting direction, the passage movement portion 140 may maintain a state in which the opening member 124 blocks the opening portion 122.

When the contents movement device or accommodation device 1 which includes the opening portion 122 tilts, the weight of the contents which move toward the opening portion 122 is added such that the passage movement portion 140 may pivot on the basis of the movement member 125, which is the rotational center, and open the opening portion 122. As described above, the passage movement portion 140 may reciprocally pivot at the opening portion 122 on the basis of the movement member 125 by using the principle of levers so as to open or close the opening portion 122.

When the passage operation portion 120 pivots within a set angle, the passage movement portion 140 may maintain a state of closing the opening portion 122 by the weight thereof and may sequentially open or close the opening portion 122 due to the force of the contents pushing on the passage movement portion 140 and due to the weight of the passage movement portion 140 so as to guide a passage of the set quantity of contents.

The passage movement portion 140 may include the balancing portion 123b configured to suppress the passage movement portion 140 from tilting more than a tilt of the passage operation portion 120 due to the weight of the passage movement portion 140 when the passage operation portion 120 tilts.

The passage movement portion 140 may include the opening member 124 which moves in a direction in which the contents pass and forms a passage space for the contents. The passage movement portion 140 may include the blocking member 127 which blocks at least a part of the opening portion 122, in conjunction with the opening member 124, to block or partially pass the contents therethrough.

The passage operation portion 120 may have a shape which prevents pivoting caused by the weight of the passage movement portion 140 due to weight balance before the set quantity of contents comes into contact with the opening member 124. The passage movement portion 140 may further include the movement control member 123a for setting a balance in the center of gravity of a lever movement.

Description of unstated reference numerals will be replaced by the above description.

Figure 53:
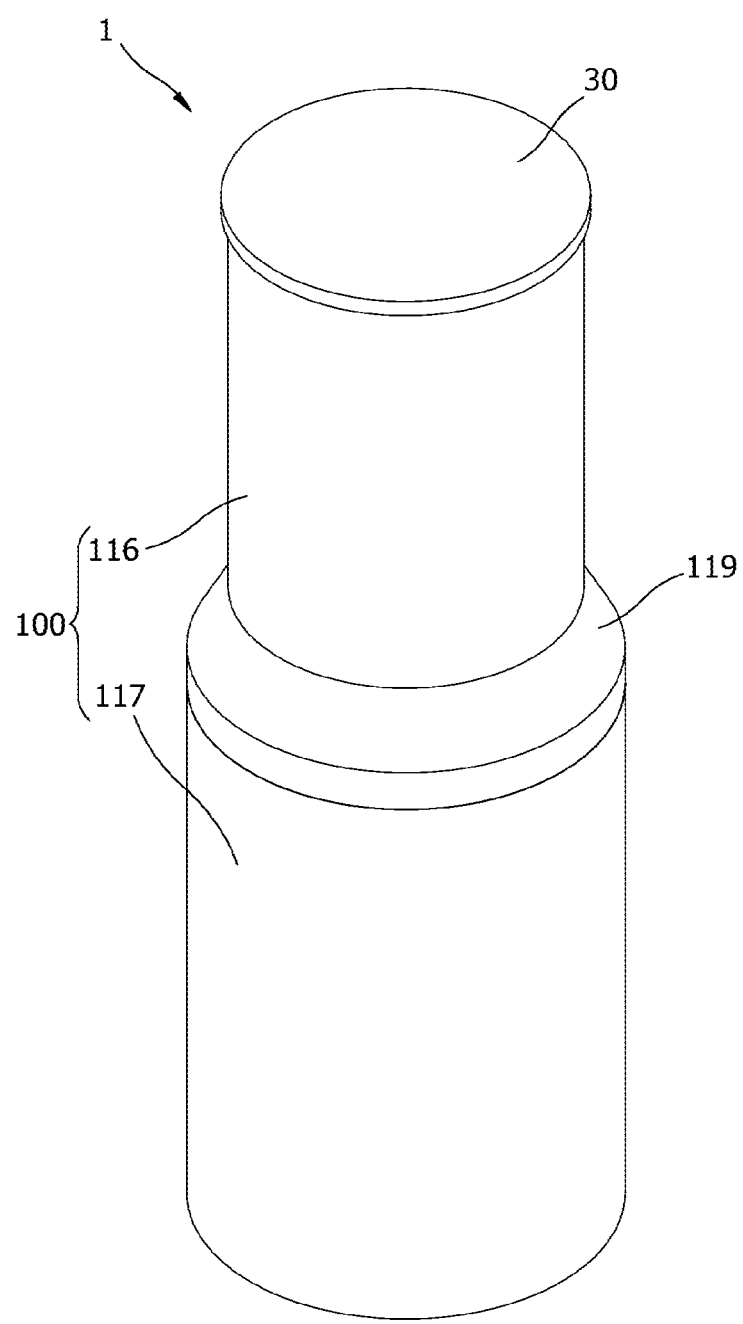
FIG. 53 is a perspective view of a contents movement device including a passage device according to an eighth embodiment of the present invention.
Figure 54:
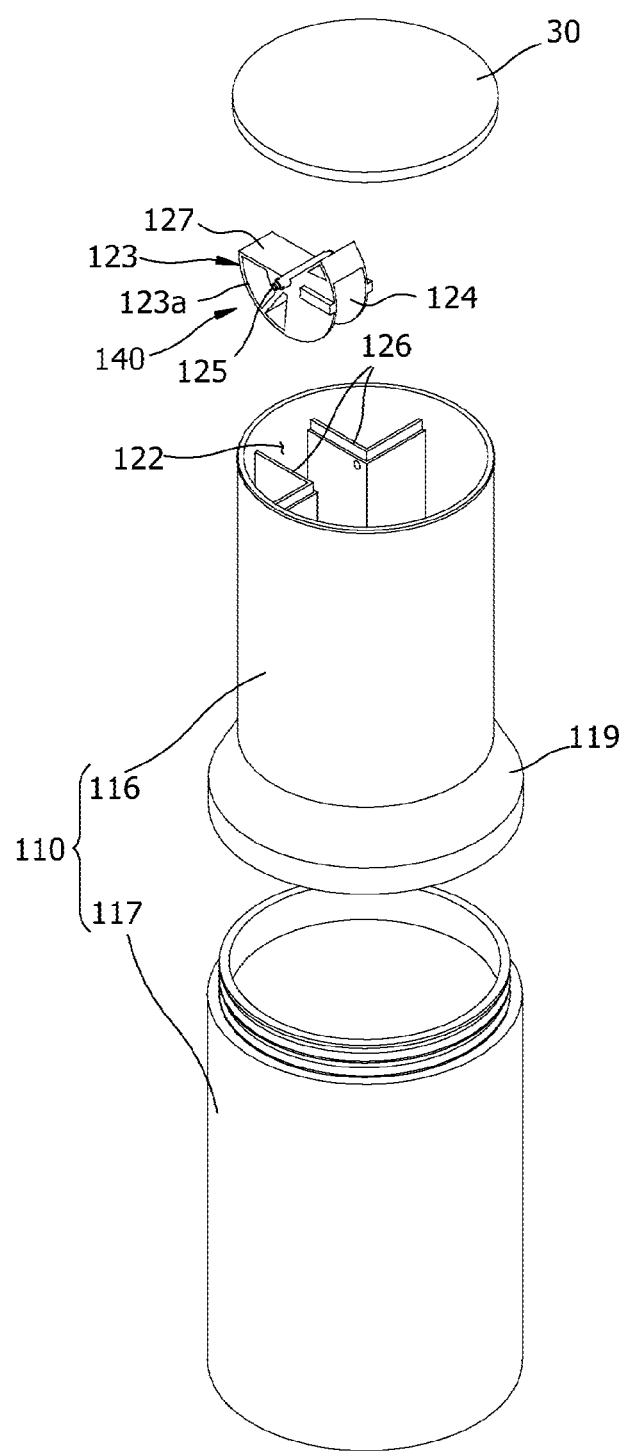
FIG. 54 is an exploded perspective view of the contents movement device including the passage device according to the eighth embodiment of the present invention.
Figure 55:
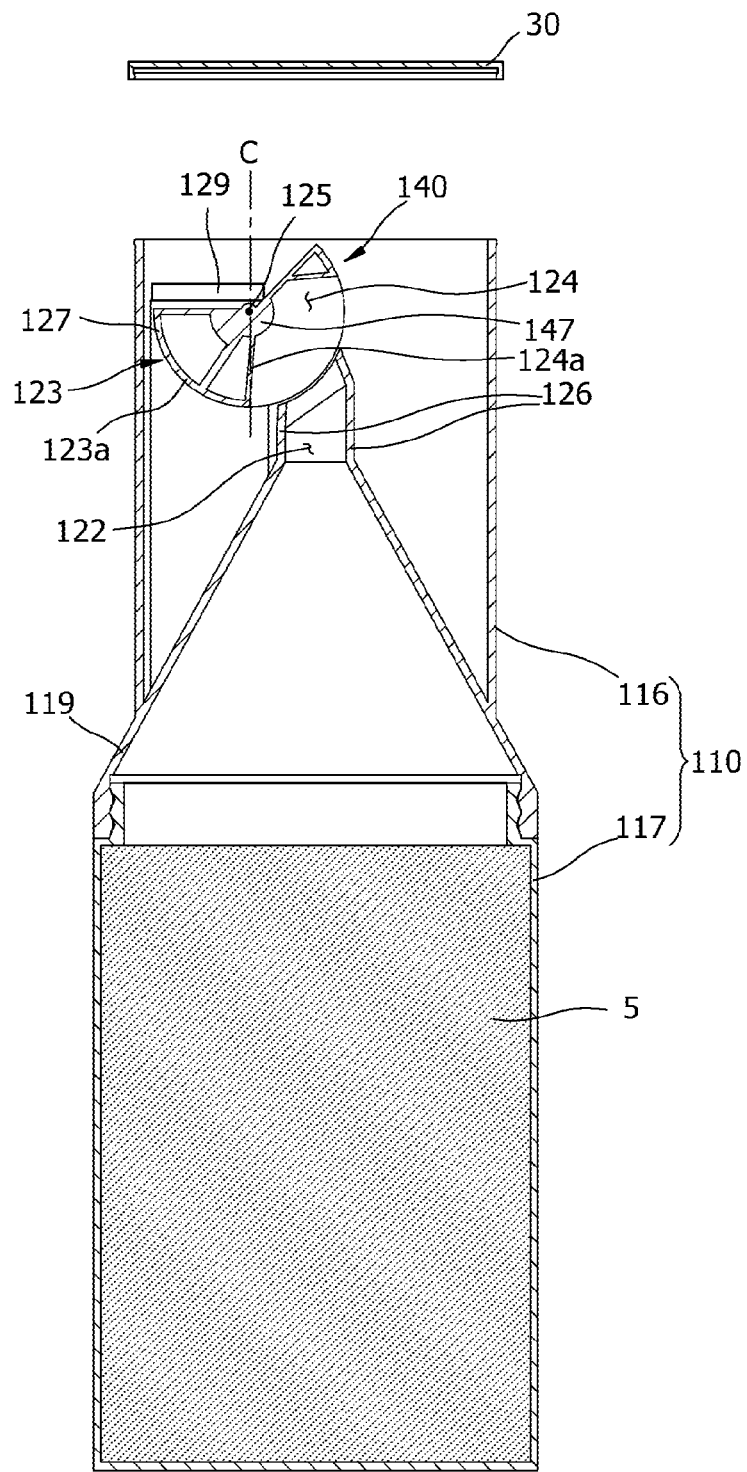
FIG. 55 is a cross-sectional view of the contents movement device including the passage device according to the eighth embodiment of the present invention.

FIG. 53 is a perspective view of a contents movement device including a passage device according to an eighth embodiment of the present invention, FIG. 54 is an exploded perspective view of the contents movement device including the passage device according to the eighth embodiment of the present invention, and FIG. 55 is a cross-sectional view of the contents movement device including the passage device according to the eighth embodiment of the present invention.

Figure 56:
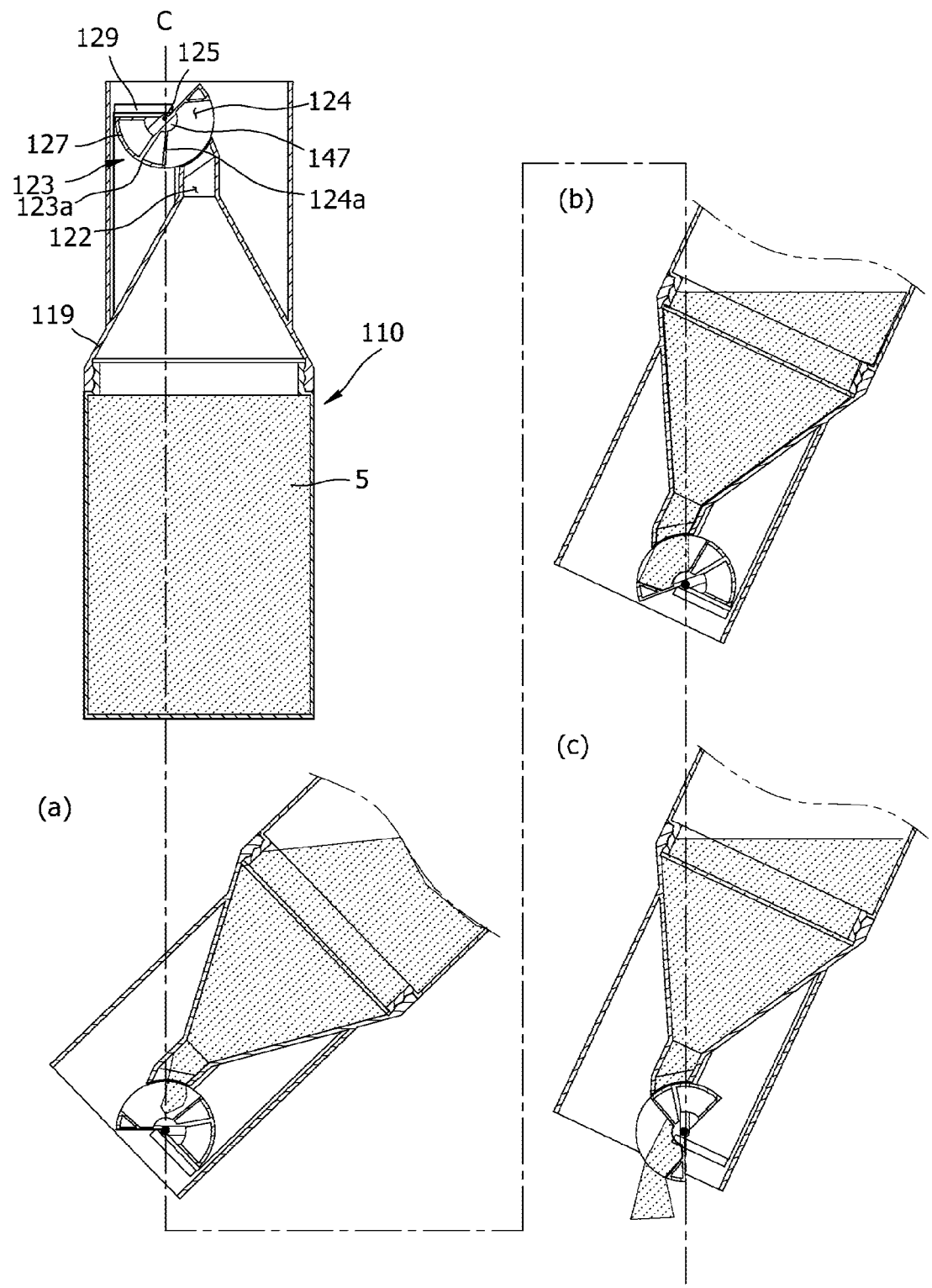
FIG. 56 is an operational diagram of the contents movement device including the passage device according to the eighth embodiment of the present invention.
Figure 57:
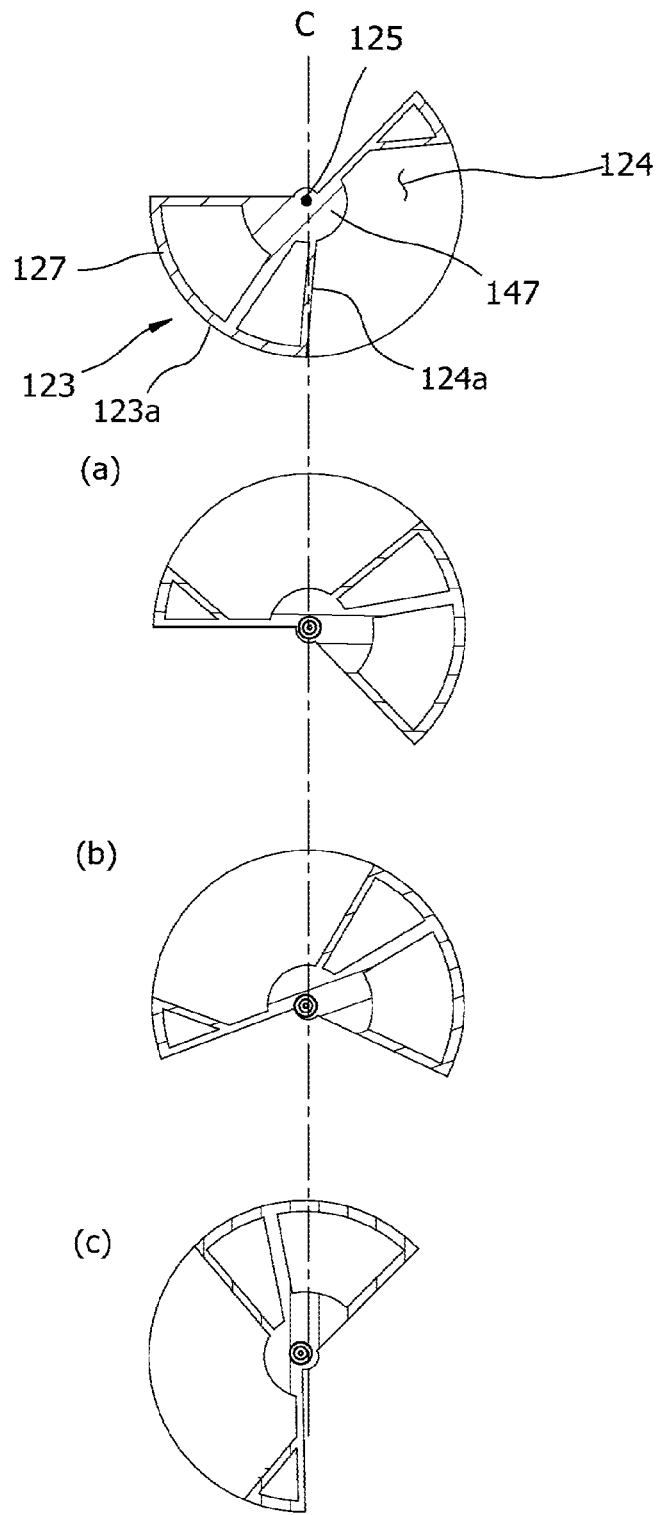
FIG. 57 is a significant part operational diagram of the contents movement device including the passage device according to the eighth embodiment of the present invention.

FIG. 56 is an operational diagram of the contents movement device including the passage device according to the eighth embodiment of the present invention, and FIG. 57 is a significant part operational diagram of the contents movement device including the passage device according to the eighth embodiment of the present invention.

As shown in FIGS. 53 to 57, the contents movement device 1 including the passage device 100 according to the eighth embodiment of the present invention includes the housing 110, the passage operation portion 120, and the supply guide portion 119.

In the embodiment, the contents 5 have a powder or flour form.

Of course, the contents having a powder or flour form may be applied in the above-described embodiments.

The operations of the passage operation portion 120 and the passage movement portion 140 are the same as the above description with respect to the first embodiment.

Meanwhile, the passage movement portion 140 is installed inside the opening portion 122 formed in a passage guide partitioning member 126 and may be assembled with the passage guide partitioning member 126 corresponding to an inside of the opening portion 122 to be circumferentially pivotable on the basis of the movement member 125.

Also, the passage movement portion 140 includes the opening member 124 and the blocking member 127 to sequentially open or close the opening portion 122. Here, the opening member 124 may have a bucket shape for stably discharging the contents 5 in the power form.

That is, when the housing 110 tilts more than the set angle, the contents 5 move into the opening member 124 while the passage movement portion 140 maintains an initial state in which the opening member 124 blocks the opening portion 122. Accordingly, the opening member 124 pivots counterclockwise as shown in FIG. 55 by a weight or a pushing force of the contents 5. Then, the contents 5 are guided to be discharged (to pass through)

Particularly, although the housing 110 tilts within a set angle or tilts more than the set angle, when the contents 5 do not pressurize and push the opening member 124, the blocking member 127 comes into contact with the stopper 129 such that the passage movement portion 140 maintains the initial state of blocking the opening portion 122.

The blocking member 127, in conjunction with the opening member 124 which pivots due to the contents 5, pivots on the basis of the movement member 125 and blocks the opening portion 122.

As a result, until the housing 110 tilts more than 90 degrees as shown in FIGS. 56 and 57, the contents 5 having a powder form do not come into contact with the passage movement portion 140 including the opening member 124 having a bucket shape. Here, the passage movement portion 140 is suppressed by the stopper 129 so as to not maintain weight balance by the opening member 124 having a bucket shape, the blocking member 127, and the movement control member 123a nor to rotate in a direction of rotating to maintain the weight balance so as to maintain a state in which the opening member 124 blocks the opening portion 122.

Accordingly, as shown in FIGS. 56 and 57(a), until the contents 5 push the opening member 124, the opening member 124 maintains the state of blocking the opening portion 122. Through this, like the first embodiment, a standby state is maintained in which the opening member 124 may resist the pushing force of the initial contents which intend to pass through the passage device 100 and the opening member 124 may rotate.

Then, as shown in FIGS. 56, 57(b), and 57(c), in the housing 110, when the opening member 124 is filled with the contents 5 having a powder form and is pushed by the weight of the contents, the passage movement portion 140 of the contents passage means 123 rotates counterclockwise on the basis of the movement member 125.

In addition, although the housing 110 tilts, when a force of the contents 5 pushing the opening member 124 does not occur, the opening member 124 may not tilt more than a tilting angle of the housing 110 from the initial position and maintain the initial state so as to block the opening portion.

Of course, when the housing 110 tilts more than a set angle of 90 degrees which is a horizontal state, the opening member 124 is filled with the contents 5 such that the opening member 124 rotates due to weight-leaning caused by the seesaw movement on the basis of the movement member 125 which occurs due to the weight of the contents 5 filling in the opening member 124.

Accordingly, the contents passage means 123 rotates counterclockwise on the basis of the movement member 125 and the opening member 124 faces the outside of the housing 110 such that the contents 5 may be discharged.

As the blocking member 127 blocks the opening portion 122 in conjunction with the rotational movement of the opening member 124, the opening portion 122 may be sequentially opened and closed by the opening member 124 and the blocking member 127 and a fixed quantity of the contents 5 may be withdrawn.

Particularly, FIGS. 56 and 57(*a*) to 57(*c*) illustrate a state in which the housing 110 tilts more than horizontality (−90 degrees or more). Here, the initial state in which the blocking member 127 is opened and the passage movement portion 140 does not move (pivot) is maintained. The contents 5 start moving while sliding along the incline of the inside of the housing 110 with a force in the gravitational direction C.

A first piece of the contents 5 does not move into the passage compartment portion 124*a* of the passage movement portion 140 or starts moving thereinto without contact with the passage compartment portion 124*a*.

Although the passage movement portion 140 tilts counterclockwise more than 90 degrees on the basis of the initial state due to the tilt of the housing 110, the contents 5 do not come into contact with the passage movement portion 140 and intend to rotate clockwise, which is a rightward direction, due to weight-leaning on a right side based on the movement member 125 but are suppressed by the stopper 129 to remain in a standby state.

FIGS. 56, 57(*a*), and 57(*b*) illustrate a state in which the blocking member 127 is opened and the contents 5 enter an internal space of the passage movement portion 140.

The weight of the contents 5 is added to the balancing portion 123*b* of the passage movement portion 124 such that weight-leaning on a left part of the gravitational vertical line C which is a side of the opening member 124 increases relatively. Accordingly, due to the balancing portion 123*b* and resistance of the contents 5, the passage movement portion 140 may rotate counterclockwise more than the tilt of the housing 110 while the contents 5 come into contact with the opening member 124 or approach to come into contact with the opening member 124.

Here, due to friction between the balancing portion 123*b* and the contents 5 which move along an incline in the gravitational direction or a force of pushing the opening member 124, the passage movement portion 140 moves with the contents 5 in a space of the passage compartment portion 124*a*.

FIGS. 56 and 57(*c*) illustrate a state in which the passage movement portion 140 rotates further counterclockwise on the basis of the movement member 125 from the initial state such that the blocking member 127 starts blocking contents 6 which enter after the fixed quantity of the contents 5.

Here, with the weight of the contents 5 having a tablet shape, a weight of the left side of the passage movement portion 140 on the basis of the gravitational vertical line C becomes greater than a weight of the right side such that weight leaning on the left side may occur and the passage movement portion 140 may rotate counterclockwise, that is, the left side of the rotational center of the movement member 125 to pass the contents 5 outward.

As shown in FIGS. 56 and 57(*c*), when the passage movement portion 140 rotates further counterclockwise on the basis of the movement member 125 from the initial state, the fixed quantity of the contents 5 pushing the passage movement portion 140 moves outward and does not come into contact with the opening member 124 side of the passage movement portion 140 any further such that the passage movement portion 140 has a greater weight on the right side based on the central line C and a force of rotating clockwise, that is, rightward, occurs. However, as the residual contents 6 come into contact with the blocking member 127 due to gravity, the valve 100 may not return to the right side and remain in a current state such that the contents 5 do not enter the space of the passage compartment portion 124*a* any further.

That is, the passage movement portion 140 is provided in the opening portion 122 to be movable like a seesaw such that the passage operation portion 120 remains in the initial state and the opening member 124 does not open the opening portion 122 when the passage operation portion 120 tilts within the set angle.

The opening portion 122 is opened by the force of the contents pushing on the passage movement portion 140 or the weight of the passage movement portion 140 and the force of the contents pushing on the passage movement portion 140 such that the set quantity of the contents is guided to pass through. The set angle may be set to be a tilting angle not more than 180 degrees from the initial state in which the contents movement device or accommodation device 1 with the opening portion 122 stands.

The passage movement portion 140 may perform the seesaw movement due to a weight-leaning phenomenon on the left side or the right side on the basis of the movement member 125 which is a rotational center. In the standby state in which the contents movement device or accommodation device 1 including the opening portion 122 tilts, a weight leans toward the blocking member 127 on the basis of the movement member 125 which is the rotational center and the blocking member 127 is held by the stopper such that the passage movement portion 140 may maintain a state in which the blocking member 127 does not block and opens the opening portion 122.

When the contents movement device or accommodation device 1 including the opening portion 122 tilts within a set angle, due to weight-leaning toward an opposite side of a tilting direction, the passage movement portion 140 may maintain a state in which the opening member 124 blocks the opening portion 122.

When the contents movement device or accommodation device 1 including the opening portion 122 tilts, the weight of the contents which move toward the opening portion 122 is added such that the passage movement portion 140 may pivot on the basis of the movement member 125, which is the rotational center, and open the opening portion 122. As described above, the passage movement portion 140 may reciprocally pivot at the opening portion 122 on the basis of the movement member 125 by using the principle of levers so as to open or close the opening portion 122.

When the passage operation portion 120 pivots within a set angle, the passage movement portion 140 may maintain a state of closing the opening portion 122 by the weight thereof and may sequentially open or close the opening portion 122 due to the pushing force of the contents or the force of the contents pushing on the passage movement portion 140 and the weight of the passage movement portion 140 so as to guide a passage of the set quantity of contents.

The passage movement portion 140 may include the balancing portion 123*b* configured to suppress the passage movement portion 140 so as to not tilt more than a tilt of the passage operation portion 120 due to the weight of the passage movement portion 140 when the passage operation portion 120 tilts.

The passage movement portion 140 may include the opening member 124 which moves in a direction in which the contents pass and forms a passage space for the contents. The passage movement portion 140 may include the blocking member 127, in conjunction with the opening member 124, which blocks at least a part of the opening portion 122 to block or partially pass the contents.

The passage operation portion 120 may have a shape which prevents pivoting caused by the weight of the passage movement portion 140 due to weight balance before the set quantity of contents comes into contact with the opening member 124. The passage movement portion 140 may further include the movement control member 123a for setting a balance in the center of gravity of lever movement.

Description of unstated reference numerals will be replaced by the above description.

Although the present invention has been described with reference to the embodiments shown in the drawings, it should be understood that the embodiments are merely examples and a variety of modifications and equivalents thereof may be made by one of ordinary skill in the art. Accordingly, the veritable technical scope of the present invention will be defined by the following claims.

The invention claimed is:

1. A passage device comprising a passage operation portion which has an opening portion and is configured to guide movement of contents,
    wherein the passage operation portion comprises a passage movement portion configured to be opened by movement to allow the contents to pass therethrough,
    wherein the passage movement portion is provided in the opening portion to be movable like a seesaw,
    wherein when the passage operation portion tilts within a set angle, the passage operation portion remains in an initial state and does not open the opening portion, and
    wherein the set angle is a tilting angle not more than 180 degrees from an initial state in which contents movement device, which includes the opening portion, stands.

2. The passage device of claim 1, wherein the contents movement device includes the passage device provided in the contents movement device, which stores contents, and a housing with at least one side being opened.

3. The passage device of claim 1, wherein the passage operation portion has a shape which prevents pivoting caused by the weight of the passage movement portion due to weight balance until the set quantity of contents comes into contact with an opening member.

4. The passage device of claim 1, wherein when the contents movement device including the opening portion tilts within the set angle, the passage movement portion remains in a state in which an opening member blocks the opening portion due to weight-leaning in a direction opposite to a tilting direction.

5. The passage device of claim 1, wherein the passage movement portion performs the seesaw movement due to a weight-leaning phenomenon of a lever on a left side or a right side based on a movement member which is a rotational center.

6. The passage device of claim 1, wherein the contents movement device including the opening portion tilts, a weight leans toward a blocking member on the basis of a movement member which is a rotational center, and the blocking member is held by a stopper such that the passage movement portion maintains a state in which the blocking member does not block and opens the opening portion.

7. The passage device of claim 1, wherein a set quantity of the contents is guided to pass by opening the opening portion due to a force of the contents pushing on the passage movement portion or due to a weight of the passage movement portion and the force of the contents pushing on the passage movement portion.

8. The passage device of claim 1, comprising a device body with which the passage operation portion is combined.

9. The passage device of claim 1, wherein the passage movement portion comprises an opening member which moves in a passage direction of the contents and forms a passage space for the contents.

10. The passage device of claim 9, wherein the passage movement portion, in conjunction with the opening member, comprises a blocking member which blocks at least a part of the opening portion so as to allow the contents to partially pass or not pass.

11. The passage device of claim 1, wherein the passage operation portion senses the discharged contents by using a sensor module.

12. The passage device of claim 11, wherein the sensor module comprises:
    a sensor portion which senses the contents which pass through the opening portion or approach the opening portion; and
    a sensing control portion which controls the sensor portion to sense the contents, generates medication-taking state information according to a result of sensing, and transmits the medication-taking state information to a medication-taking guide terminal.

13. The passage device of claim 12, wherein the sensing control portion emits light toward the opening portion by using the sensor portion and senses the contents on the basis of the light reflected by the contents which are discharged through the opening portion.

14. The passage device of claim 13, wherein the sensing control portion senses the contents discharged through the opening portion by using a time difference between a time of emitting the light and a time of receiving the light through the sensor portion.

15. The passage device of claim 14, wherein when the time difference is within a preset set value, the sensing control portion determines that the contents have passed through the opening portion.

16. A passage device comprising a passage operation portion which has an opening portion and is configured to guide movement of contents,
    wherein the passage operation portion comprises a passage movement portion configured to be opened by movement to allow the contents to pass therethrough,
    wherein the passage movement portion is provided in the opening portion to be movable like a seesaw, and
    wherein when a contents movement device including the opening portion tilts, a weight of the contents which move toward the opening portion is added such that the passage movement portion pivots on the basis of a movement member which is a rotational center and opens the opening portion.

17. A passage device comprising a passage operation portion which has an opening portion and is configured to guide movement of contents,
    wherein the passage operation portion comprises a passage movement portion configured to be opened by movement to allow the contents to pass therethrough,
    wherein the passage movement portion is provided in the opening portion to be movable like a seesaw, wherein when the passage operation portion tilts within a set angle, the passage operation portion remains in an initial state and does not open the opening portion, and wherein when the passage movement portion does not come into contact with the contents while the passage operation portion tilting within a set angle, the passage movement portion remains in the initial state due to a stopper.

18. A passage device comprising a passage operation portion which has an opening portion and is configured to guide movement of contents, wherein the passage operation portion comprises a contents passage means configured to move the contents, wherein the contents passage means comprises a passage movement portion configured to be opened by a pivoting movement to allow the contents to pass therethrough, wherein the passage movement portion reciprocally pivots using the principle of levers at the opening portion on the basis of a movement member so as to open or close the opening portion, wherein when the passage operation portion pivots within a set angle, the passage movement portion maintains a state in which the opening portion is closed due to a weight thereof and sequentially opens or closes the opening portion due to a pushing force of the contents or the weight of the passage movement portion and the force of the contents pushing on the passage movement portion so as to guide a set quantity of the contents to pass therethrough, and wherein the passage movement portion comprises a balancing portion which suppresses the passage movement portion from tilting more than a tilt of the passage operation portion due to the weight of the passage movement portion when the passage operation portion tilts.

19. The passage device of claim 18, wherein the passage operation portion has a shape which prevents pivoting caused by the weight of the passage movement portion due to weight balance until the set quantity of contents comes into contact with an opening member.

20. The passage device of claim 18, wherein the passage movement portion further comprises a movement control member for setting a balance of the center of gravity of lever movement.

21. The passage device of claim 18, wherein the passage movement portion comprises an opening member which moves in a passage direction of the contents and forms a passage space for the contents.

22. The passage device of claim 21, wherein the passage movement portion, in conjunction with the opening member, comprises a blocking member which blocks at least a part of the opening portion so as to allow the contents to partially pass or not pass.

23. A passage device comprising a passage operation portion which has an opening portion and is configured to guide movement of contents, wherein the passage operation portion comprises a passage movement portion configured to be opened by movement to allow the contents to pass therethrough, wherein the passage movement portion is provided in the opening portion to be movable like a seesaw, wherein when the passage operation portion tilts within a set angle, the passage operation portion remains in an initial state and does not open the opening portion, and wherein when contents movement device including the opening portion tilts within the set angle, the passage movement portion remains in a state in which an opening member blocks the opening portion due to weight-leaning in a direction opposite to a tilting direction.

24. A passage device comprising a passage operation portion which has an opening portion and is configured to guide movement of contents, wherein the passage operation portion comprises a passage movement portion configured to be opened by movement to allow the contents to pass therethrough, wherein the passage movement portion is provided in the opening portion to be movable like a seesaw, and wherein contents movement device including the opening portion tilts, a weight leans toward a blocking member on the basis of a movement member which is a rotational center, and the blocking member is held by a stopper such that the passage movement portion maintains a state in which the blocking member does not block and opens the opening portion.

* * * * *